US011859216B2

(12) United States Patent
Kralj et al.

(10) Patent No.: US 11,859,216 B2
(45) Date of Patent: Jan. 2, 2024

(54) **COMPOSITIONS AND METHODS COMPRISING THE USE OF A *BACILLUS AGARADHAERENS* INULOSUCRASE (INUO)**

(71) Applicant: DANISCO US INC, Palo Alto, CA (US)

(72) Inventors: Slavko Kralj, Oegstgeest (NL); Marc Kolkman, Oegstgeest (NL); Chris Leeflang, Twisk (NL); Johannes G. De Nobel, Heemstede (NL); Arjen Hoekstra, Leiden (NL); Veli Alkan, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 196 days.

(21) Appl. No.: 17/024,340

(22) Filed: Sep. 17, 2020

(65) Prior Publication Data
US 2022/0002685 A1 Jan. 6, 2022

Related U.S. Application Data

(63) Continuation of application No. 15/532,093, filed as application No. PCT/US2015/063841 on Dec. 4, 2015, now abandoned.

(60) Provisional application No. 62/088,320, filed on Dec. 5, 2014.

(51) Int. Cl.
| | |
|---|---|
| *C12N 9/10* | (2006.01) |
| *A61K 35/74* | (2015.01) |
| *C12P 19/18* | (2006.01) |
| *A61K 35/742* | (2015.01) |
| *A61K 38/45* | (2006.01) |

(52) U.S. Cl.
CPC .......... *C12N 9/1051* (2013.01); *A61K 35/742* (2013.01); *A61K 38/45* (2013.01); *C12N 9/1048* (2013.01); *C12P 19/18* (2013.01); *C12Y 204/01009* (2013.01)

(58) Field of Classification Search
CPC .................. C12N 9/1051; A61K 35/74; C12Y 204/01009
See application file for complete search history.

(56) References Cited

U.S. PATENT DOCUMENTS

| 7,507,558 B2 | 3/2009 | Wada et al. | |
|---|---|---|---|
| 2004/0009550 A1* | 1/2004 | Moll et al. ............... | C12P 21/02 435/69.1 |

FOREIGN PATENT DOCUMENTS

| EP | 427349 B1 | 12/1985 |
|---|---|---|
| WO | 95/07303 A1 | 3/1995 |
| WO | 95/12619 | 5/1995 |
| WO | 95/15984 A1 | 6/1995 |

OTHER PUBLICATIONS

Pijning et al. (2011) "Crystal Structure of Inulosucrase from Lactobacillus: Insights into the Substrate Specificity and Product Specificity of GH68 Fructansucrases", Journal of Molecular Biology, 412, 80-93. (Year: 2011).*
Wada et al. (2003) "A Novel Enzyme of *Bacillus* sp. 217C-11 that Produces Inulin form Sucrose" Biosci. Biotechnol. Biochem., 67(6):1327-1334. (Year: 2003).*
Communication pursuant to Article 94(3) EPC, Application No. 15 816 319.6 dated Oct. 2, 2018.
Database UniProt [Online] NCBI; May 28, 2013 (May 28, 2013), !! Glycosyl hydrolase family 68, includes levansucrase, betafructofuranosidase and inulosucrase;cd08997, Database accession No. WP_01 0502856.
Verraest et al. (1995) *Carbohydrate Res.* 271: 101-112.
Rogge et al. (2005) "Applicant of ethoxylated inulin in water-blown polyurethane foams." *BioMacromolecules* 6: 1992-1997.
Homann et al. (2012) "Chemo-enzymatic systhesis and in vitro cytokine profiling of tailor-made oligofructosides." *BMC Biotechnol.* 12: 90.
Van Hijum et al. (2006) *Microbiol. Mol. Biol. Rev.* 70: 157-176.
Meng et al. (2003) *Nat. Struct. Biol.* 10: 935-941.
Ozimek et al. (2004) *FEBS Lett.* 560: 131-133.
Velázquez-Hernández et al. (2009) *J. Appl. Microbiol.* 106: 1763-1778.

* cited by examiner

*Primary Examiner* — James D Schultz
*Assistant Examiner* — James Joseph Graber

(57) ABSTRACT

*Bacillus agaradhaerens* strain WDG185 expresses an inulosucrase that efficiently synthesizes a broad range of IOS with a GF range of GF3-GF30. The isolated and/or purified inulosucrase, recombinantly engineered variants thereof, active fragments thereof, synthetic nucleic acids encoding the inulosucrase, its variants, or its active fragments, host cells comprising the synthetic nucleic acids, and compositions comprising the inulosucrase are provided. Methods of using the compositions include the manufacture of inulooligosaccharides.

20 Claims, 9 Drawing Sheets

Specification includes a Sequence Listing.

MGIKKTYGDFLKWGVCTAILGSSLMASTVFATSDWDAEDDYTAVWTRQQAENVA

LEKDTTAPLLETDEDFELVAPDKVWDTWPLQNRDGSLAQVNGYTIAFALVAPR
                        ‾‾‾‾‾
                          I

DLGWGERHTEARIGMFYSKDGKDWTYAGIPYDYDKAYGHMQWAGSAMLDKDG/KV
                                         ‾‾‾‾‾     ‾‾ ‾‾
                                           II      III

HFFYTATGRKDNSEYFDQPGWEPMAEQRLAKTTFDISADKDGVHLTKEDEHQIR
‾‾‾‾‾‾
  IV

LEADGEYYETLGQWGSNGNIISAFRDPFFQDPNTGEEYIIWEGQAGPKSNGLR
                   ‾‾‾‾‾‾‾‾              ‾‾‾‾‾‾
                       V                    VI

PENIGDEAYRKNANVPDRAELYNGNIGIAKVLDEDVSELKMLPLLESIGVNHQ
                                         ‾‾‾‾‾‾‾‾  ‾‾
                                             VII

LERPHVVDGDTYYLLTISHIFTYAPGLTGPEGLYGFVNEGGLRGDYEPLNDGG
‾‾‾         ‾‾‾‾‾                            ‾‾‾‾‾
VIII          IX                                X

LVIGNPAESPGQAYSWWVAPDGQVISFINEPLDENGEVQFVGTFAPTLQLSFDG
            ‾‾‾
             XI

DQTKIEKEMGYGEIRPFGAYR (SEQ ID NO: 4)

*FIG. 2*

SEQUENCE LISTING

<160> NUMBER OF SEQ ID NOS: 19

<210> SEQ ID NO 1
<211> LENGTH: 47
<212> TYPE: DNA
<213> ORGANISM: artificial sequence
<220> FEATURE:
<223> OTHER INFORMATION: primer

<400> SEQUENCE: 1
ctcattctgc agctagcgca acctcagact gggatgctga agatgat          47

<210> SEQ ID NO 2
<211> LENGTH: 43
<212> TYPE: DNA
<213> ORGANISM: artificial sequence
<220> FEATURE:
<223> OTHER INFORMATION: primer

<400> SEQUENCE: 2
cgcagatatc gttaactcaa cgataggcac cgaatggtct gat              43

<210> SEQ ID NO 3
<211> LENGTH: 1359
<212> TYPE: DNA
<213> ORGANISM: B. agradhaerans

<400> SEQUENCE: 3
atgggaatta aaaaaacata tggtgatttt ttgaaatggg gagtatgcac ggcgatttta     60
ggaagctctc tgatggccag caccgttttt gccacctcag actgggatgc tgaagatgat    120

```
tacaccgcgg tttggacacg tcagcaagct gagaatgtgg ctttgacgaa agatacgacg    180
gcgcctcttt tggagacgga tgaggatttt gaactcgttg ctcccgataa atgggtttgg    240
gacacgtggc cacttcagaa cagggacggt tcacttgctc aggtgaatgg gtacacaatt    300
gcatttgcct tggttgctcc acgagattta ggttgggggg agcgtcatac tgaggctaga    360
atcggcatgt tctactccaa agacggaaaa gactggactt acgcaggtat tccatatgac    420
tatgacaaag cttacggtca catgcagtgg gctggttccg ccatgttgga caaggatgga    480
aaagtacatt tcttttatac tgcaacagga cgtaaggata attctgaata ttttgatcaa    540
ccaggatggg agccaatggc tgagcaacgc cttgctaaaa cgacgtttga catcagcgca    600
gacaaagacg gcgttcattt gactaaagaa gatgaacatc agatcatgct tgaggcagac    660
ggggaatatt acgaaacgct tggccaatgg ggaagtaacg gaaatatcat cagtgcgttt    720
cgtgatccgt ttttctttca ggaccctaac acaggggaag aatacattat ttgggaagga    780
caggcaggcc ctaaaagcaa tggtctgaag ccggaaaata tcggtgatga agcatatcgt    840
aaaaacgcta atgttccaga tagagcggaa ctttacaacg caacattgg gatagccaaa      900 gtacttgacg aggatgtctc cgaactaaaa atgttgccac cacttctcga atcaattggg    960
gtcaatcatc aactggaacg tccgcatgta gtggtggacg gtgacacgta ctacttgtta    1020
accatcagcc ataccttcac atacgcacct ggtttgactg gtccagaagg tttgtacggc    1080
tttgtcaatg aaggtgggtt acgaggtgat tacgaacctc tcaacgacgg tggtctagtg    1140
attggtaatc ctgctgaaag cccgggtcag gcctattctt ggtgggtagc tccagacgga    1200
caggttatca gcttcatcaa tgaacctctt gatgagaatg gagaagtcca attcgtgggt    1260
actttcgcgc cgacactaca actgtccttt gacggtgatc aaacaaaaat tgagaaggaa    1320
atgggttatg agaaatcag accattcggt gcctatcgt                            1359
```

<210> SEQ ID NO 4
<211> LENGTH: 453
<212> TYPE: PRT
<213> ORGANISM: B. agradhaerans

<400> SEQUENCE: 4

```
Met Gly Ile Lys Lys Thr Tyr Gly Asp Phe Leu Lys Trp Gly Val Cys
1               5                   10                  15

Thr Ala Ile Leu Gly Ser Ser Leu Met Ala Ser Thr Val Phe Ala Thr
                20                  25                  30

Ser Asp Trp Asp Ala Glu Asp Tyr Thr Ala Val Trp Thr Arg Gln
            35                  40                  45

Gln Ala Glu Asn Val Ala Leu Thr Lys Asp Thr Thr Ala Pro Leu Leu
        50                  55                  60

Glu Thr Asp Glu Asp Phe Glu Leu Val Ala Pro Asp Lys Trp Val Trp
65                  70                  75                  80

Asp Thr Trp Pro Leu Gln Asn Arg Asp Gly Ser Leu Ala Gln Val Asn
                85                  90                  95

Gly Tyr Thr Ile Ala Phe Ala Leu Val Ala Pro Arg Asp Leu Gly Trp
            100                 105                 110

Gly Glu Arg His Thr Glu Ala Arg Ile Gly Met Phe Tyr Ser Lys Asp
        115                 120                 125

Gly Lys Asp Trp Thr Tyr Ala Gly Ile Pro Tyr Asp Tyr Asp Lys Ala
    130                 135                 140

Tyr Gly His Met Gln Trp Ala Gly Ser Ala Met Leu Asp Lys Asp Gly
```

```
            145                 150                 155                 160
Lys Val His Phe Phe Tyr Thr Ala Thr Gly Arg Lys Asp Asn Ser Glu
                165                 170                 175

Tyr Phe Asp Gln Pro Gly Trp Glu Pro Met Ala Glu Gln Arg Leu Ala
            180                 185                 190

Lys Thr Thr Phe Asp Ile Ser Ala Asp Lys Asp Gly Val His Leu Thr
                195                 200                 205

Lys Glu Asp Glu His Gln Ile Met Leu Glu Ala Asp Gly Glu Tyr Tyr
            210                 215                 220

Glu Thr Leu Gly Gln Trp Gly Ser Asn Gly Asn Ile Ile Ser Ala Phe
225                 230                 235                 240

Arg Asp Pro Phe Phe Phe Gln Asp Pro Asn Thr Gly Glu Glu Tyr Ile
                245                 250                 255

Ile Trp Glu Gly Gln Ala Gly Pro Lys Ser Asn Gly Leu Lys Pro Glu
            260                 265                 270

Asn Ile Gly Asp Glu Ala Tyr Arg Lys Asn Ala Asn Val Pro Asp Arg
                275                 280                 285

Ala Glu Leu Tyr Asn Gly Asn Ile Gly Ile Ala Lys Val Leu Asp Glu
            290                 295                 300

Asp Val Ser Glu Leu Lys Met Leu Pro Pro Leu Leu Glu Ser Ile Gly
305                 310                 315                 320

Val Asn His Gln Leu Glu Arg Pro His Val Val Asp Gly Asp Thr
                325                 330                 335

Tyr Tyr Leu Leu Thr Ile Ser His Thr Phe Thr Tyr Ala Pro Gly Leu
            340                 345                 350

Thr Gly Pro Glu Gly Leu Tyr Gly Phe Val Asn Glu Gly Gly Leu Arg
                355                 360                 365

Gly Asp Tyr Glu Pro Leu Asn Asp Gly Leu Val Ile Gly Asn Pro
            370                 375                 380

Ala Glu Ser Pro Gly Gln Ala Tyr Ser Trp Trp Val Ala Pro Asp Gly
385                 390                 395                 400

Gln Val Ile Ser Phe Ile Asn Glu Pro Leu Asp Glu Asn Gly Glu Val
                405                 410                 415

Gln Phe Val Gly Thr Phe Ala Pro Thr Leu Gln Leu Ser Phe Asp Gly
            420                 425                 430

Asp Gln Thr Lys Ile Glu Lys Glu Met Gly Tyr Gly Glu Ile Arg Pro
                435                 440                 445

Phe Gly Ala Tyr Arg
            450

<210> SEQ ID NO 5
<211> LENGTH: 5
<212> TYPE: PRT
<213> ORGANISM: artificial sequence
<220> FEATURE:
<223> OTHER INFORMATION: conserved catalytic motif of GH68 enzymes
<220> FEATURE:
<221> NAME/KEY: MISC_FEATURE
<222> LOCATION: (1)..(1)
<223> OTHER INFORMATION: X is V or L
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (5)..(5)
<223> OTHER INFORMATION: X is W or M
```

```
<400> SEQUENCE: 5

Xaa Trp Asp Xaa Xaa
1               5

<210> SEQ ID NO 6
<211> LENGTH: 5
<212> TYPE: PRT
<213> ORGANISM: artificial sequence
<220> FEATURE:
<223> OTHER INFORMATION: conserved catalytic motif of GH68 enzymes
<220> FEATURE:
<221> NAME/KEY: MISC_FEATURE
<222> LOCATION: (2)..(2)
<223> OTHER INFORMATION: X is E or Q
<220> FEATURE:
<221> NAME/KEY: MISC_FEATURE
<222> LOCATION: (3)..(3)
<223> OTHER INFORMATION: X is I or T

<400> SEQUENCE: 6

Asp Xaa Xaa Glu Arg
1               5

<210> SEQ ID NO 7
<211> LENGTH: 473
<212> TYPE: PRT
<213> ORGANISM: B. subtilis

<400> SEQUENCE: 7

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240
```

```
Asp Asn His Thr Leu Arg Asp Pro His Tyr Val Glu Asp Lys Gly His
            245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
            275                 280                 285

Phe Phe Arg Gln Glu Ser Gln Lys Leu Leu Gln Ser Asp Lys Lys Arg
290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
            325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
            355                 360                 365

Ile Thr Ser Asn Asp Ile Tyr Met Leu Gly Tyr Val Ser Asn Ser Leu
            370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
            405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
            435                 440                 445

Leu Asn Ile Lys Gly Lys Lys Thr Ser Val Val Lys Asp Ser Ile Leu
            450                 455                 460

Glu Gln Gly Gln Leu Thr Val Asn Lys
465                 470

<210> SEQ ID NO 8
<211> LENGTH: 484
<212> TYPE: PRT
<213> ORGANISM: B. megaterium

<400> SEQUENCE: 8

Met Lys Met Lys Arg Val Ala Lys His Thr Thr Ala Ala Thr Leu Ala
1               5                   10                  15

Ala Ala Leu Leu Val Gly Gly Gly Tyr Gln Thr Phe Ala Lys Gly Asn
            20                  25                  30

Asp Ser Lys Asp Phe Asn Asn Ser Tyr Gly Ile Ser His Ile Thr Arg
            35                  40                  45

Asp Asn Met Val Lys Ile Pro Gln Gln Asn Ser Asp Gln Phe Lys
50                  55                  60

Val Pro Ala Phe Asp Glu Ser Thr Ile Lys Asn Ile Ala Ser Ala Lys
65                  70                  75                  80

Gly Lys Asn Ala Ser Gly Asn Thr Ile Asp Leu Asp Val Trp Asp Ser
            85                  90                  95

Trp Pro Leu Gln Asn Ala Asp Gly Thr Val Ala Thr Tyr His Gly Tyr
            100                 105                 110

Gln Ile Val Phe Ala Leu Ala Gly Asp Pro Lys Asp Ser Asn Asp Thr
            115                 120                 125

Ser Val Tyr Leu Phe Tyr Lys Lys Ala Gly Asp Lys Ser Ile Asp Ser
            130                 135                 140
```

Trp Lys Asn Ala Gly Arg Val Phe Lys Asp Ser Asp Lys Phe Val Pro
145                 150                 155                 160

Asn Asp Pro His Leu Lys Asn Gln Thr Gln Glu Trp Ser Gly Ser Gly
                165                 170                 175

Thr Leu Thr Lys Asp Gly Lys Val Arg Leu Phe Tyr Thr Asp Tyr Ser
            180                 185                 190

Gly Lys Gln Tyr Gly Lys Gln Thr Leu Thr Thr Ala Gln Val Asn Met
        195                 200                 205

Ser Gln Pro Asn Asp Asn Thr Leu Lys Val Asp Gly Val Glu Asp Tyr
    210                 215                 220

Lys Ser Ile Phe Asp Gly Asp Gly Lys Ile Tyr Gln Thr Val Gln Gln
225                 230                 235                 240

Phe Ile Asp Glu Gly Gly Tyr Asp Thr Gly Asp Asn His Thr Leu Arg
                245                 250                 255

Asp Pro His Tyr Ile Glu Asp Asn Gly His Lys Tyr Leu Val Phe Glu
            260                 265                 270

Ala Asn Thr Gly Thr Glu Asp Gly Tyr Gln Gly Glu Asp Ser Leu Tyr
        275                 280                 285

Asn Arg Ala Tyr Tyr Gly Gly Asn Asn Pro Phe Phe Gln Ser Glu Lys
    290                 295                 300

Lys Lys Leu Leu Glu Gly Ser Asn Lys Glu Lys Ala Ser Leu Ala Asn
305                 310                 315                 320

Gly Ala Leu Gly Ile Ile Glu Leu Asn Asp Asp Tyr Thr Leu Lys Lys
                325                 330                 335

Val Met Lys Pro Leu Ile Thr Ser Asn Thr Val Thr Asp Glu Ile Glu
            340                 345                 350

Arg Ala Asn Ile Phe Lys Lys Asp Gly Lys Trp Tyr Leu Phe Thr Asp
        355                 360                 365

Ser Arg Gly Ser Lys Met Thr Ile Asp Gly Ile Gly Gln Asp Asp Val
    370                 375                 380

Tyr Met Leu Gly Tyr Val Ser Asn Thr Leu Thr Gly Lys Tyr Lys Pro
385                 390                 395                 400

Leu Asn Asp Thr Gly Leu Val Leu His Met Asp Leu Asp Pro Asn Asp
                405                 410                 415

Lys Thr Phe Thr Tyr Ser His Phe Ala Val Pro Gln Thr Lys Gly Asp
            420                 425                 430

Asn Val Val Ile Thr Ser Tyr Met Thr Asn Arg Gly Phe Tyr Glu Asp
        435                 440                 445

Asn His Ser Thr Phe Ala Pro Ser Phe Leu Val Asn Ile Asp Gly Ser
    450                 455                 460

Lys Thr Ser Val Val Lys Asp Arg Val Leu Glu Gln Gly Gln Leu Thr
465                 470                 475                 480

Val Asp Glu Asp

<210> SEQ ID NO 9
<211> LENGTH: 1022
<212> TYPE: PRT
<213> ORGANISM: L. mesenteroides

<400> SEQUENCE: 9

Met Arg Lys Lys Leu Tyr Lys Ala Gly Lys Leu Trp Val Ala Gly Ala
1               5                   10                  15

Ala Val Arg Leu Gln Ser Trp Ala Pro Asn Ile Val Ser Ala Asp Thr
            20                  25                  30

```
Thr Asn Ser Thr Thr Thr Ala Asp Ala Thr Thr Thr Ser Ser Ala Thr
         35                  40                  45

Glu Ser Ser Ile Ser Ser Thr Glu Ser Asp Asp Asn Lys Val Asp Thr
 50                  55                  60

Ser Asn Thr Asp Ala Val Thr Val Thr Thr Asn Ser Asp Asp Ser Asn
 65                  70                  75                  80

Ser Asn Ser Ala Glu Thr Ser Asn Ser Asp Ala Lys Val Thr Ser Asn
                 85                  90                  95

Asn Thr Ala Gln Lys Asp Glu Ala Ile Lys Ala Glu Thr Thr Asn Asn
                100                 105                 110

Gln Asp Thr Thr Ser Thr Thr Ala Val Ala Glu Thr Lys Thr Ala Val
             115                 120                 125

Asn Thr Ser Glu Ser Glu Ser Gly Ser Asn Asn Glu Gln Leu Ala Glu
             130                 135                 140

Thr Ala Thr Asp Asn Ala Lys Val Asn Asp Ala Ser Ser Gln Lys Gln
145                 150                 155                 160

Ser Thr Pro Ser Val Glu Lys Leu Asp Asp Ser Val Ser Lys Asp Leu
                 165                 170                 175

Asn Ser Lys Thr Thr Val Val Thr Lys Asn Ala Asp Gly Thr Ser Thr
             180                 185                 190

Thr Asn Met Thr Tyr Ala Asn Leu Lys Asp Val Ala Asp Asn Ile Ala
             195                 200                 205

Ser Leu Asn Pro Asp Thr Ser Val Pro Tyr Phe Asn Ala Asp Ala Ile
210                 215                 220

Lys Asn Leu Pro Ala Met Thr Thr Ala Asp Ala Gln Thr Gly Gln Ile
225                 230                 235                 240

Gln Asp Leu Asp Val Trp Asp Ser Trp Ala Leu Gln Asp Ala Lys Thr
                 245                 250                 255

Gly Ala Val Ala Asn Tyr His Gly Tyr Asn Ile Val Phe Ala Leu Ala
             260                 265                 270

Gly Tyr Pro Lys Glu Asp Asn Asp Gln His Ile Tyr Met Leu Tyr Thr
             275                 280                 285

Lys Tyr Gly Asp Thr Ala Leu Asn Asn Trp Lys Asn Ala Gly Pro Val
290                 295                 300

Phe Gly Phe Asn Ala Lys Trp Asn Glu Gln Gln Trp Ser Gly Ser Ala
305                 310                 315                 320

Thr Val Asn Asp Asp Asp Ser Ile Gln Leu Phe Tyr Thr Lys Thr Asp
                 325                 330                 335

Gln Pro Asn Thr Val Gln Arg Leu Ala Thr Ala Asn Leu Ser Met Thr
             340                 345                 350

Tyr Thr Asp Thr Glu Val Tyr Val Ala Lys Val Asn Asp Asp His Val
             355                 360                 365

Leu Phe Ala Gly Asp Gly Glu Tyr Tyr Gln Thr Leu Gln Gln Trp Val
370                 375                 380

Asp Ala Gly Tyr Tyr Thr Thr Gly Asp Asn Phe Thr Met Arg Asp Pro
385                 390                 395                 400

His Val Ile Glu Val Asn Gly Glu Arg Tyr Leu Ala Phe Glu Ala Asn
                 405                 410                 415

Thr Gly Thr Asn Asn Tyr Gln Ser Asp Asp Ala Val Asn Asp Asp Thr
             420                 425                 430

Tyr Tyr Gly Gly Thr Glu Glu Phe Asn Gln Gln Ala Lys Val Asp Thr
             435                 440                 445
```

```
Leu Gln Asn Pro Asp Lys Leu Lys Leu Ser Lys Lys Ala Asn Gly Ala
    450                 455                 460
Ile Gly Leu Ile Lys Leu Thr Lys Asp Gln Asn Asn Pro Thr Val Ala
465                 470                 475                 480
Gln Val Tyr Ser Pro Leu Leu Ala Ala Asn Gly Ile Thr Asp Glu Ile
                485                 490                 495
Glu Arg Ala Asn Ile Val Pro Leu Asn Gly Lys Phe Tyr Leu Phe Thr
                500                 505                 510
Asp Thr Arg Leu Ser Lys Ser Val Pro Thr Ala Asp Phe Asn Ile
                515                 520                 525
Asn Val Gly Met Met Gly Tyr Val Ser Asp Ser Leu Phe Gly Pro Tyr
530                 535                 540
Thr Pro Leu Asn Gly Ser Gly Ser Val Val Thr Gly Thr Gln Leu Phe
545                 550                 555                 560
Thr Ser Arg Thr Asp Thr Tyr Ser Tyr Tyr Ala Val Pro Val Glu Gly
                565                 570                 575
Arg Ser Asp Leu Leu Val Thr Ser Tyr Met Ser Asn Arg Asn Glu
                580                 585                 590
Lys Ala Gly Thr Gly Met Asn Ala Thr Phe Ala Pro Ser Phe Leu Ile
                595                 600                 605
Gln Ile Ser Ala Asp Gly Met Ser Thr Lys Val Leu Asp Thr Val Leu
                610                 615                 620
Ala Gln Gly Thr Trp Thr Tyr Asp Gly Lys Ser Ala Ser Val Glu Glu
625                 630                 635                 640
Leu Val Gly Asn Lys Ala Thr Ser Glu Leu Thr Asp Met Lys Ile Gly
                645                 650                 655
Trp Val Asp Asn Lys Phe Tyr Val Asp Asn Glu Leu Ala Asn Gly Tyr
                660                 665                 670
Val Tyr Asp Tyr Ile Asn Thr Ser Tyr Tyr Leu Phe Lys Asn Gly Val
                675                 680                 685
Arg Leu Ser Gly Val Gln Thr Tyr Ala Asn Ser Tyr Tyr Tyr Phe Asp
                690                 695                 700
Pro Val Thr Tyr Lys Arg Val Asp Asn Glu Ile His Gln Asp Asn Thr
705                 710                 715                 720
Gly Lys Lys Tyr Tyr Phe Gly Asn Asp Gly Arg Val Lys Gln Gly Gln
                725                 730                 735
Phe Ala Val Asn Gly Val Ala Tyr Asn Phe Gly Asn Asp Lys Thr Tyr
                740                 745                 750
Tyr Glu Arg Gly Phe Ala Ser Gly Tyr Leu Gln Asp Val Thr Asp Asn
                755                 760                 765
Asn Gln Trp Tyr Trp Phe Glu Ser Gly Lys Lys Tyr Thr Gly Phe Arg
770                 775                 780
Tyr Tyr Met Gly Thr Tyr Tyr Phe Phe Glu Thr Gly Gln Arg Gln Glu
785                 790                 795                 800
Ser Lys Trp Glu Thr Ala Trp Gly Met Lys Tyr Val Gly Thr Asp
                805                 810                 815
Gly Arg Ala Val Gln Gly Val Gln Ile Ile Asp Gly Gln Ala Tyr Asp
                820                 825                 830
Phe Gly Thr Asn Gly Thr Phe Asn Leu Lys Gly Thr Ala Ser Gly Tyr
                835                 840                 845
Leu Tyr Ser Pro Ser Leu Ser Thr Ala Asn Gly Tyr Asn Trp Phe
850                 855                 860
Glu Asn Gly Lys Pro Tyr Thr Gly Phe Arg Tyr Tyr Glu Gly Thr Tyr
```

```
                 865                 870                 875                 880
Tyr Trp Phe Val Asn Gly Val Arg Gln Asn Ala Gly Trp Arg Glu Ala
                        885                 890                 895

Trp Gly Met Lys Tyr Tyr Thr Asp Ala Ser Gly Arg Ala Leu Gln Gly
                        900                 905                 910

Ile Gln Ile Ile Asp Gly Gln Ala Tyr Asp Phe Gly Thr Asn Gly Thr
                        915                 920                 925

Tyr Asn Leu Lys Ser Ala Ala Ser Gly Tyr Leu Tyr Ser Pro Ser Tyr
                        930                 935                 940

Ser Lys Ala Asn Gly Gly Tyr Asn Trp Phe Glu Asn Gly Lys Pro Tyr
945                 950                 955                 960

Thr Gly Phe Arg Tyr Tyr Met Gly Thr Tyr Tyr Trp Phe Val Asn Gly
                        965                 970                 975

Val Arg Gln Asn Ala Gly Trp Arg Glu Ala Trp Gly Lys Tyr Tyr
                        980                 985                 990

Thr Asp Ala Asn Gly Arg Ala Leu Gln Gly Ile Gln Lys Ile Asp Gly
                        995                1000                1005

Gln Gln Tyr Asn Phe Gly Asn Asp Gly Thr Tyr Tyr Leu Arg
       1010                1015                1020
```

<210> SEQ ID NO 10
<211> LENGTH: 651
<212> TYPE: PRT
<213> ORGANISM: L. gasseri

<400> SEQUENCE: 10

```
Met Leu Glu Asn Lys Asn His Lys Lys Met Ser Leu Ser Gly Lys Ser
1               5                   10                  15

Leu Leu Met Gly Thr Leu Ser Thr Ala Ala Ile Val Leu Ser Ala Ser
                20                  25                  30

Thr Val Asn Ala Ala Thr Thr Asn Ala Asp Asn Val Asn Glu Asn Lys
            35                  40                  45

Thr Val Ala Val Ser Thr Thr Thr Ser Ala Asn Asn Lys Asn Asn Asn
        50                  55                  60

Gln Val Asn Ser Ser Ser Glu Lys Ser Val Asp Thr Lys Ala Glu Lys
65                  70                  75                  80

Ala Thr Thr Val Thr Ser Ala Ala Thr Lys Glu Val Lys Ala Asp Ala
                85                  90                  95

Val Asn Thr Ser Pro Val Asn Asn Val Lys Ala Ala Thr Thr Ser Thr
                100                 105                 110

Thr Thr Thr Lys Glu Thr Val Asp Gly Thr Glu Lys Thr Pro Val Asn
                115                 120                 125

Ser Ser Ala Asp Val Lys Lys Asn Asp Ala Val Lys Gln Asp Glu Lys
        130                 135                 140

Ala Ala Thr Ser Phe Lys Thr Asn Thr Glu Glu Lys Ala Asn Glu Thr
145                 150                 155                 160

Ser Thr Lys Thr Ala Ser Asn Asp Asn Lys Ala Glu Leu Lys Gly Gln
                165                 170                 175

Ile Lys Asp Ile Val Lys Glu Ser Asp Val Asp Thr Ser Lys Leu Thr
                180                 185                 190

Asn Asp Gln Ile Asn Glu Leu Asn Lys Ile Asn Phe Ser Lys Glu Ala
            195                 200                 205

Lys Ser Gly Thr Gln Leu Thr Tyr Ser Asp Phe Lys Lys Ile Ala Lys
        210                 215                 220
```

```
Thr Leu Ile Glu Gln Asp Ala Arg Tyr Ala Ile Pro Phe Phe Asn Ala
225                 230                 235                 240

Ser Lys Ile Lys Asn Met Pro Ala Ala Lys Thr Met Asp Ala Gln Thr
            245                 250                 255

Gly Lys Val Glu Asp Leu Glu Ile Trp Asp Ser Trp Pro Val Gln Asp
        260                 265                 270

Ala Lys Thr Gly Tyr Val Ser Asn Trp Asn Gly Tyr Gln Leu Val Val
    275                 280                 285

Gly Met Met Gly Val Pro Asn Thr Asn Asp Asn His Ile Tyr Leu Leu
290                 295                 300

Tyr Asn Lys Tyr Gly Asp Asn Asn Phe Asn Asn Trp Lys Asn Ala Gly
305                 310                 315                 320

Pro Ile Phe Gly Leu Gly Thr Pro Val Ile Gln Gln Trp Ser Gly Ser
            325                 330                 335

Ala Thr Leu Asn Lys Asp Gly Ser Ile Gln Leu Tyr Tyr Thr Lys Val
            340                 345                 350

Asp Thr Ser Asp Asn Asn Thr Asn His Gln Lys Ile Ala Ser Ala Thr
            355                 360                 365

Val Tyr Leu Asn Leu Glu Lys Asp Gln Asp Lys Ile Ser Ile Ala His
370                 375                 380

Val Asp Asn Asp His Ile Val Phe Glu Gly Asp Gly Tyr His Tyr Gln
385                 390                 395                 400

Thr Tyr Asn Gln Trp Lys Lys Thr Asn Lys Gly Ala Asp Asn Ile Ala
            405                 410                 415

Met Arg Asp Ala His Val Ile Asp Asp Lys Asp Gly Asn Arg Tyr Leu
            420                 425                 430

Val Phe Glu Ala Ser Thr Gly Thr Glu Asn Tyr Gln Gly Ala Asp Gln
            435                 440                 445

Ile Tyr Gln Trp Leu Asn Tyr Gly Gly Thr Asn Lys Asp Asn Leu Gly
            450                 455                 460

Asp Phe Phe Gln Ile Leu Ser Asn Ser Asp Ile Lys Asp Arg Ala Lys
465                 470                 475                 480

Trp Ser Asn Ala Ala Ile Gly Ile Ile Lys Leu Asn Asn Asp Thr Lys
            485                 490                 495

Asn Pro Gly Val Glu Lys Val Tyr Thr Pro Phe Ile Ser Ser Pro Met
            500                 505                 510

Val Ser Asp Glu Ile Glu Arg Pro Asp Val Val Arg Leu Gly Asn Lys
            515                 520                 525

Tyr Tyr Leu Phe Ala Ala Thr Arg Leu Asn Arg Gly Ser Asn Asp Asp
530                 535                 540

Ala Trp Met Ala Ala Asn Lys Ala Val Gly Asp Asn Val Ala Met Ile
545                 550                 555                 560

Gly Tyr Val Ser Asp Asn Leu Thr His Gly Tyr Val Pro Leu Asn Glu
            565                 570                 575

Ser Gly Val Val Leu Thr Ala Ser Val Pro Ala Asn Trp Arg Thr Ala
            580                 585                 590

Thr Tyr Ser Tyr Tyr Ala Val Pro Val Glu Gly Arg Asp Asp Gln Leu
            595                 600                 605

Leu Ile Thr Ser Tyr Ile Thr Asn Arg Gly Glu Val Ala Gly Lys Gly
            610                 615                 620

Met His Ala Thr Trp Ala Pro Ser Phe Leu Leu Gln Ile Asn Pro Asp
625                 630                 635                 640

Asn Thr Thr Thr Val Leu Ala Lys Met Thr Asn
```

<210> SEQ ID NO 11
<211> LENGTH: 761
<212> TYPE: PRT
<213> ORGANISM: L. gasseri

<400> SEQUENCE: 11

```
Met Leu Glu Asn Lys Asn His Lys Lys Met Ser Leu Ser Gly Lys Ser
1               5                   10                  15

Leu Leu Met Gly Thr Leu Ser Thr Ala Ala Ile Val Leu Ser Ala Ser
            20                  25                  30

Thr Val Asn Ala Ala Thr Thr Asn Ala Asp Asn Val Thr Lys Asn Gln
        35                  40                  45

Thr Val Ala Val Ser Ala Thr Thr Thr Asn Asn Glu Thr Asn Asn Gln
    50                  55                  60

Val Ser Ser Ser Glu Lys Thr Ala Asp Ser Lys Thr Glu Lys Asp
65                  70                  75                  80

Thr Asn Leu Thr Ser Ala Ala Thr Lys Glu Val Lys Ala Asp Ala Ala
                85                  90                  95

Lys Thr Thr Ser Pro Val Asn Asn Val Lys Thr Val Ala Asp Thr Thr
            100                 105                 110

Thr Thr Thr Lys Glu Thr Thr Asp Asn Thr Glu Lys Ser Pro Val Asn
        115                 120                 125

Phe Ser Ala Asp Val Lys Lys Asn Asp Ala Val Lys Gln Asp Glu Lys
    130                 135                 140

Ala Ala Thr Ala Val Lys Ala Asn Thr Glu Val Lys Ala Asn Glu Thr
145                 150                 155                 160

Ser Thr Lys Ser Ala Ser Lys Asp Asn Lys Ala Glu Leu Lys Gly Gln
                165                 170                 175

Ile Lys Asp Ile Val Lys Glu Ser Gly Val Asp Thr Ser Lys Leu Thr
            180                 185                 190

Asp Asp Gln Ile Asn Glu Leu Asn Lys Ile Ser Phe Ser Lys Glu Ala
        195                 200                 205

Lys Ser Gly Thr Gln Leu Thr Tyr Ser Asp Phe Lys Lys Ile Ala Lys
    210                 215                 220

Thr Leu Ile Glu Gln Asp Ala Arg Tyr Ala Val Pro Phe Phe Asn Ala
225                 230                 235                 240

Ser Lys Ile Lys Asn Met Pro Ala Ala Lys Thr Leu Asp Ala Gln Thr
                245                 250                 255

Gly Lys Val Glu Asp Leu Glu Ile Trp Asp Ser Trp Pro Val Gln Asp
            260                 265                 270

Ala Lys Thr Gly Tyr Val Ser Asn Trp Asn Gly Tyr Gln Leu Val Ile
        275                 280                 285

Gly Met Met Gly Val Pro Asn Thr Asn Asp Asn His Ile Tyr Leu Leu
    290                 295                 300

Tyr Asn Lys Tyr Gly Asp Asn Asn Phe Asn Asn Trp Lys Asn Ala Gly
305                 310                 315                 320

Pro Ile Phe Gly Leu Gly Thr Pro Val Ile Gln Gln Trp Ser Gly Ser
                325                 330                 335

Ala Thr Leu Asn Lys Asp Gly Ser Ile Gln Leu Tyr Tyr Thr Lys Val
            340                 345                 350

Asp Thr Ser Asp Asn Asn Thr Asn His Gln Lys Ile Ala Ser Ala Thr
        355                 360                 365
```

```
Val Tyr Leu Asn Leu Glu Lys Asn Gln Asp Lys Ile Ser Ile Ala His
    370                 375                 380

Val Asp Asn Asp His Ile Val Phe Glu Gly Asp Gly Tyr His Tyr Gln
385                 390                 395                 400

Thr Tyr Asn Gln Trp Lys Lys Thr Asn Lys Gly Ala Asp Asn Ile Ala
                405                 410                 415

Met Arg Asp Ala His Val Ile Asp Asp Lys Asp Gly Asn Arg Tyr Leu
            420                 425                 430

Val Phe Glu Ala Ser Gly Thr Glu Asn Tyr Gln Gly Ala Asp Gln
        435                 440                 445

Ile Tyr Gln Trp Leu Asn Tyr Gly Gly Thr Asn Lys Asp Asn Leu Gly
    450                 455                 460

Asp Phe Leu Gln Ile Leu Ser Asn Ser Asp Ile Lys Asp Arg Ala Lys
465                 470                 475                 480

Trp Ser Asn Ala Ala Ile Gly Ile Ile Lys Leu Asn Asn Asp Thr Lys
                485                 490                 495

Asn Pro Gly Val Glu Lys Val Tyr Thr Pro Leu Ile Ser Ala Pro Met
            500                 505                 510

Val Ser Asp Glu Ile Glu Arg Pro Asp Val Val Arg Leu Gly Asn Lys
        515                 520                 525

Tyr Tyr Leu Phe Ala Ala Thr Arg Leu Asn Arg Gly Ser Asn Asp Asp
    530                 535                 540

Ala Trp Met Ala Ala Asn Lys Ala Val Gly Asp Asn Val Ala Met Ile
545                 550                 555                 560

Gly Tyr Val Ser Asp Asn Leu Thr His Gly Tyr Val Pro Leu Asn Glu
                565                 570                 575

Ser Gly Val Val Leu Thr Ala Ser Val Pro Ala Asn Trp Arg Thr Ala
            580                 585                 590

Thr Tyr Ser Tyr Tyr Ala Val Pro Val Glu Gly Arg Asp Asp Gln Leu
        595                 600                 605

Leu Ile Thr Ser Tyr Ile Thr Asn Arg Gly Glu Val Ala Gly Lys Gly
    610                 615                 620

Met His Ala Thr Trp Ala Pro Ser Phe Leu Leu Gln Ile Asn Pro Asp
625                 630                 635                 640

Asn Thr Thr Thr Val Leu Ala Lys Met Thr Asn Gln Gly Asp Trp Ile
                645                 650                 655

Trp Asp Asp Ser Ser Glu Asn Ala Asp Met Met Gly Val Leu Glu Lys
            660                 665                 670

Asp Ala Pro Asn Ser Ala Ala Leu Pro Gly Glu Trp Gly Lys Pro Val
        675                 680                 685

Asp Trp Asp Leu Ile Gly Gly Tyr Asn Leu Lys Pro His Gln Pro Val
    690                 695                 700

Thr Pro Ile Pro Asn Val Pro Thr Thr Pro Glu Lys Pro Glu Asn Pro
705                 710                 715                 720

Thr Thr Pro Asn Thr Pro Asp Thr Pro His Thr Pro Thr Thr Pro Asn
                725                 730                 735

Thr Pro Asp Thr Pro Arg Thr Pro Glu Val Pro Thr Thr Pro Val Lys
            740                 745                 750

Lys Thr Thr Gln Ser Glu Leu Arg Ser
        755                 760

<210> SEQ ID NO 12
<211> LENGTH: 797
<212> TYPE: PRT
```

<213> ORGANISM: L. johnsonii

<400> SEQUENCE: 12

```
Met Leu Glu Asn Lys Asn His Lys Lys Ile Ser Leu Ser Gly Lys Ser
1               5                   10                  15

Leu Leu Met Gly Thr Leu Ser Thr Ala Ala Ile Val Leu Ser Ala Ser
            20                  25                  30

Thr Ala Asn Ala Ala Thr Ile Asn Ala Asp Asn Val Asn Glu Asn Gln
        35                  40                  45

Thr Val Glu Val Thr Ala Ser Ser Val Asn Asn Glu Asn Asn Lys Gln
    50                  55                  60

Val Thr Glu Lys Asp Ser Ala Asp Lys Ser Thr Ser Asp Val Ala Glu
65                  70                  75                  80

Asp Ala Asn Thr Lys Lys Ser Asn Glu Asn Thr Glu Thr Thr Glu Lys
                85                  90                  95

Asn Thr Gln Thr Val Val Thr Asn Ala Pro Val Ser Asp Val Lys Asn
            100                 105                 110

Thr Asn Thr Val Thr Ala Glu Thr Pro Val Asp Lys Val Val Asn Asn
        115                 120                 125

Ser Asp Gln Lys Thr Thr Asn Ala Ala Thr Thr Asp Thr Lys Lys Asp
    130                 135                 140

Asp Val Lys Gln Val Glu Lys Lys Asp Ser Val Asp Lys Thr Asn Ala
145                 150                 155                 160

Glu Glu Asn Lys Asp Ser Ser Val Lys Pro Ala Glu Asn Ala Thr Lys
                165                 170                 175

Ala Glu Leu Lys Gly Gln Val Lys Asp Ile Val Glu Glu Ser Gly Val
            180                 185                 190

Asp Thr Ser Lys Leu Thr Asn Asp Gln Ile Asn Glu Leu Asn Lys Ile
        195                 200                 205

Asn Phe Ser Lys Glu Ala Lys Ser Gly Thr Gln Leu Thr Tyr Asn Asp
    210                 215                 220

Phe Lys Lys Ile Ala Lys Thr Leu Ile Glu Gln Asp Ala Arg Tyr Ala
225                 230                 235                 240

Ile Pro Phe Phe Asn Ala Ser Lys Ile Lys Asn Met Pro Ala Ala Lys
                245                 250                 255

Thr Leu Asp Ala Gln Ser Gly Lys Val Glu Asp Leu Glu Ile Trp Asp
            260                 265                 270

Ser Trp Pro Val Gln Asp Ala Lys Thr Gly Tyr Val Ser Asn Trp Asn
        275                 280                 285

Gly Tyr Gln Leu Val Ile Gly Met Met Gly Val Pro Asn Val Asn Asp
    290                 295                 300

Asn His Ile Tyr Leu Leu Tyr Asn Lys Tyr Gly Asp Asn Asp Phe Asn
305                 310                 315                 320

His Trp Lys Asn Ala Gly Pro Ile Phe Gly Leu Gly Thr Pro Val Ile
                325                 330                 335

Gln Gln Trp Ser Gly Ser Ala Thr Leu Asn Lys Asp Gly Ser Ile Gln
            340                 345                 350

Leu Tyr Tyr Thr Lys Val Asp Thr Ser Asp Asn Thr Asn His Gln
        355                 360                 365

Lys Leu Ala Ser Ala Thr Val Tyr Leu Asn Leu Glu Lys Asp Gln Asp
    370                 375                 380

Lys Ile Ser Ile Ala His Val Asp Asn Asp His Ile Val Phe Glu Gly
385                 390                 395                 400
```

Asp Gly Tyr His Tyr Gln Thr Tyr Asp Gln Trp Lys Glu Thr Asn Lys
                        405                 410                 415

Gly Ala Asp Asn Ile Ala Met Arg Asp Ala His Val Ile Asp Asp Asp
                420                 425                 430

Asn Gly Asn Arg Tyr Leu Val Phe Glu Ala Ser Thr Gly Thr Glu Asn
            435                 440                 445

Tyr Gln Gly Asp Gln Ile Tyr Gln Trp Leu Asn Tyr Gly Gly Thr
        450                 455                 460

Asn Lys Asp Asn Leu Gly Asp Phe Phe Gln Ile Leu Ser Asn Ser Asp
465                 470                 475                 480

Ile Lys Asp Arg Ala Lys Trp Ser Asn Ala Ile Gly Ile Ile Lys
                485                 490                 495

Leu Asn Asp Asp Val Lys Asn Pro Ser Val Ala Lys Val Tyr Ser Pro
                500                 505                 510

Leu Ile Ser Ala Pro Met Val Ser Asp Glu Ile Glu Arg Pro Asp Val
            515                 520                 525

Val Lys Leu Gly Asn Lys Tyr Tyr Leu Phe Ala Ala Thr Arg Leu Asn
        530                 535                 540

Arg Gly Ser Asn Asp Asp Ala Trp Met Ala Thr Asn Lys Ala Val Gly
545                 550                 555                 560

Asp Asn Val Ala Met Ile Gly Tyr Val Ser Asp Asn Leu Thr His Gly
                565                 570                 575

Tyr Val Pro Leu Asn Glu Ser Gly Val Val Leu Thr Ala Ser Val Pro
                580                 585                 590

Ala Asn Trp Arg Thr Ala Thr Tyr Ser Tyr Tyr Ala Val Pro Val Glu
            595                 600                 605

Gly Arg Asp Asp Gln Leu Leu Ile Thr Ser Tyr Ile Thr Asn Arg Gly
        610                 615                 620

Glu Val Ala Gly Lys Gly Met His Ala Thr Trp Ala Pro Ser Phe Leu
625                 630                 635                 640

Leu Gln Ile Asn Pro Asp Asn Thr Thr Thr Val Leu Ala Lys Met Thr
                645                 650                 655

Asn Gln Gly Asp Trp Ile Trp Asp Asp Ser Ser Glu Asn Pro Asp Met
            660                 665                 670

Met Gly Val Leu Glu Lys Asp Ala Pro Asn Ser Ala Ala Leu Pro Gly
        675                 680                 685

Glu Trp Gly Lys Pro Val Asp Trp Asp Leu Ile Gly Gly Tyr Asn Leu
        690                 695                 700

Lys Pro His Gln Pro Val Thr Pro Ile Pro Asn Val Pro Thr Thr Pro
705                 710                 715                 720

Glu Thr Pro Thr Thr Pro Asp Lys Pro Glu Val Pro Thr Thr Pro Glu
                725                 730                 735

Val Pro Thr Thr Pro Glu Thr Pro Thr Pro Glu Ala Pro Lys Asn Pro
            740                 745                 750

Val Lys Lys Thr Ser Gln Ser Lys Leu Pro Lys Ala Gly Asp Lys Asn
        755                 760                 765

Ser Phe Ala Ala Val Val Leu Gly Ala Val Ser Ser Ile Leu Gly Ala
        770                 775                 780

Val Gly Leu Thr Gly Val Ser Lys Arg Lys Arg Asn Asn
785                 790                 795

<210> SEQ ID NO 13
<211> LENGTH: 798
<212> TYPE: PRT

<213> ORGANISM: L. reuteri
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid

<400> SEQUENCE: 13

Met Leu Glu Arg Lys Glu His Lys Lys Met Tyr Lys Ser Gly Lys Asn
1               5                   10                  15

Trp Ala Val Val Thr Leu Ser Thr Ala Ala Leu Val Phe Gly Ala Thr
            20                  25                  30

Thr Val Asn Ala Ser Ala Asp Thr Asn Thr Glu Asn Asn Asp Ser Ser
        35                  40                  45

Thr Val His Val Thr Thr Gly Asp Asn Asp Ile Ala Val Lys Ser Ala
    50                  55                  60

Ile Leu Gly Ser Gly Gln Val Ser Ala Ala Ser Asp Ala Thr Ile Lys
65                  70                  75                  80

Asn Ser Ala Asn Ala Asn Ser Ala Ser Ser Ala Ala Asn Thr Gln Asn
                85                  90                  95

Ser Asn Ser Gln Val Ala Ser Ser Ala Ala Thr Thr Ser Ser Thr Ser
            100                 105                 110

Ser Ala Ala Ser Ser Asn Asn Thr Asp Ser Lys Ala Ala Gln Glu Asn
        115                 120                 125

Ala Asn Thr Ala Lys Asn Asp Asp Thr Gln Lys Ala Ala Pro Ala Asn
    130                 135                 140

Glu Ser Ser Glu Ala Lys Asn Glu Pro Ala Val Asn Val Asn Asp Ser
145                 150                 155                 160

Ser Ala Ala Lys Asn Asp Asp Gln Gln Ser Ser Lys Lys Asn Thr Thr
                165                 170                 175

Ala Lys Leu Asn Lys Asp Ala Glu Asn Val Val Lys Lys Ala Gly Ile
            180                 185                 190

Asp Pro Asn Ser Leu Thr Asp Asp Gln Ile Lys Ala Leu Asn Lys Met
        195                 200                 205

Asn Xaa Xaa Lys Ala Ala Lys Xaa Gly Thr Gln Met Thr Tyr Asn Asp
    210                 215                 220

Phe Gln Lys Xaa Ala Asp Thr Leu Ile Lys Gln Asp Gly Arg Tyr Thr
225                 230                 235                 240

Val Pro Phe Phe Lys Ala Ser Glu Ile Lys Asn Met Pro Ala Ala Thr
                245                 250                 255

Thr Lys Asp Ala Gln Thr Asn Thr Ile Glu Pro Leu Asp Val Trp Asp
            260                 265                 270

Ser Trp Pro Val Gln Asp Val Arg Thr Gly Gln Val Ala Asn Trp Asn
        275                 280                 285

Gly Tyr Gln Leu Val Ile Ala Met Met Gly Ile Pro Asn Gln Asn Asp
    290                 295                 300

Asn His Ile Tyr Leu Leu Tyr Asn Lys Tyr Gly Asp Asn Glu Leu Ser
305                 310                 315                 320

His Trp Lys Asn Ala Gly Pro Ile Phe Gly Tyr Asn Ser Thr Ala Val
                325                 330                 335

```
Ser Gln Glu Trp Ser Gly Ser Ala Val Leu Asn Ser Asp Asn Ser Ile
                340                 345                 350

Gln Leu Phe Tyr Thr Arg Val Asp Thr Ser Asp Asn Asn Thr Asn His
            355                 360                 365

Gln Lys Ile Ala Ser Ala Thr Leu Tyr Leu Thr Asp Asn Asn Gly Asn
        370                 375                 380

Val Ser Leu Ala Gln Val Ala Asn Asp His Ile Val Phe Glu Gly Asp
385                 390                 395                 400

Gly Tyr Tyr Tyr Gln Thr Tyr Asp Gln Trp Lys Ala Thr Asn Lys Gly
                405                 410                 415

Ala Asp Asn Ile Ala Met Arg Asp Ala His Val Ile Glu Asp Asp Asn
            420                 425                 430

Gly Asp Arg Tyr Leu Val Phe Glu Ala Ser Thr Gly Leu Glu Asn Tyr
        435                 440                 445

Gln Gly Glu Asn Gln Ile Tyr Asn Trp Leu Asn Tyr Gly Gly Asp Asp
    450                 455                 460

Ala Phe Asn Ile Lys Ser Leu Phe Arg Ile Leu Ser Asn Asp Asp Ile
465                 470                 475                 480

Lys Ser Arg Ala Thr Trp Ala Asn Ala Ala Ile Gly Ile Leu Lys Leu
                485                 490                 495

Asn Lys Asp Glu Lys Asn Pro Lys Val Ala Glu Leu Tyr Ser Pro Leu
            500                 505                 510

Ile Ser Ala Pro Met Val Ser Asp Glu Ile Glu Arg Pro Asn Val Val
        515                 520                 525

Lys Leu Gly Asn Lys Tyr Tyr Leu Phe Ala Ala Thr Arg Leu Asn Arg
    530                 535                 540

Gly Ser Asn Asp Asp Thr Trp Met Asn Ala Asn Tyr Ala Val Gly Asp
545                 550                 555                 560

Asn Val Ala Met Val Gly Tyr Val Ala Asp Ser Leu Thr Gly Ser Tyr
                565                 570                 575

Lys Pro Leu Asn Asp Ser Gly Val Val Leu Thr Ala Ser Val Pro Ala
            580                 585                 590

Asn Trp Arg Thr Ala Thr Tyr Ser Tyr Tyr Ala Val Pro Val Ala Gly
        595                 600                 605

Lys Asp Asp Gln Val Leu Val Thr Ser Tyr Met Thr Asn Arg Asn Gly
    610                 615                 620

Val Ala Gly Lys Gly Met Asp Ser Thr Trp Ala Pro Ser Phe Leu Leu
625                 630                 635                 640

Gln Ile Asn Gln Asp Asn Thr Thr Thr Val Leu Ala Lys Met Thr Asn
                645                 650                 655

Gln Gly Asp Trp Ile Trp Asp Asp Ser Ser Glu Asn Leu Asp Met Ile
            660                 665                 670

Gly Asp Leu Asp Ser Ala Ala Leu Pro Gly Glu Arg Asp Lys Pro Val
        675                 680                 685

Asp Trp Asp Leu Ile Gly Tyr Gly Leu Lys Pro His Asp Pro Ala Thr
    690                 695                 700

Pro Asn Asp Pro Glu Thr Pro Thr Thr Pro Glu Thr Pro Glu Thr Pro
705                 710                 715                 720

Asn Thr Pro Lys Thr Pro Lys Thr Pro Glu Asn Pro Gly Thr Pro Gln
                725                 730                 735

Thr Pro Asn Thr Pro Asn Thr Pro Glu Ile Pro Leu Thr Pro Glu Thr
            740                 745                 750

Pro Lys Gln Pro Glu Thr Gln Thr Asn Asn Arg Leu Pro Gln Thr Gly
```

```
                    755                 760                 765
Asn Asn Ala Asn Lys Ala Met Ile Gly Leu Gly Met Gly Thr Leu Leu
            770                 775                 780

Ser Met Phe Gly Leu Ala Gly Ile Asn Lys Arg Arg Phe Asn
785                 790                 795

<210> SEQ ID NO 14
<211> LENGTH: 798
<212> TYPE: PRT
<213> ORGANISM: L. reuteri

<400> SEQUENCE: 14

Met Leu Glu Arg Lys Glu His Lys Lys Met Tyr Lys Ser Gly Lys Asn
1               5                   10                  15

Trp Ala Val Val Thr Leu Ser Thr Ala Ala Leu Val Phe Gly Ala Thr
            20                  25                  30

Thr Val Asn Ala Ser Ala Asp Thr Asn Ile Glu Asn Asn Asp Ser Ser
        35                  40                  45

Thr Val Gln Val Thr Thr Gly Asp Asn Asp Ile Ala Val Lys Ser Val
    50                  55                  60

Thr Leu Gly Ser Gly Gln Val Ser Ala Ala Ser Asp Thr Thr Ile Arg
65                  70                  75                  80

Thr Ser Ala Asn Ala Asn Ser Ala Ser Ser Ala Ala Asn Thr Gln Asn
                85                  90                  95

Ser Asn Ser Gln Val Ala Ser Ser Ala Ala Ile Thr Ser Ser Thr Ser
            100                 105                 110

Ser Ala Ala Ser Ser Asn Asn Thr Asp Ser Lys Ala Ala Gln Glu Asn
        115                 120                 125

Thr Asn Thr Ala Lys Asn Asp Asp Thr Gln Lys Ala Ala Pro Ala Asn
    130                 135                 140

Glu Ser Ser Glu Ala Lys Asn Glu Pro Ala Val Asn Val Asn Asp Ser
145                 150                 155                 160

Ser Ala Ala Lys Asn Asp Asp Gln Gln Ser Ser Lys Lys Asn Thr Thr
                165                 170                 175

Ala Lys Leu Asn Lys Asp Ala Glu Asn Val Val Lys Lys Ala Gly Ile
            180                 185                 190

Asp Pro Asn Ser Leu Thr Asp Asp Gln Ile Lys Ala Leu Asn Lys Met
        195                 200                 205

Asn Phe Ser Lys Ala Ala Lys Ser Gly Thr Gln Met Thr Tyr Asn Asp
    210                 215                 220

Phe Gln Lys Ile Ala Asp Thr Leu Ile Lys Gln Asp Gly Arg Tyr Thr
225                 230                 235                 240

Val Pro Phe Phe Lys Ala Ser Glu Ile Lys Asn Met Pro Ala Ala Thr
                245                 250                 255

Thr Lys Asp Ala Gln Thr Asn Thr Ile Glu Pro Leu Asp Val Trp Asp
            260                 265                 270

Ser Trp Pro Val Gln Asp Val Arg Thr Gly Gln Val Ala Asn Trp Asn
        275                 280                 285

Gly Tyr Gln Leu Val Ile Ala Met Met Gly Ile Pro Asn Gln Asn Asp
    290                 295                 300

Asn His Ile Tyr Leu Leu Tyr Asn Lys Tyr Gly Asp Asn Glu Leu Ser
305                 310                 315                 320

His Trp Lys Asn Val Gly Pro Ile Phe Gly Tyr Asn Ser Thr Ala Val
                325                 330                 335
```

```
Ser Gln Glu Trp Ser Gly Ser Ala Val Leu Asn Ser Asp Asn Ser Ile
            340                 345                 350

Gln Leu Phe Tyr Thr Arg Val Asp Thr Ser Asp Asn Asn Thr Asn His
        355                 360                 365

Gln Lys Ile Ala Ser Ala Thr Leu Tyr Leu Thr Asp Asn Asn Gly Asn
    370                 375                 380

Val Ser Leu Ala Gln Val Ala Asn Asp His Ile Val Phe Glu Gly Asp
385                 390                 395                 400

Gly Tyr Tyr Tyr Gln Thr Tyr Asp Gln Trp Lys Ala Thr Asn Lys Gly
                405                 410                 415

Ala Asp Asn Ile Ala Met Arg Asp Ala His Val Ile Glu Asp Asp Asn
            420                 425                 430

Gly Asp Arg Tyr Leu Val Phe Glu Ala Ser Thr Gly Leu Glu Asn Tyr
        435                 440                 445

Gln Gly Glu Asp Gln Ile Tyr Asn Trp Leu Asn Tyr Gly Gly Asp Asp
    450                 455                 460

Ala Phe Asn Ile Lys Ser Leu Phe Arg Ile Leu Ser Asn Asp Asp Ile
465                 470                 475                 480

Lys Ser Arg Ala Thr Trp Ala Asn Ala Ala Ile Gly Ile Leu Lys Leu
                485                 490                 495

Asn Lys Asp Glu Lys Asn Pro Lys Val Ala Glu Leu Tyr Ser Pro Leu
            500                 505                 510

Ile Ser Ala Pro Met Val Ser Asp Glu Ile Glu Arg Pro Asn Val Val
        515                 520                 525

Lys Leu Gly Asn Lys Tyr Tyr Leu Phe Ala Ala Thr Arg Leu Asn Arg
    530                 535                 540

Gly Ser Asn Asp Asp Ala Trp Met Asn Ala Asn Tyr Ala Val Gly Asp
545                 550                 555                 560

Asn Val Ala Met Val Gly Tyr Val Ala Asp Ser Leu Thr Gly Ser Tyr
                565                 570                 575

Lys Pro Leu Asn Asp Ser Gly Val Val Leu Thr Ala Ser Val Pro Ala
            580                 585                 590

Asn Trp Arg Thr Ala Thr Tyr Ser Tyr Tyr Ala Val Pro Val Ala Gly
        595                 600                 605

Lys Asp Asp Gln Val Leu Val Thr Ser Tyr Met Thr Asn Arg Asn Gly
    610                 615                 620

Val Ala Gly Lys Gly Met Asp Ser Thr Trp Ala Pro Ser Phe Leu Leu
625                 630                 635                 640

Gln Ile Asn Pro Asp Asn Thr Thr Val Leu Ala Lys Met Thr Asn
                645                 650                 655

Gln Gly Asp Trp Ile Trp Asp Asp Ser Ser Glu Asn Leu Asp Met Ile
            660                 665                 670

Gly Asp Leu Asp Ser Ala Ala Leu Pro Gly Glu Arg Asp Lys Pro Val
        675                 680                 685

Asp Trp Asp Leu Ile Gly Tyr Gly Leu Lys Pro His Asp Pro Ala Thr
    690                 695                 700

Pro Asn Asp Pro Glu Thr Pro Thr Pro Glu Thr Pro Glu Thr Pro
705                 710                 715                 720

Asn Thr Pro Lys Thr Pro Lys Thr Pro Glu Asn Pro Gly Thr Pro Gln
                725                 730                 735

Thr Pro Asn Thr Pro Asn Thr Pro Glu Ile Pro Leu Thr Pro Glu Thr
            740                 745                 750

Pro Lys Gln Pro Glu Thr Gln Thr Asn Asn Arg Leu Pro Gln Thr Gly
```

```
                  755                 760                 765
Asn Asn Ala Asn Lys Ala Met Ile Gly Leu Gly Met Gly Thr Leu Leu
        770                 775                 780

Ser Met Phe Gly Leu Ala Glu Ile Asn Lys Arg Arg Phe Asn
785                 790                 795

<210> SEQ ID NO 15
<211> LENGTH: 804
<212> TYPE: PRT
<213> ORGANISM: L. reuteri

<400> SEQUENCE: 15

Met Glu Tyr Lys Glu His Lys Lys Met Tyr Lys Val Gly Lys Asn Trp
1               5                   10                  15

Ala Val Ala Thr Leu Val Ser Ala Ser Ile Leu Met Gly Gly Val Val
            20                  25                  30

Thr Ala His Ala Asp Gln Val Glu Ser Asn Asn Tyr Asn Gly Val Ala
        35                  40                  45

Glu Val Asn Thr Glu Arg Gln Ala Asn Gly Gln Ile Gly Val Asp Gly
    50                  55                  60

Lys Ile Ile Ser Ala Asn Ser Asn Thr Thr Ser Gly Ser Thr Asn Gln
65                  70                  75                  80

Glu Ser Ser Ala Thr Asn Asn Thr Glu Asn Ala Val Val Asn Glu Ser
                85                  90                  95

Lys Asn Thr Asn Asn Thr Glu Asn Ala Val Val Asn Glu Asn Lys Asn
            100                 105                 110

Thr Asn Asn Thr Glu Asn Ala Val Val Asn Glu Asn Lys Asn Thr Asn
        115                 120                 125

Asn Thr Glu Asn Asp Asn Ser Gln Leu Lys Leu Thr Asn Asn Glu Gln
    130                 135                 140

Pro Ser Ala Ala Thr Gln Ala Asn Leu Lys Lys Leu Asn Pro Gln Ala
145                 150                 155                 160

Ala Lys Ala Val Gln Asn Ala Lys Ile Asp Ala Gly Ser Leu Thr Asp
                165                 170                 175

Asp Gln Ile Asn Glu Leu Asn Lys Ile Asn Phe Ser Lys Ser Ala Glu
            180                 185                 190

Lys Gly Ala Lys Leu Thr Phe Lys Asp Leu Glu Gly Ile Gly Asn Ala
        195                 200                 205

Ile Val Lys Gln Asp Pro Gln Tyr Ala Ile Pro Tyr Phe Asn Ala Lys
    210                 215                 220

Glu Ile Lys Asn Met Pro Ala Thr Tyr Thr Val Asp Ala Gln Thr Gly
225                 230                 235                 240

Lys Met Ala His Leu Asp Val Trp Asp Ser Trp Pro Val Gln Asp Pro
                245                 250                 255

Val Thr Gly Tyr Val Ser Asn Tyr Lys Gly Tyr Gln Leu Val Ile Ala
            260                 265                 270

Met Met Gly Ile Pro Asn Ser Pro Thr Gly Asp Asn His Ile Tyr Leu
        275                 280                 285

Leu Tyr Asn Lys Tyr Gly Asp Asn Asp Phe Ser His Trp Arg Asn Ala
    290                 295                 300

Gly Ser Ile Phe Gly Thr Lys Glu Thr Asn Val Phe Gln Glu Trp Ser
305                 310                 315                 320

Gly Ser Ala Ile Val Asn Asp Asp Gly Thr Ile Gln Leu Phe Phe Thr
                325                 330                 335
```

```
Ser Asn Asp Thr Ser Asp Tyr Lys Leu Asn Asp Gln Arg Leu Ala Thr
            340                 345                 350

Ala Thr Leu Asn Leu Asn Val Asp Asp Asn Gly Val Ser Ile Lys Ser
        355                 360                 365

Val Asp Asn Tyr Gln Val Leu Phe Glu Gly Asp Gly Phe His Tyr Gln
    370                 375                 380

Thr Tyr Glu Gln Phe Ala Asn Gly Lys Asp Arg Glu Asn Asp Asp Tyr
385                 390                 395                 400

Cys Leu Arg Asp Pro His Val Val Gln Leu Glu Asn Gly Asp Arg Tyr
                405                 410                 415

Leu Val Phe Glu Ala Asn Thr Gly Thr Glu Asp Tyr Gln Ser Asp Asp
            420                 425                 430

Gln Ile Tyr Asn Trp Ala Asn Tyr Gly Gly Asp Asp Ala Phe Asn Ile
        435                 440                 445

Lys Ser Phe Phe Lys Leu Leu Asn Asn Lys Lys Asp Arg Glu Leu Ala
    450                 455                 460

Gly Leu Ala Asn Gly Ala Leu Gly Ile Leu Lys Leu Thr Asn Asn Gln
465                 470                 475                 480

Ser Lys Pro Lys Val Glu Glu Val Tyr Ser Pro Leu Val Ser Thr Leu
                485                 490                 495

Met Ala Ser Asp Glu Val Glu Arg Pro Asn Val Val Lys Leu Gly Asp
            500                 505                 510

Lys Tyr Tyr Leu Phe Ser Val Thr Arg Val Ser Arg Gly Ser Asp Arg
        515                 520                 525

Glu Leu Thr Ala Lys Asp Asn Thr Ile Val Gly Asp Asn Val Ala Met
    530                 535                 540

Ile Gly Tyr Val Ser Asp Ser Leu Met Gly Lys Tyr Lys Pro Leu Asn
545                 550                 555                 560

Asn Ser Gly Val Val Leu Thr Ala Ser Val Pro Ala Asn Trp Arg Thr
                565                 570                 575

Ala Thr Tyr Ser Tyr Tyr Ala Val Pro Val Ala Gly His Pro Asp Gln
            580                 585                 590

Val Leu Ile Thr Ser Tyr Met Ser Asn Lys Asp Phe Ala Ser Gly Glu
        595                 600                 605

Gly Asn Tyr Ala Thr Trp Ala Pro Ser Phe Leu Val Gln Ile Asn Pro
    610                 615                 620

Asp Asp Thr Thr Thr Val Leu Ala Arg Ala Thr Asn Gln Gly Asp Trp
625                 630                 635                 640

Val Trp Asp Asp Ser Ser Arg Asn Asp Asn Met Leu Gly Val Leu Lys
                645                 650                 655

Glu Gly Ala Ala Asn Ser Ala Ala Leu Pro Gly Glu Trp Gly Lys Pro
            660                 665                 670

Val Asp Trp Ser Leu Ile Asn Arg Ser Ser Gly Leu Gly Leu Lys Pro
        675                 680                 685

His Gln Pro Val Gln Pro Lys Ile Asp Gln Pro Asp Gln Gln Pro Ser
    690                 695                 700

Gly Gln Asn Thr Lys Asn Val Thr Pro Gly Asn Gly Asp Lys Pro Ala
705                 710                 715                 720

Gly Lys Ala Thr Pro Asp Asn Thr Asn Ile Asp Pro Ser Ala Gln Pro
                725                 730                 735

Ser Gly Gln Asn Thr Asn Ile Asp Pro Ser Ala Gln Pro Ser Gly Gln
            740                 745                 750

Asn Thr Lys Asn Val Thr Pro Gly Asn Glu Lys Gln Gly Lys Asn Thr
```

```
                    755                 760                 765
Asp Ala Lys Gln Leu Pro Gln Thr Gly Asn Lys Ser Gly Leu Ala Gly
770                 775                 780

Leu Tyr Ala Gly Ser Leu Ala Leu Phe Gly Leu Ala Ala Ile Glu
785                 790                 795                 800

Lys Arg His Ala

<210> SEQ ID NO 16
<211> LENGTH: 797
<212> TYPE: PRT
<213> ORGANISM: S. mutans

<400> SEQUENCE: 16

Met Glu Thr Lys Val Arg Lys Lys Met Tyr Lys Lys Gly Lys Phe Trp
1               5                   10                  15

Val Val Ala Thr Ile Thr Thr Ala Met Leu Thr Gly Ile Gly Leu Ser
                20                  25                  30

Ser Val Gln Ala Asp Glu Ala Asn Ser Thr Gln Val Ser Ser Glu Leu
            35                  40                  45

Ala Glu Arg Ser Gln Val Gln Glu Asn Thr Thr Ala Ser Ser Ser Ala
        50                  55                  60

Ala Glu Asn Gln Ala Lys Thr Glu Val Gln Glu Thr Pro Ser Thr Asn
65                  70                  75                  80

Pro Ala Ala Thr Val Glu Asn Thr Asp Gln Thr Thr Lys Val Ile
                85                  90                  95

Thr Asp Asn Ala Ala Val Glu Ser Lys Ala Ser Lys Thr Lys Asp Gln
                100                 105                 110

Ala Ala Thr Val Thr Lys Thr Ala Ala Ser Thr Pro Glu Val Gly Gln
            115                 120                 125

Thr Asn Glu Lys Asp Lys Ala Lys Ala Thr Lys Glu Ala Asp Ile Thr
130                 135                 140

Thr Pro Lys Asn Thr Ile Asp Glu Tyr Gly Leu Thr Glu Gln Ala Arg
145                 150                 155                 160

Lys Ile Ala Thr Glu Ala Gly Ile Asn Leu Ser Ser Leu Thr Gln Lys
                165                 170                 175

Gln Val Glu Ala Leu Asn Lys Val Lys Leu Thr Ser Asp Ala Gln Thr
            180                 185                 190

Gly His Gln Met Thr Tyr Gln Glu Phe Asp Lys Ile Ala Gln Thr Leu
        195                 200                 205

Ile Ala Gln Asp Glu Arg Tyr Ala Ile Pro Tyr Phe Asn Ala Lys Ala
210                 215                 220

Ile Lys Asn Met Lys Ala Ala Thr Thr Arg Asp Ala Gln Thr Gly Gln
225                 230                 235                 240

Ile Ala Asp Leu Asp Val Trp Asp Ser Trp Pro Val Gln Asp Ala Lys
                245                 250                 255

Thr Gly Glu Val Ile Asn Trp Asn Gly Tyr Gln Leu Val Val Ala Met
            260                 265                 270

Met Gly Ile Pro Asn Thr Asn Asp Asn His Ile Tyr Leu Leu Tyr Asn
        275                 280                 285

Lys Tyr Gly Asp Asn Asn Phe Asp His Trp Lys Asn Ala Gly Ser Ile
290                 295                 300

Phe Gly Tyr Asn Glu Thr Pro Leu Thr Gln Glu Trp Ser Gly Ser Ala
305                 310                 315                 320

Thr Val Asn Glu Asp Gly Ser Leu Gln Leu Phe Tyr Thr Lys Val Asp
```

```
                    325                 330                 335
Thr Ser Asp Lys Asn Ser Asn Asn Gln Arg Leu Ala Thr Ala Thr Val
                340                 345                 350
Asn Leu Gly Phe Asp Asp Gln Asp Val Arg Ile Leu Ser Val Glu Asn
                355                 360                 365
Asp Lys Val Leu Thr Pro Glu Gly Val Met Ala Tyr His Tyr Gln Ser
370                 375                 380
Tyr Gln Gln Trp Arg Ser Thr Phe Thr Gly Ala Asp Asn Ile Ala Met
385                 390                 395                 400
Arg Asp Pro His Val Ile Glu Asp Asn Gly Asp Arg Tyr Leu Val
                405                 410                 415
Phe Glu Ala Ser Thr Gly Thr Glu Asn Tyr Gln Gly Glu Asp Gln Ile
                420                 425                 430
Tyr Asn Phe Thr Asn Tyr Gly Gly Ser Ala Tyr Asn Val Lys Ser
                435                 440                 445
Leu Phe Arg Phe Leu Asp Asp Gln Asp Met Tyr Asn Arg Ala Ser Trp
                450                 455                 460
Ala Asn Ala Ala Ile Gly Ile Leu Lys Leu Lys Gly Asp Lys Lys Thr
465                 470                 475                 480
Pro Glu Val Asp Gln Phe Tyr Thr Pro Leu Leu Ser Ser Thr Met Val
                485                 490                 495
Ser Asp Glu Leu Glu Arg Pro Asn Val Val Lys Leu Gly Asp Lys Tyr
                500                 505                 510
Tyr Leu Phe Thr Ala Ser Arg Leu Asn His Gly Ser Asn Asn Asp Ala
                515                 520                 525
Trp Asn Lys Ala Asn Glu Val Val Gly Asp Asn Val Val Met Leu Gly
                530                 535                 540
Tyr Val Ser Asp Gln Leu Thr Asn Gly Tyr Lys Pro Leu Asn Asn Ser
545                 550                 555                 560
Gly Val Val Leu Thr Ala Ser Val Pro Ala Asp Trp Arg Thr Ala Thr
                565                 570                 575
Tyr Ser Tyr Tyr Ala Val Pro Val Ala Gly Ser Ser Asp Thr Leu Leu
                580                 585                 590
Met Thr Ala Tyr Met Thr Asn Arg Asn Glu Val Ala Gly Lys Gly Lys
                595                 600                 605
Asn Ser Thr Trp Ala Pro Ser Phe Leu Ile Gln Val Leu Pro Asp Gly
                610                 615                 620
Thr Thr Lys Val Leu Ala Glu Met Thr Gln Gln Gly Asp Trp Ile Trp
625                 630                 635                 640
Asp Glu Pro Ser Arg Thr Thr Asp Thr Val Gly Thr Leu Asp Thr Ala
                645                 650                 655
Tyr Leu Pro Gly Glu Asn Asp Gly Tyr Ile Asp Trp Asn Val Ile Gly
                660                 665                 670
Gly Tyr Gly Leu Lys Pro His Thr Pro Gly Gln Tyr Gln Pro Thr Val
                675                 680                 685
Pro Ser Thr Pro Ile His Thr Asp Asp Ile Ile Ser Phe Glu Val Ser
                690                 695                 700
Phe Asp Gly His Leu Val Ile Lys Pro Val Lys Val Asn Asn Asp Ser
705                 710                 715                 720
Ala Gly Arg Ile Asp Gln Ser Arg Asn Ser Gly Gly Ser Leu Asn Val
                725                 730                 735
Ala Phe Asn Val Ser Ala Gly Gly Asn Ile Ser Val Lys Pro Ser Gln
                740                 745                 750
```

```
Lys Ser Ile Asn Asn Thr Lys Glu Thr Lys Ala His His Val Ser
            755                 760                 765

Thr Glu Lys Lys Gln Lys Lys Gly Asn Ser Phe Phe Ala Ala Leu Leu
    770             775                 780

Ala Leu Phe Ser Ala Phe Cys Val Ser Ile Gly Phe Lys
785                 790                 795

<210> SEQ ID NO 17
<211> LENGTH: 1490
<212> TYPE: PRT
<213> ORGANISM: L. mesenteroides

<400> SEQUENCE: 17

Met Lys Gln Gln Glu Ser Met Ala Arg Lys Lys Leu Tyr Lys Ala Gly
1               5                   10                  15

Lys Ile Trp Val Ala Ala Ala Thr Val Ser Ala Val Ile Gly Val Ser
                20                  25                  30

Ala Ile Thr Asn Val Ser Ala Asp Val Asn Gln Pro Leu Leu Ala Gln
            35                  40                  45

Glu Asn Phe Ser Gly Asn Lys Thr Glu Pro Val Pro Asp Lys Ser Asn
    50                  55                  60

Lys Asn Glu Ser Val Lys Asp Ser Lys Val Ala Thr Ser Asp Glu Leu
65                  70                  75                  80

Ala Lys Asp Ser Lys Val Ala Thr Ser Asp Glu Leu Ala Lys Asp Ser
                85                  90                  95

Lys Val Ala Thr Ser Asp Glu Leu Ala Lys Asp Ser Lys Val Ala Thr
            100                 105                 110

Ser Asp Glu Leu Val Lys Asp Ser Lys Val Ala Thr Ser Asp Glu Leu
    115                 120                 125

Ala Lys Asp Ser Lys Val Ala Thr Ser Asp Glu Leu Ala Lys Asp Ser
130                 135                 140

Lys Val Ala Thr Ser Asp Glu Leu Ala Lys Asp Ser Lys Val Ala Thr
145                 150                 155                 160

Ser Asp Glu Leu Ala Lys Asp Ser Lys Val Ala Thr Ser Asp Glu Leu
                165                 170                 175

Ala Lys Asp Ser Lys Ala Pro Thr Asn Asp Val Ser Val Arg Ala Glu
            180                 185                 190

Lys Lys Ser Ser Leu Ile Asp Ser Pro Glu Leu Asn Val Lys Met Ser
    195                 200                 205

Glu Met Thr Ser Val Pro Asn Leu Ile Ser Asp Glu Asn Ser Lys Asn
    210                 215                 220

Leu Val Asn Ser Asn Glu Leu Ile Asn Gly Leu Ser Lys Arg Ser Leu
225                 230                 235                 240

Glu Ile Ala His Gln Ala Gly Ile Asp Val Ser Arg Leu Asn Asp Ile
                245                 250                 255

Gln Lys Ala Ala Leu Asn Lys Ile Lys Leu Val Asn Glu Asp Gly Asn
            260                 265                 270

Lys Tyr Val Leu Asp Asn Thr Gly Ser Asp Tyr Thr Lys Asn Thr Ile
    275                 280                 285

Ile Asp Lys Asn Asn Pro Asp Asp Thr Thr Lys Thr Thr His Ile Thr
    290                 295                 300

Phe Ala Asn Leu Asp Asp Ala Ile Lys Leu Ala Gln Lys Pro Asp Pro
305                 310                 315                 320

Lys Thr Thr Ile Pro Val Phe Asn Ala Ser Gln Ile Asn Asn Leu Pro
```

```
                        325                 330                 335
Ala Ser Ile Phe Lys Asp Ala Gln Thr Asn Lys Val Glu Lys Met Asp
                340                 345                 350

Val Trp Asp Ser Trp Ala Leu Gln Asp Ser Lys Thr Gly Glu Val Tyr
                355                 360                 365

Asn Tyr His Gly Lys Gln Val Val Phe Ala Leu Met Gly Ala Pro Leu
                370                 375                 380

Val Gln Gly Asp Thr His Ile Tyr Met Leu Tyr Asn Asn Tyr Asn Asn
385                 390                 395                 400

Ala Lys Leu Asp Gly Trp Val Asn Ala Gly Pro Val Phe Gly Tyr Asn
                405                 410                 415

Ala Lys Pro Glu Ser Gln Glu Trp Ser Gly Ser Ala Val Val Asn Ser
                420                 425                 430

Asp Asp Ser Ile Gln Leu Phe Tyr Thr Arg Val Ala Asp Asp Trp Lys
                435                 440                 445

Gln Ala Leu Ala Thr Val Asn Ile Lys Ile Thr Asn Ser Glu Asn Ser
                450                 455                 460

Leu Gly Ile Gln Ser Leu Gln Asn Asp His Ile Leu Phe Glu Gly Asp
465                 470                 475                 480

Gly Tyr Phe Tyr Ser Arg Lys Asp Gln Leu Lys Pro Gln Ala Asp Met
                485                 490                 495

Phe Thr Leu Arg Asp Pro Lys Leu Ile Glu Leu Asp Asp Gly Glu Arg
                500                 505                 510

Tyr Leu Thr Phe Glu Ala Asn Thr Gly Ile Tyr Asp Glu Ala Ser Asp
                515                 520                 525

Gln Gln Thr Val Asn Leu Asn Asn Tyr Gly Gly Leu Thr Tyr Asp
                530                 535                 540

Val Ala Arg Met Leu Gly Val Val Asn Asn Ser Asn Arg Ala Leu Tyr
545                 550                 555                 560

Ser Ser Thr Ala Asn Gly Ala Ile Gly Leu Leu Lys Leu Lys Gly Asp
                565                 570                 575

Tyr Phe Asn Pro Ile Leu Asp Arg Leu Tyr Lys Pro Leu Ile Thr Ala
                580                 585                 590

Val Gly Val Thr Asp Glu Ile Glu Arg Ala Asn Ile Val Pro Phe Asn
                595                 600                 605

Gly Lys Tyr Tyr Leu Phe Thr Asp Ser Arg Phe Asn Arg Ser Ala Ala
                610                 615                 620

Asp Asn Ser Pro Met Ser Met Ala Pro Asp Gly Ala Met Met Met Gly
625                 630                 635                 640

Phe Val Ser Asp Ser Leu Phe Gly Asp Tyr Lys Pro Leu Asn Gly Asn
                645                 650                 655

Gly Ile Val Leu Val Thr Asn Asn Ser Phe Thr Ser Arg Thr Asn Thr
                660                 665                 670

Tyr Ser Trp Tyr Thr Val Pro Val Lys Gly Arg Pro Asp Leu Met Leu
                675                 680                 685

Val Thr Ser Tyr Met Thr Asn Arg Gly Leu Ala Ser Gly Thr Asp Gln
                690                 695                 700

Tyr Ser Thr Phe Ala Pro Ser Phe Leu Leu Lys Ile Asp Gly Asp Gln
705                 710                 715                 720

Thr His Val Leu Asn Thr Val Thr Glu Gln Gly Asp Trp Val Trp Gly
                725                 730                 735

Asp Asp Asp His Ser Ile Val Glu Leu Leu Ala Leu Asn Thr Glu Asp
                740                 745                 750
```

```
Ala Tyr Leu Thr Asn Asn Gln Lys Asn Ile Asn Tyr Ser Pro Asp Trp
        755                 760                 765

Ser Asn Ile Asp Gly Tyr Gly Tyr Pro Ile Val Thr Asn Ile Lys Asp
    770                 775                 780

Val Asp Leu Thr Phe Tyr Ile Ser Gly Ile Leu Ser Pro Asp Ser Leu
785                 790                 795                 800

Phe Lys Asn Ala Pro Gly Arg His Gln Gly Ala Arg Ile Ile Gly Ser
                805                 810                 815

Thr Ser Gln Tyr Asn Thr Glu Lys Val Ser Ala Ile Lys Glu Tyr Thr
                820                 825                 830

Asp Asp Leu Asn Thr Ile Trp Tyr Leu Val Asn Leu Ala Gly Asn Asn
                835                 840                 845

Phe Trp Ile Lys Gly Ser Ser Leu Val Thr Val Pro Met Thr Asp Ser
        850                 855                 860

Thr Phe Arg Asn Ala Tyr Ile Val Lys Asp Ser Asp Met Tyr Leu Asp
865                 870                 875                 880

Ala Pro Gln Gly Glu Thr Asn Ala Lys Tyr Tyr Gln Ser Ser Asn Ser
                885                 890                 895

Tyr Asn Asp Ala Tyr Val Ile Val Gly Gly Glu Tyr Lys Asp Ala His
                900                 905                 910

Gly Ile Thr Trp Asn Leu Ile Lys Leu Asn Asp Lys Ile Leu Trp Ile
                915                 920                 925

Asn Lys Asn Ser Leu Ala Ile Ser Phe Ser Arg Asp Leu Asn Ala Lys
            930                 935                 940

Ala Phe Val Asn Ala Thr Ser Arg Asn Asp Gly Leu Phe Leu Asn Ala
945                 950                 955                 960

Pro Tyr Arg Gln Val Gly Ser Glu Leu Val Gly Phe Thr Lys Lys Tyr
                965                 970                 975

Asn Gly Gln Ile Val Ala Ile Asp Lys Gln Phe Phe Asp Lys Gly
                980                 985                 990

Ile Ile Trp Ser Gln Val Ile Ile Asp Gly Gln Lys Phe Trp Val Asp
        995                 1000                1005

Asn Arg Gly Leu Asn Gln Val Gln Thr Gln Asp Val Asn Lys Lys
    1010                1015                1020

Leu Tyr Val Asn Ser Ala Ser Gln Ser Asp Gly Leu Phe Leu Asn
    1025                1030                1035

Ala Pro Tyr Arg Gly Ile Asn Ala Lys Leu Val Ala Met Ala Lys
    1040                1045                1050

Thr Tyr Asn Gly Arg Tyr Val Asn Val Leu Lys Gln Gly Lys Asp
    1055                1060                1065

Ala Tyr Asn Val Asn Trp Ser Leu Ile Glu Leu Asp Gly Gln Ser
    1070                1075                1080

Leu Trp Ile Asp Ser Gln Ala Leu Asn Thr Asn Phe Thr His Asp
    1085                1090                1095

Met Asn Gln Lys Val Phe Val Asn Thr Thr Ser Asn Leu Asp Gly
    1100                1105                1110

Leu Phe Leu Asn Ala Pro Tyr Arg Gln Pro Gly Tyr Lys Leu Ala
    1115                1120                1125

Gly Leu Ala Lys Asn Tyr Asn Asn Gln Thr Val Thr Val Ser Gln
    1130                1135                1140

Gln Tyr Phe Asp Asp Gln Gly Thr Gly Trp Ser Glu Val Val Leu
    1145                1150                1155
```

Gly Gly Gln Thr Val Trp Val Asp Asn His Ala Leu Ala Gln Met
    1160                1165                1170

Gln Val Ser Asp Thr Ser Gln Leu Tyr Val Asn Ser Asn Gly
    1175                1180                1185

Arg Asn Asp Gly Leu Phe Leu Asn Ala Pro Tyr Arg Gly Gln Gly
    1190                1195                1200

Ser Gln Leu Ile Gly Met Thr Ala Asp Tyr Asn Gly Gln His Val
    1205                1210                1215

Gln Val Thr Lys Gln Gly Gln Asp Ala Tyr Gly Ala Gln Trp Arg
    1220                1225                1230

Leu Ile Thr Leu Asn Asn Gln Gln Val Trp Val Asp Ser Arg Ala
    1235                1240                1245

Leu Ser Thr Thr Ile Met Gln Ala Met Asn Asp Met Tyr Val
    1250                1255                1260

Asn Ser Asn Gln Arg Thr Asp Gly Leu Trp Leu Asn Ala Pro Tyr
    1265                1270                1275

Thr Met Ser Gly Ala Lys Trp Ala Gly Asp Thr Arg Leu Ala Asn
    1280                1285                1290

Gly Arg Tyr Val His Ile Ser Lys Ala Tyr Ser Asn Glu Val Gly
    1295                1300                1305

Asn Thr Tyr Tyr Leu Thr Asn Leu Asn Gly Gln Ser Thr Trp Ile
    1310                1315                1320

Asp Lys Arg Ala Phe Thr Ala Thr Phe Asp Gln Val Val Ala Leu
    1325                1330                1335

Asn Ala Thr Ile Val Ala Arg Gln Arg Pro Asp Gly Met Phe Lys
    1340                1345                1350

Thr Ala Pro Ile Trp Glu Ala Gly Ala Gln Phe Val Asp Tyr Val
    1355                1360                1365

Thr Asn Tyr Asn Gln Gln Thr Val Pro Val Thr Lys Gln His Ser
    1370                1375                1380

Asp Ala Gln Gly Asn Gln Trp Tyr Leu Ala Thr Val Asn Gly Thr
    1385                1390                1395

Gln Tyr Trp Ile Asp Gln Arg Ser Phe Ser Pro Val Val Thr Lys
    1400                1405                1410

Val Val Asp Tyr Gln Ala Lys Ile Val Pro Arg Thr Thr Arg Asp
    1415                1420                1425

Gly Val Phe Ser Gly Ala Pro Tyr Gly Glu Val Asn Ala Lys Leu
    1430                1435                1440

Val Asn Met Ala Thr Ala Tyr Gln Asn Gly Val Val His Ala Thr
    1445                1450                1455

Gly Glu Tyr Thr Asn Ala Ser Gly Ile Thr Trp Ser Gln Phe Ala
    1460                1465                1470

Leu Ser Gly Gln Glu Asp Lys Leu Trp Ile Asp Lys Arg Ala Leu
    1475                1480                1485

Gln Ala
    1490

<210> SEQ ID NO 18
<211> LENGTH: 423
<212> TYPE: PRT
<213> ORGANISM: Z. mobilis

<400> SEQUENCE: 18

Met Leu Asn Lys Ala Gly Ile Ala Glu Pro Ser Leu Trp Thr Arg Ala
1               5                   10                  15

```
Asp Ala Met Lys Val His Thr Asp Asp Pro Thr Ala Thr Met Pro Thr
             20                  25                  30

Ile Asp Tyr Asp Phe Pro Val Met Thr Asp Lys Tyr Trp Val Trp Asp
         35                  40                  45

Thr Trp Pro Leu Arg Asp Ile Asn Gly Gln Val Val Ser Phe Gln Gly
 50                  55                  60

Trp Ser Val Ile Phe Ala Leu Val Ala Asp Arg Thr Lys Tyr Gly Trp
 65                  70                  75                  80

His Asn Arg Asn Asp Gly Ala Arg Ile Gly Tyr Phe Tyr Ser Arg Gly
                 85                  90                  95

Gly Ser Asn Trp Ile Phe Gly Gly His Leu Leu Lys Asp Gly Ala Asn
                100                 105                 110

Pro Arg Ser Trp Glu Trp Ser Gly Cys Thr Ile Met Ala Pro Gly Thr
             115                 120                 125

Ala Asn Ser Val Glu Val Phe Phe Thr Ser Val Asn Asp Thr Pro Ser
 130                 135                 140

Glu Ser Val Pro Ala Gln Cys Lys Gly Tyr Ile Tyr Ala Asp Asp Lys
145                 150                 155                 160

Ser Val Trp Phe Asp Gly Phe Asp Lys Val Thr Asp Leu Phe Gln Ala
                 165                 170                 175

Asp Gly Leu Tyr Tyr Ala Asp Tyr Ala Glu Asn Asn Phe Trp Asp Phe
             180                 185                 190

Arg Asp Pro His Val Phe Ile Thr Pro Lys Ile Gly Lys Thr Tyr Ala
             195                 200                 205

Leu Phe Glu Gly Asn Val Ala Met Glu Arg Gly Thr Val Ala Val Gly
         210                 215                 220

Glu Glu Glu Ile Gly Pro Val Pro Pro Lys Thr Glu Thr Pro Asp Gly
225                 230                 235                 240

Ala Arg Tyr Cys Ala Ala Ile Gly Ile Ala Gln Ala Leu Asn Glu
             245                 250                 255

Ala Arg Thr Glu Trp Lys Leu Leu Pro Pro Leu Val Thr Ala Phe Gly
             260                 265                 270

Val Asn Asp Gln Thr Glu Arg Pro His Val Val Phe Gln Asn Gly Leu
         275                 280                 285

Thr Tyr Leu Phe Thr Ile Ser His His Ser Thr Tyr Ala Asp Gly Leu
 290                 295                 300

Ser Gly Pro Asp Gly Val Tyr Gly Phe Val Ser Glu Asn Gly Ile Phe
305                 310                 315                 320

Gly Pro Tyr Glu Pro Leu Asn Gly Ser Gly Leu Val Leu Gly Asn Pro
             325                 330                 335

Ser Ser Gln Pro Tyr Gln Ala Tyr Ser His Tyr Val Met Thr Asn Gly
             340                 345                 350

Leu Val Thr Ser Phe Ile Asp Thr Ile Pro Ser Ser Asp Pro Asn Val
             355                 360                 365

Tyr Arg Tyr Gly Gly Thr Leu Ala Pro Thr Ile Lys Leu Glu Leu Val
             370                 375                 380

Gly His Arg Ser Phe Val Thr Glu Val Lys Gly Tyr Gly Tyr Ile Pro
385                 390                 395                 400

Pro Gln Ile Glu Trp Leu Ala Glu Asp Glu Ser Ser Asn Ser Ala Ala
             405                 410                 415

Ala Leu Ser Leu Leu Asn Lys
             420
```

<210> SEQ ID NO 19
<211> LENGTH: 584
<212> TYPE: PRT
<213> ORGANISM: G. diazotrophicus

<400> SEQUENCE: 19

```
Met Ala His Val Arg Arg Lys Val Ala Thr Leu Asn Met Ala Leu Ala
1               5                   10                  15

Gly Ser Leu Leu Met Val Leu Gly Ala Gln Ser Ala Leu Ala Gln Gly
            20                  25                  30

Asn Phe Ser Arg Gln Glu Ala Ala Arg Met Ala His Arg Pro Gly Val
        35                  40                  45

Met Pro Arg Gly Gly Pro Leu Phe Pro Gly Arg Ser Leu Ala Gly Val
    50                  55                  60

Pro Gly Phe Pro Leu Pro Ser Ile His Thr Gln Gln Ala Tyr Asp Pro
65                  70                  75                  80

Gln Ser Asp Phe Thr Ala Arg Trp Thr Arg Ala Asp Ala Leu Gln Ile
                85                  90                  95

Lys Ala His Ser Asp Ala Thr Val Ala Ala Gly Gln Asn Ser Leu Pro
            100                 105                 110

Ala Gln Leu Thr Met Pro Asn Ile Pro Ala Asp Phe Pro Val Ile Asn
        115                 120                 125

Pro Asp Val Trp Val Trp Asp Thr Trp Thr Leu Ile Asp Lys His Ala
130                 135                 140

Asp Gln Phe Ser Tyr Asn Gly Trp Glu Val Ile Phe Cys Leu Thr Ala
145                 150                 155                 160

Asp Pro Asn Ala Gly Tyr Gly Phe Asp Asp Arg His Val His Ala Arg
                165                 170                 175

Ile Gly Phe Phe Tyr Arg Arg Ala Gly Ile Pro Ala Ser Arg Arg Pro
            180                 185                 190

Val Asn Gly Gly Trp Thr Tyr Gly Gly His Leu Phe Pro Asp Gly Ala
        195                 200                 205

Ser Ala Gln Val Tyr Ala Gly Gln Thr Tyr Thr Asn Gln Ala Glu Trp
    210                 215                 220

Ser Gly Ser Ser Arg Leu Met Gln Ile His Gly Asn Thr Val Ser Val
225                 230                 235                 240

Phe Tyr Thr Asp Val Ala Phe Asn Arg Asp Ala Asn Ala Asn Asn Ile
                245                 250                 255

Thr Pro Pro Gln Ala Ile Ile Thr Gln Thr Leu Gly Arg Ile His Ala
            260                 265                 270

Asp Phe Asn His Val Trp Phe Thr Gly Phe Thr Ala His Thr Pro Leu
        275                 280                 285

Leu Gln Pro Asp Gly Val Leu Tyr Gln Asn Gly Ala Gln Asn Glu Phe
    290                 295                 300

Phe Asn Phe Arg Asp Pro Phe Thr Phe Glu Asp Pro Lys His Pro Gly
305                 310                 315                 320

Val Asn Tyr Met Val Phe Glu Gly Asn Thr Ala Gly Gln Arg Gly Val
                325                 330                 335

Ala Asn Cys Thr Glu Ala Asp Leu Gly Phe Arg Pro Asn Asp Pro Asn
            340                 345                 350

Ala Glu Thr Leu Gln Glu Val Leu Asp Ser Gly Ala Tyr Tyr Gln Lys
        355                 360                 365

Ala Asn Ile Gly Leu Ala Ile Ala Thr Asp Ser Thr Leu Ser Lys Trp
    370                 375                 380
```

-continued

```
Lys Phe Leu Ser Pro Leu Ile Ser Ala Asn Cys Val Asn Asp Gln Thr
385                 390                 395                 400

Glu Arg Pro Gln Val Tyr Leu His Asn Gly Lys Tyr Tyr Ile Phe Thr
            405                 410                 415

Ile Ser His Arg Thr Thr Phe Ala Ala Gly Val Asp Gly Pro Asp Gly
        420                 425                 430

Val Tyr Gly Phe Val Gly Asp Gly Ile Arg Ser Asp Phe Gln Pro Met
        435                 440                 445

Asn Tyr Gly Ser Gly Leu Thr Met Gly Asn Pro Thr Asp Leu Asn Thr
    450                 455                 460

Ala Ala Gly Thr Asp Phe Asp Pro Ser Pro Asp Gln Asn Pro Arg Ala
465             470                 475                 480

Phe Gln Ser Tyr Ser His Tyr Val Met Pro Gly Gly Leu Val Glu Ser
            485                 490                 495

Phe Ile Asp Thr Val Glu Asn Arg Arg Gly Gly Thr Leu Ala Pro Thr
            500                 505                 510

Val Arg Val Arg Ile Ala Gln Asn Ala Ser Ala Val Asp Leu Arg Tyr
        515                 520                 525

Gly Asn Gly Gly Leu Gly Gly Tyr Gly Asp Ile Pro Ala Asn Arg Ala
    530                 535                 540

Asp Val Asn Ile Ala Gly Phe Ile Gln Asp Leu Phe Gly Gln Pro Thr
545                 550                 555                 560

Ser Gly Leu Ala Ala Gln Ala Ser Thr Asn Asn Ala Gln Val Leu Ala
            565                 570                 575

Gln Val Arg Gln Phe Leu Asn Gln
            580
```

COMPOSITIONS AND METHODS COMPRISING THE USE OF A *BACILLUS AGARADHAERENS* INULOSUCRASE (INUO)

CROSS REFERENCE TO RELATED APPLICATIONS

The present application is a continuation of U.S. patent Ser. No. 15/532,093 filed on 4 Dec. 2015, which is a 35 U.S.C. § 371 national phase filing of International Patent Application No. PCT/US2015/063841, filed 4 Dec. 2015, which claims the benefit of priority from US provisional application U.S. Ser. No. 62/088,320, filed 5 Dec. 2014, which is herein incorporated by reference in its entirety.

TECHNICAL FIELD

An isolated and/or purified inulosucrase from *Bacillus agaradhaerens*, recombinantly engineered variants thereof, active fragments thereof, synthetic nucleic acids encoding the inulosucrase and variants thereof, host cells comprising the synthetic nucleic acids, and compositions comprising the inulosucrase are provided. Methods of using the compositions include the manufacture of inulooligosaccharides.

SEQUENCE LISTING

A Sequence Listing, comprising SEQ ID NOs: 1-19, is attached and incorporated herein by reference in its entirety.

BACKGROUND

Fructooligosaccharides (FOS) of the inulin type, inulooligosaccharides (IOS), are gaining increased attention due to their beneficial health effects. Short chain FOS of the inulin type and inulin-type fructans are of interest due to their demonstrated pronounced in vitro prebiotic effect. i.e., as food sources for beneficial bacteria. Inulin also is used in the food industry as fat replacer, and for providing texture and stability in several products, such as desserts, bakery, and fermented dairy products, as well as infant formula.

IOS comprises a sucrose molecule elongated by a chain of fructosyl units with β-(2→1) linkages between the fructose units. IOS polymers contain repeating units with the generic structure. GFn, where "G" refers to a glucose molecule and "Fn" to the number of fructose units. Examples include 1-kestose (GF2), 1-nystose (GF3), and 1$^F$-fructofuranosyl-nystose (GF4). IOS polymers from plants, for example, generally contain 30-50 fructosyl units.

Fructosyltransferases (FTases) produced by plants, fungi, and bacteria catalyze the synthesis of FOS. FTases belong to clan GH-J enzymes, which contains the glycoside hydrolase 32 (GH32) and glycoside hydrolase 68 (GH68) families. About ninety-one FTase protein amino acid sequences within the GH32 and GH68 families are currently known. The GH32 and GH68 families share a five bladed β-propeller fold, each consisting of four antiparallel β-strands, together forming a central negatively charged cavity. The sequences are grouped in five plant clades, one fungal clade, and one bacterial clade. See Alméciga-Diaz et al. (2011) "Computational analysis of the fructosyltransferase enzymes in plants, fungi and bacteria." Gene 484:26-34. FTases of the GH68 family polymerize the fructose moiety of their substrate sucrose into fructans. FTases include both inulosucrases and levansucrases. Generally, inulosucrases catalyze polymerization through β-(2→1) linkages, and levansucrases catalyze polymerization by β-(2→6) linkages.

Inulosucrases catalyze a chemical reaction that results both in further polymerization through β-(2→1) linkages and in the generation of glucose:

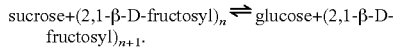

sucrose+(2,1-β-D-fructosyl)$_n$ ⇌ glucose+(2,1-β-D-fructosyl)$_{n+1}$.

A relatively low number of the known FTase enzymes have been identified as inulosucrases (EC 2.4.1.9). Inulosucrase enzymes and encoding genes identified so far are mainly present in lactic acid bacteria: *Lactobacillus gasseri* strains, *Streptococcus mutans*, *Leuconostoc citreum* CW28, *Lactobacillus johnsonii* NCC 533, *L. reuteri* 121, and *L. reuteri* TMW1.106. The characterized inulosucrase enzymes and genes from the GH68 family synthesize large inulin polymers. For example, the *L. reuteri* 121 INU inulosucrase synthesizes inulin polymers over 1×10$^7$ Da in size; the *L. jonsonii* INUJ inulosucrase synthesizes inulin polymers about 4×10$^7$ Da in size; and the *S. mutans* GS-5 inulosucrase synthesizes inulin polymers about 7×10$^7$ Da in size. While the inulin polymers synthesized by these enzymes are large, the inulin oligosaccharides have a relatively small GF range of GF2-GF6. A fructansucrase enzyme from *Bacillus* sp. 217C-11 has been biochemically characterized. The *Bacillus* enzyme synthesizes only IOS with a GF range of GF10-GF25 and a peak at GF16-GF17. See Wada et al. (2003) "A novel enzyme of *Bacillus* sp. 217C-11 that produces inulin from sucrose." Biosci. Biotechnol. Biochem. 67: 1327-1334.

SUMMARY

*Bacillus agaradhaerens* strain WDG185 expresses an inulosucrase that efficiently synthesizes a broad range of IOS with a GF range of GF3-GF30. The isolated and/or purified inulosucrase, recombinantly engineered variants thereof, active fragments thereof, synthetic nucleic acids encoding the inulosucrase, its variants, or its active fragments, host cells comprising the synthetic nucleic acids, and compositions comprising the inulosucrase are provided. Methods of using the compositions include the manufacture of inulooligosaccharides.

Accordingly, provided is an isolated, recombinantly expressed inulosucrase from *Bacillus agaradhaerens* (INUO) comprising a polypeptide consisting of amino acids 32-453 of SEQ ID NO: 4, a recombinantly engineered variant thereof, or an active fragment thereof, wherein the variant is able to catalyze polymerization of inulin oligosaccharides containing β-(2→1) linkages, and wherein the variant has at least 60% sequence identity with amino acids 32-453 of the amino acid sequence of SEQ ID NO: 4. The inulosucrase comprising the polypeptide consisting of amino acids 32-453 of SEQ ID NO: 4 may comprise at least one amino acid not normally associated with naturally occurring INUO from *Bacillus agaradhaerens* strain WDG185 (SEQ ID NO: 4). The recombinantly engineered variant may have at least 80%, at least 85%, at least 90%, at least 95%, or at least 98% sequence identity with amino acids 32-453 of the amino acid sequence of SEQ ID NO: 4. Alternatively, the recombinantly engineered variant may have at least 99% or at least 99.5% sequence identity with amino acids 32-453 of the amino acid sequence of SEQ ID NO: 4. The amino acid residues of the recombinantly engineered variant that are not identical to amino acids 32-453 of SEQ ID NO: 4 may be selected from conservative amino acid substitutions or deletions from either the C- or N-termini. The amino acid sequence of the recombinantly engineered variant may comprise a sequence identical to amino acids 79-393 of SEQ ID NO: 4.

A composition comprising the inulosucrase is also provided. The inulosucrase may be in a lyophilized powder form, an encapsulated form, a coated form, a granulated form, or a liquid formulation. The composition may further comprise a diluent.

Also provided are (1) a synthetic nucleic acid encoding the inulosucrase; (2) a vector comprising the synthetic nucleic acid; and (3) a host cell comprising the synthetic nucleic acid or the vector. The vector may be an expression vector. The vector may comprise a polynucleotide consisting of the nucleotide sequence of SEQ ID NO: 3. In one embodiment, the host cell may comprise the polynucleotide consisting of the nucleotide sequence of SEQ ID NO: 3. In another embodiment, a host cell that is not *Bacillus agaradhaerens* may comprise the nucleotide sequence of SEQ ID NO: 3. Further provided is a composition comprising the host cell and a food-grade, feed-grade, industrial-grade, or pharmacologically acceptable carrier, diluent, or excipient. A method of using the composition may comprise administering the composition to an individual, wherein the composition is capable of acting as a probiotic in the individual.

Also provided is a method of producing an inulosaccharide (IOS) product comprising contacting the inulosucrase with a fructose source, and reacting the inulosucrase with the fructose source at pH 5-10 and at 40° C.-60° C. to produce the IOS product. The fructose source may be sucrose, stachyose, raffinose, inulin, or a fructooligosaccharide (FOS). The IOS product may have a GF range of GF3-GF100, GF3-GF30, or GF10-GF25. The inulosucrase may be provided in a composition comprising a host cell comprising a nucleic acid encoding recombinant INUO. The method of producing an inulosaccharide (IOS) may further comprise chemical modification of the IOS product.

Also provided is a method of producing a tailored oligofructoside product comprising contacting the inulosucrase with a sucrose analogue having the glucose cap of sucrose substituted by another saccharide, and reacting the inulosucrase with the sucrose analogue at pH 5-10 and at 40° C.-60° C. to produce the tailored oligofructoside product. The sucrose analogue may have the glucose cap of sucrose substituted by a galactose, a mannose, a fucose, a xylose, or an allose. The inulosucrase is provided in a composition comprising a host cell comprising a nucleic acid encoding recombinant INUO.

Glossary

BLAST Basic Local Alignment Search Tool
CAZy carbohydrate active enzymes database
EDTA ethylenediaminetetraacetic acid
FOS fructooligosaccharide(s)
Ftase, FTF, or FS fructosyltransferase(s)
GFn a repeating structure in an IOS polymer, where G refers to a glucose molecule and Fn to the number of fructose units, e.g., GF4
GH32 family 32 of glycoside hydrolases
GH68 family 68 of glycoside hydrolases
GLC EI/MS gas-liquid chromatography (GLC) combined with electron-impact mass spectrometry (EI/MS)
GPC gel permeation chromatography
HOD signal an NMR signal from water in which one proton is exchanged for a deuterium
HPAEC high performance anion-exchange chromatography
HPLC high performance liquid chromatography
HPSEC high performance size exclusion chromatography
HSQC heteronuclear single quantum coherence
INUO inulosucrase from *Bacillus agaradhaerens*
IOS inulooligosaccharide(s)
MALLS multi angle laser light scattering
NMR nuclear magnetic resonance
RI refractive index
SEC size-exclusion chromatography
TLC thin layer chromatography
universal buffer a mixture of $Na_2HPO_4$ and citric acid designed to give a specific pH
PDI polydispersity index
Mw weight average molecular weight
Mn average molecular weight
Mp peak molecular weight

BRIEF DESCRIPTION OF THE DRAWINGS

FIG. 2 depicts the amino acid sequence of the INUO enzyme from *B. agaradhaerens* strain WDG185 (SEQ ID NO: 4). The regions corresponding to the conserved regions (I-XI) identified in the catalytic domains of other fructansucrase enzymes are bold and underlined. "∇" represents catalytic residues; and "↓" represents $Ca^{2+}$ binding residues. "~" indicates the deduced 31-aa signal peptide sequence.

FIG. 3 depicts IOS formation by recombinant INUO (amino acids 32-453 of the amino acid sequence of SEQ ID NO: 4). Reaction conditions were 800 mM sucrose, 200 mL (1.79 mg/mL) of INUO in 2 L of 800 mM sucrose, 75 mM universal buffer pH 7.0. At different time intervals (0-4 h) samples were withdrawn.

DETAILED DESCRIPTION

Figure 1:
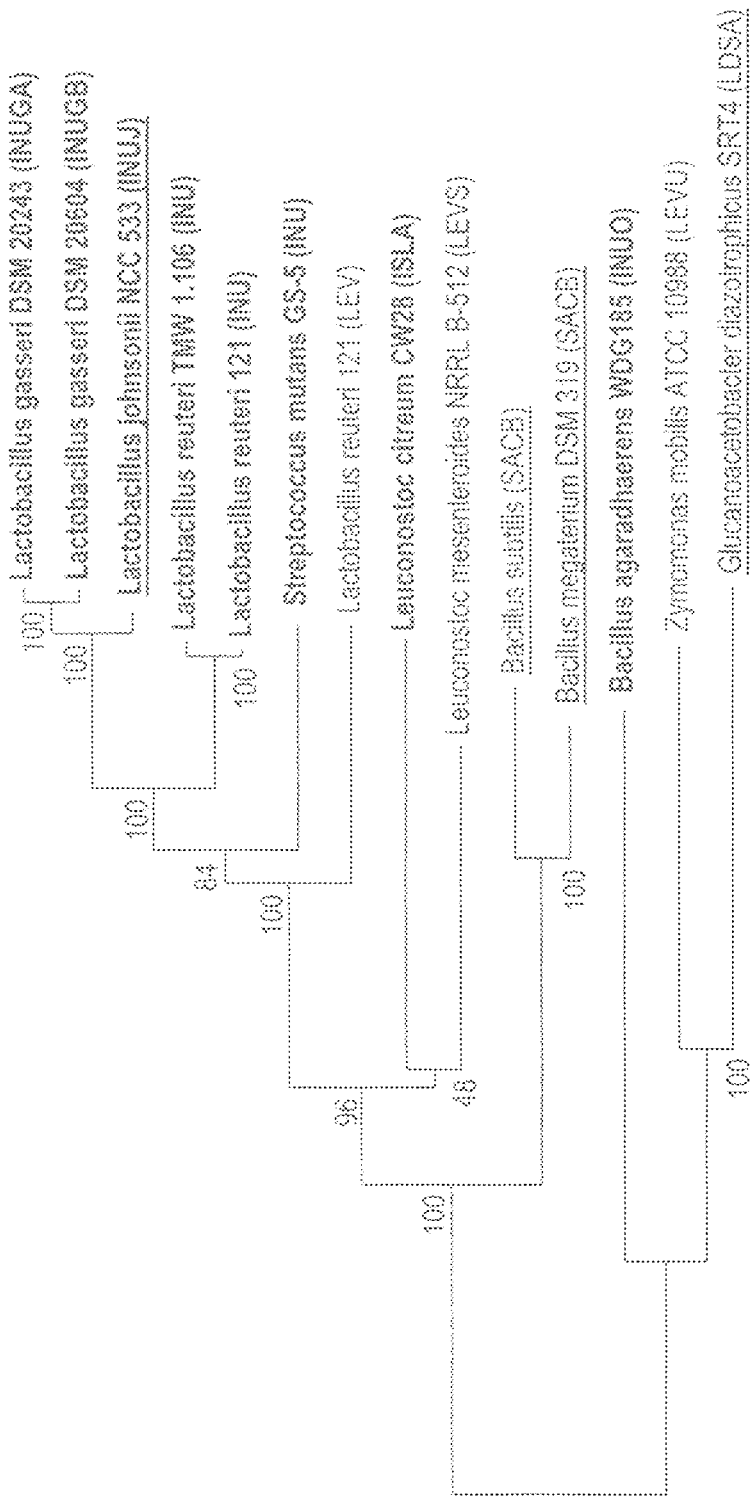
FIG. 1 depicts a phylogenetic tree of FTases (inulosucrases and levansucrases) from lactic acid bacteria. Bootstrap test of phylogeny was performed by the neighbour-joining method using 500 replicates. Bootstrap values in percentage are indicated at the branching points. The scale bar corresponds to a genetic distance of 0.1 substitution per position. FTases with available three-dimensional structural information are underlined. Inulosucrases are in grey font, and levansucrases are in black font; the presently disclosed INUO enzyme from *Bacillus agaradhaerens* strain WDG185 is bolded.
Figure 3A:
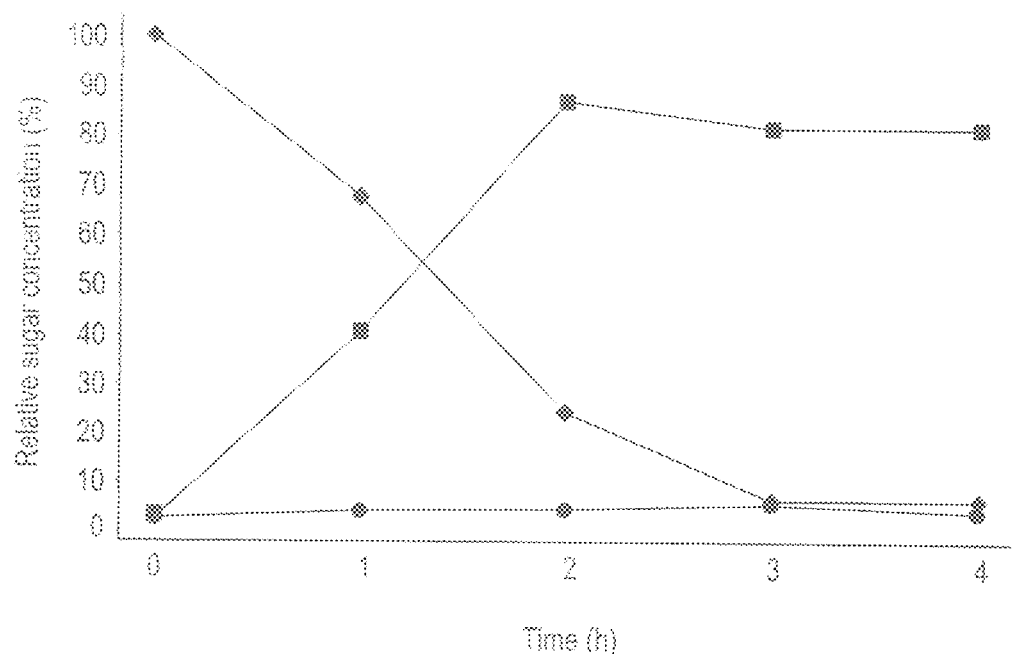
FIG. 3A depicts high performance liquid chromatography (HPLC) analysis showing the relative amounts of the levels of sucrose (♦), glucose (■) and fructose (●).
Figure 3B:
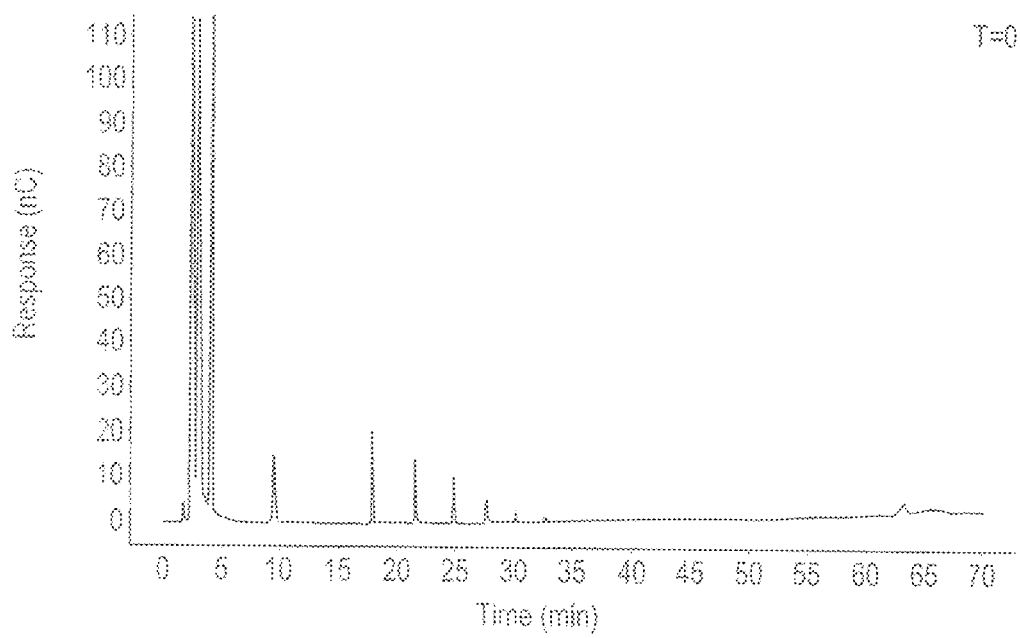
FIG. 3B depicts high performance anion-exchange chromatographic (HPAEC) analysis showing IOS formation over time, measured at T=0, 1, 2, 3, and 4 hours after the reaction is initiated.
Figure 3C:
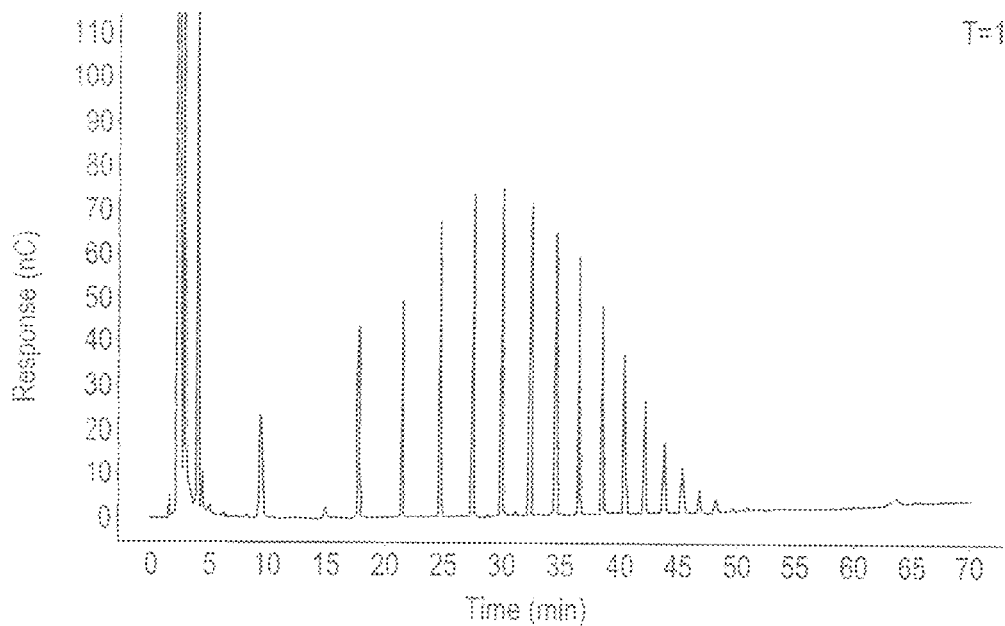
FIG. 3C depicts high performance anion-exchange chromatographic (HPAEC) analysis showing IOS formation over time, measured at T=0, 1, 2, 3, and 4 hours after the reaction is initiated.
Figure 3D:
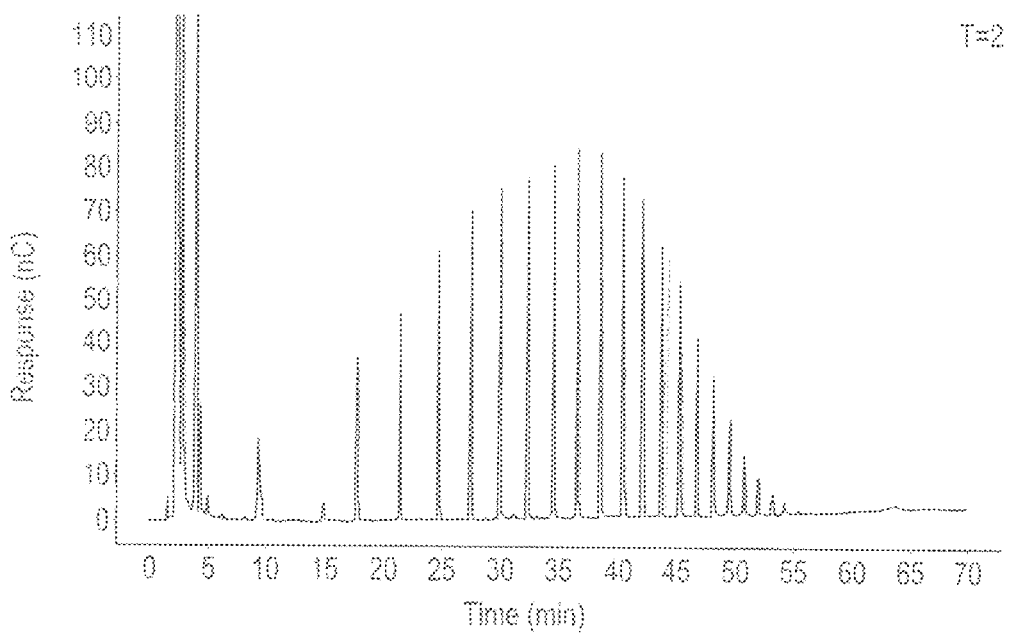
FIG. 3D depicts high performance anion-exchange chromatographic (HPAEC) analysis showing IOS formation over time, measured at T=0, 1, 2, 3, and 4 hours after the reaction is initiated.
Figure 3E:
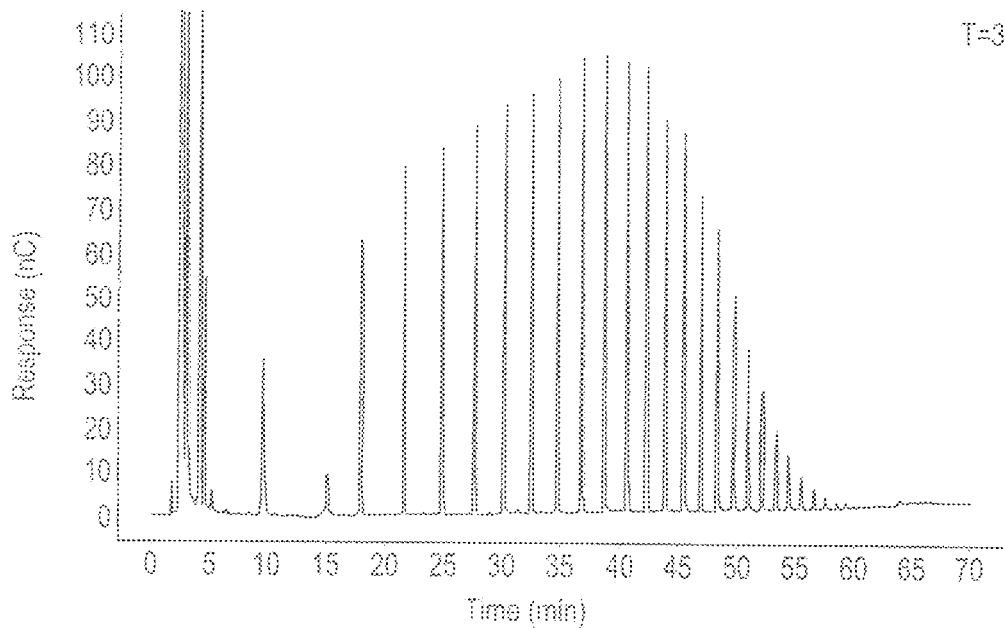
FIG. 3E depicts high performance anion-exchange chromatographic (HPAEC) analysis showing IOS formation over time, measured at T=0, 1, 2, 3, and 4 hours after the reaction is initiated.
Figure 3F:
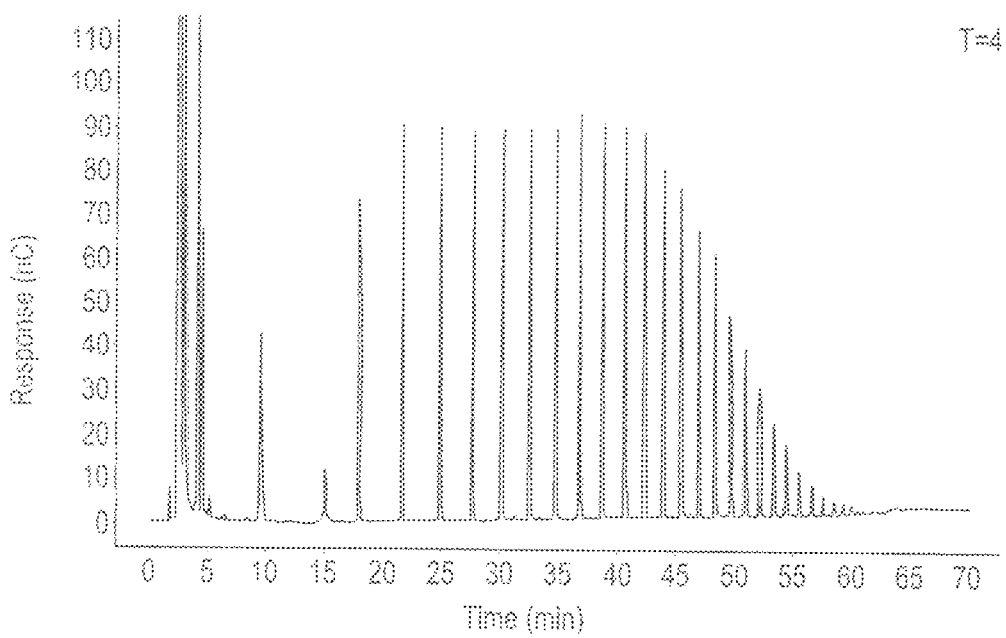
FIG. 3F depicts high performance anion-exchange chromatographic (HPAEC) analysis showing IOS formation over time, measured at T=0, 1, 2, 3, and 4 hours after the reaction is initiated.

An inulosucrase from *Bacillus agaradhaerens* (INUO), recombinantly engineered variants thereof, and active fragments thereof are disclosed. The full length sequence of the inulosucrase consists of the amino acid sequence set forth in SEQ ID NO: 4. The INUO may consist of amino acids 32-453 of the amino acid sequence of SEQ ID NO: 4, when expressed as a mature enzyme. The recombinant INUO enzyme possesses inulosucrase activity and is able to catalyze polymerization of inulin oligosaccharides containing β-(2→1) linkages. INUO may comprise a polypeptide consisting of amino acids 32-453 of SEQ ID NO: 4, where additional amino acid sequences may be fused to the N-terminus and/or C-terminus of the polypeptide consisting of amino acids 32-453 of SEQ ID NO: 4. The amino acid sequences fused at either termini may contain amino acid sequences not normally associated with naturally occurring INUO. For example, such amino acid sequences may be useful for labeling or purifying the protein. Such amino acid sequences also include polypeptides that confer a new function on the expressed INUO. For example, a heterologous carbohydrate binding domain may be fused to the carboxyl terminus of the recombinant INUO.

The INUO may be "isolated," meaning that it is separated from at least some of the biological material with which it is associated in nature, and then purified and concentrated into a form that is not found in nature, e.g., in a lyophilized powder form, an encapsulated form, a coated form, a granulated form, or a liquid formulation. The INUO may be "recombinantly expressed," meaning that it is expressed within a recombinant host cell from a DNA or a similar synthetic nucleic acid. A signal peptide may be operably linked to the N-terminus to facilitate secretion of the recombinantly expressed protein from an expression vector within a host cell. The signal peptide may have the sequence of amino acids 1-31 of SEQ ID NO: 4, for example. INUO alternatively may be linked to a different signal sequence, such as a signal sequence from another bacterial species, e.g., another *Bacillus* sp. signal sequence. The signal peptide may be proteolytically cleaved during recombinant expression to yield the mature form of the inulosucrase.

"Recombinant INUO" includes recombinantly expressed INUO consisting of amino acids 32-453 of SEQ ID NO: 4, as well as recombinantly engineered variants thereof or active fragments thereof. A "recombinantly engineered variant" contains at least one amino acid substitution or deletion from the N- or C-terminus, compared to amino acids 32-453 of SEQ ID NO: 4. The amino acid sequence of a recombinantly engineered variant varies from the amino acid sequence of the naturally occurring inulosucrase of SEQ ID NO: 4 by at least one amino acid. A recombinantly engineered variant may show at least 60%, at least 80%, at least 85%, at least 90%, at least 95%, at least 98%, at least 99% or at least 99.5% sequence identity with amino acids 32-453 of the amino acid sequence of SEQ ID NO: 4. Variants of INUO may consist of amino acids 32-453 of the amino acid sequence of SEQ ID NO: 4, wherein the non-identical amino acids may be amino acid substitutions or deletions from either the C- or N-termini. For example, a variant with a deletion of residues 449-453 of SEQ ID NO: 4 would have at least 98% sequence identity with amino acids 32-453 of the amino acid sequence of SEQ ID NO: 4. Recombinant INUO include, but are not limited to, polypeptides with 1, 2, 3, or 4 randomly selected amino acid modifications. The amino acid substitution also may be selected from the conservative amino acid substitutions shown in TABLE 1:

TABLE 1

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions, and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art and include site-directed mutagenesis, for example.

An active fragment of the recombinantly expressed INUO is also provided. An active fragment of INUO is a portion of INUO that retains a measureable inulosucrase activity, and is able to catalyze polymerization of inulin oligosaccharides containing β (2→1) linkages.

As used herein, "percent sequence identity" means that a variant has at least a certain percentage of amino acid residues identical to the wild-type enzyme, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either termini are included. For example, a variant with a deletion of residues 449-453 of SEQ ID NO: 4 would have at least 98% sequence identity, but not at least 99%, sequence identity (417/422 identical residues×100 gives 98.8% sequence identity), relative to the amino acids 32-453 of the amino acid sequence of SEQ ID NO: 4.

Amino acid modifications in the INUO variants may include residues in sequence motifs that are conserved compared to other GH68 enzymes. For example, motifs I-XI of INUO, which are depicted in FIG. 2, are sequence motifs conserved in other GH68 enzymes (TABLE 2). TABLE 2 depicts an amino acid sequence alignment of conserved regions (I-XI) in the catalytic domains of various fructan-sucrase enzymes (the beginning and ending positions of each motif for each enzyme are provided), wherein "INU" represents inulosucrases; "LEV" represents levansucrases; "∇" represents catalytic residues; "↓" represents $Ca^{2+}$ binding residues; "*" indicates identical residue; ":" indicates conserved substitutions; and "." indicates semi-conserved substitutions.

TABLE 2

| Strain | Enzyme | | SQN | I | II | III | IV |
|---|---|---|---|---|---|---|---|
| | | | | ↓∇ | | | |
| B. subtilis | SACB | LEV | 7 | $^{84}$VWDSW$^{88}$ | $^{162}$EWSGS$^{166}$ | $^{172}$DG$^{173}$ | $^{174}$KIRLFYTD$^{181}$ |
| B. megaterium DSM319 | SACB | LEV | 8 | $^{93}$VWDSW$^{97}$ | $^{171}$EWSGS$^{175}$ | $^{181}$DG$^{182}$ | $^{183}$KVRLFYTD$^{190}$ |
| Ln. mesenteroides NRRL B-512 | LEVS | LEV | 9 | $^{245}$VWDSW$^{249}$ | $^{315}$BQWSGS$^{319}$ | $^{325}$DD$^{326}$ | $^{327}$SIQLFYTK$^{334}$ |
| L. gasseri 20243 | INUGA | INU | 10 | $^{264}$IWDSW$^{268}$ | $^{332}$QWSGS$^{336}$ | $^{342}$DG$^{343}$ | $^{344}$SIQLYYTK$^{351}$ |
| L. gasseri 20604 | INUGB | INU | 11 | $^{264}$IWDSW$^{268}$ | $^{332}$QWSGS$^{336}$ | $^{342}$DG$^{343}$ | $^{344}$SIQLYYTK$^{351}$ |
| L. jonsonii NCC533 | INUJ | INU | 12 | $^{270}$IWDSW$^{274}$ | $^{338}$QWSGS$^{342}$ | $^{348}$DG$^{349}$ | $^{350}$SIQLYYTK$^{357}$ |
| L. reuter TMW1.106 | INU | INU | 13 | $^{270}$VWDSW$^{274}$ | $^{339}$EWSGS$^{343}$ | $^{349}$DN$^{350}$ | $^{351}$SIQLFYTR$^{358}$ |
| L. reuter 121 | INU | INU | 14 | $^{270}$VWDSW$^{274}$ | $^{339}$EWSGS$^{343}$ | $^{349}$DN$^{350}$ | $^{351}$SIQLFYTR$^{358}$ |
| L. reuter 121 | LEV | LEV | 15 | $^{247}$VWDSW$^{251}$ | $^{318}$EWSGS$^{322}$ | $^{328}$DG$^{329}$ | $^{330}$TIQLFFTS$^{337}$ |
| S. mutans GS-5 | INU | INU | 16 | $^{246}$VWDSW$^{250}$ | $^{315}$EWSGS$^{319}$ | $^{325}$DG$^{326}$ | $^{327}$SLQLFYTK$^{334}$ |
| Ln. mesenteroides CW28 | ISLA | INU | 17 | $^{353}$VWDSW$^{357}$ | $^{423}$EWSGS$^{427}$ | $^{433}$DD$^{434}$ | $^{435}$SIQLFYTR$^{442}$ |
| Z. mobilis ATCC 10988 | LEVU | LEV | 18 | $^{46}$VWDTW$^{50}$ | $^{117}$EWSGC$^{121}$ | $^{129}$AN$^{130}$ | $^{131}$SVEVFFTS$^{138}$ |
| G. diazotrophicus SRT4 | LDSA | LEV | 19 | $^{133}$VWDTW$^{137}$ | $^{223}$EWSGS$^{227}$ | $^{235}$GN$^{236}$ | $^{237}$TVSVFYTD$^{244}$ |
| B. agradhaerans WDG185 | INUO | INU | 4 | $^{79}$VWDTW$^{83}$ | $^{149}$QWAGS$^{153}$ | $^{159}$DG$^{160}$ | $^{161}$KVHFFYTA$^{168}$ |
| | | | | :**:* | :*:*. | . | .: .::* |

| Enzyme | | SQN | V | VI | VII | VIII | IX | X | XI |
|---|---|---|---|---|---|---|---|---|---|
| | | | ↓   ∇ | | | ↓ ∇ | | | |
| SACB | LEV | 7 | $^{241}$DNHTLRDP$^{248}$ | $^{258}$YLVFE$^{262}$ | $^{330}$PLI$^{332}$ | $^{339}$DEIER$^{343}$ | $^{354}$YLFTD$^{358}$ | $^{388}$YKPLN$^{392}$ | $^{410}$TYS$^{412}$ |
| SACB | LEV | 8 | $^{251}$DNHTLRDP$^{258}$ | $^{268}$YLVFE$^{272}$ | $^{340}$PLI$^{342}$ | $^{349}$DEIER$^{353}$ | $^{364}$YLFTD$^{368}$ | $^{398}$YKPLN$^{402}$ | $^{420}$TYS$^{422}$ |
| LEVS | LEV | 9 | $^{393}$DNFTMRDP$^{400}$ | $^{410}$YLAFE$^{414}$ | $^{485}$PLL$^{487}$ | $^{494}$DEIER$^{498}$ | $^{509}$YLFTD$^{513}$ | $^{544}$YTPLN$^{548}$ | $^{566}$TYS$^{568}$ |
| INUGA | INU | 10 | $^{413}$DNIAMRDA$^{420}$ | $^{431}$YLVFE$^{435}$ | $^{506}$PFI$^{508}$ | $^{515}$DEIER$^{519}$ | $^{530}$YLFAA$^{534}$ | $^{571}$YVPLN$^{575}$ | $^{593}$TYS$^{595}$ |
| INUGB | INU | 11 | $^{413}$DNIAMRDA$^{420}$ | $^{431}$YLVFE$^{435}$ | $^{506}$PLI$^{508}$ | $^{515}$DEIER$^{519}$ | $^{530}$YLFAA$^{534}$ | $^{571}$YVPLN$^{575}$ | $^{593}$TYS$^{595}$ |
| INUJ | INU | 12 | $^{419}$DNIAMRDA$^{426}$ | $^{437}$YLVFE$^{441}$ | $^{512}$PLI$^{514}$ | $^{521}$DEIER$^{525}$ | $^{536}$YLFAA$^{540}$ | $^{577}$YVPLN$^{581}$ | $^{594}$TYS$^{596}$ |
| INU | INU | 13 | $^{418}$DNIAMRDA$^{125}$ | $^{436}$YLVFE$^{440}$ | $^{511}$PLI$^{513}$ | $^{520}$DEIER$^{524}$ | $^{535}$YLFAA$^{539}$ | $^{576}$YKPLN$^{580}$ | $^{598}$TYS$^{600}$ |
| INU | INU | 14 | $^{418}$DNIAMRDA$^{425}$ | $^{436}$YLVFE$^{440}$ | $^{511}$PLI$^{513}$ | $^{520}$DEIER$^{524}$ | $^{535}$YLFAA$^{539}$ | $^{576}$YKPLN$^{580}$ | $^{598}$TYS$^{600}$ |
| LEV | LEV | 15 | $^{398}$DDYCLRDP$^{405}$ | $^{416}$YLVFE$^{420}$ | $^{491}$PLV$^{493}$ | $^{500}$DEVER$^{504}$ | $^{515}$YLFSV$^{519}$ | $^{556}$YKPLN$^{560}$ | $^{578}$TYS$^{580}$ |
| INU | INU | 16 | $^{396}$DNIAMRDP$^{403}$ | $^{414}$YLVFE$^{418}$ | $^{489}$PLL$^{491}$ | $^{498}$DELER$^{502}$ | $^{513}$YLFTA$^{517}$ | $^{554}$YKPLN$^{558}$ | $^{576}$TYS$^{578}$ |
| ISLA | INU | 17 | $^{495}$DMFTLRDP$^{502}$ | $^{513}$YLTFE$^{517}$ | $^{588}$PLI$^{590}$ | $^{597}$DEIER$^{601}$ | $^{612}$YLFTD$^{616}$ | $^{650}$YKPLN$^{654}$ | $^{672}$TYS$^{674}$ |
| LEVU | LEV | 18 | $^{188}$NFWDFRDP$^{195}$ | $^{207}$YALFE$^{211}$ | $^{266}$PLV$^{268}$ | $^{275}$DQTER$^{279}$ | $^{290}$YLFTI$^{294}$ | $^{323}$YEPLN$^{327}$ | $^{343}$AYS$^{345}$ |
| LDSA | LEV | 19 | $^{303}$EFFNFRDP$^{310}$ | $^{323}$YMVFE$^{327}$ | $^{389}$PLI$^{391}$ | $^{398}$DQTER$^{402}$ | $^{413}$YIFTI$^{417}$ | $^{445}$FQPMN$^{449}$ | $^{483}$SYS$^{485}$ |
| INUO | INU | 4 | $^{236}$IISAFRDP$^{243}$ | $^{255}$YIIWE$^{259}$ | $^{314}$PLL$^{316}$ | $^{325}$HQLER$^{329}$ | $^{338}$YLLTI$^{342}$ | $^{371}$YEPLN$^{375}$ | $^{391}$AYS$^{393}$ |
| | | | **. | * :* | *:: | .: ** | *::: | : *:* | :** |

Motifs I, V, and VIII have been identified as regions containing the three catalytic amino acid residues in FTases. Variants of INUO may consist of amino acids 32-453 of the amino acid sequence of SEQ ID NO: 4. Alternatively, variants of INUO may comprise motifs I-IV (residues 79-168 of SEQ ID NO: 4) or motifs I-XI (residues 79-393 of SEQ ID NO: 4) that are identical to the amino acid sequence of SEQ ID NO: 4.

INUO may be a component of a composition. The composition may comprise purified INUO obtained from a culture of B. agaradhaerens or may comprise purified recombinant INUO, which may be expressed in a recombinantly modified host cell comprising nucleic acids encoding recombinant INUO. For example, the composition may comprise a host cell that expresses nucleic acids encoding the recombinant INUO. INUO may have at least 50%, at least 80%, at least 90%, at least 95%, or at least 98% purity in the composition. For example, INUO may be purified to homogeneity. The composition may include other components. For example, an INUO composition may comprise INUO as a lyophilized power and optionally one or more carriers, such as another protein without inulosucrase activity. The composition also may comprise INUO in a diluent, such as distilled water, distilled/deionized water, or a buffered saline solution.

Synthetic nucleic acids encoding recombinant INUO, e.g., DNA, vectors comprising the nucleic acids, and host cells comprising the vector or nucleic acids are provided. A "synthetic" nucleic acid contains at least one nucleotide residue that is not found in the naturally occurring sequence depicted in SEQ ID NO: 3. The nucleic acid sequences encoding recombinant INUO may comprise expression-regulating regions (e.g., promoters, enhancers, and terminators) that can be used for homologous or heterologous expression. Such expression-regulating sequences are operationally linked to a polypeptide-encoding nucleic acid sequence. As is well understood by one skilled in the art, the genetic code is degenerate, meaning that multiple codons in some cases may encode the same amino acid. Synthetic nucleic acids encoding recombinant INUO include all possible codon degeneracies. Nucleic acids encoding recombinant INUO may include the polynucleotide of SEQ ID NO: 3, which is the ftf gene of B. agaradhaerens.

A vector may comprise the synthetic nucleic acid encoding recombinant INUO. The vector may be an expression vector capable of expressing recombinant INUO, for example. The vector may comprise one or more selectable markers, e.g., an antibiotic resistance gene. Vectors comprising INUO-encoding nucleic acids may include those vectors that comprise the ftf polynucleotide of SEQ ID NO: 3. Other vectors may comprise a polynucleotide consisting of the nucleotide sequence of SEQ ID NO: 3. A recombinant host cell, such as a plant, animal, fungal, or bacterial cell, containing one or more copies of the nucleic acid construct are provided. The host cell may be a bacterial cell, e.g., Bacillus sp., which is capable of expressing and secreting the recombinant INUO. Other host bacterial cells may not be Bacillus agaradhaerens. A host cell may comprise the vector comprising a polynucleotide consisting of the nucleotide sequence of SEQ ID NO: 3. Suitable techniques for making and using nucleic acids encoding recombinant INUO, vectors, expression constructs comprising the nucleic acids, and host cells are well known in the art.

A method of using an INUO, e.g., a recombinant INUO, to produce an IOS product is also provided. The method may comprise contacting an INUO with a suitable fructose source, such as sucrose, stachyose, raffinose, or a FOS. Suitable sucrose sources include, but are not limited to, raw substrates, like sugar cane, beet juice, and molasses. When producing inulin from sucrose, the final average polymerization degree of inulin (i.e., GFn) can be affected by controlling the sucrose concentration of the culture media, the temperature when inulin synthase is brought into contact with sucrose, and/or the timing of sucrose substrate addition during the reaction. See U.S. Pat. No. 7,507,558. The final average polymerization degree of inulin (i.e., GFn) may be in the range of GF3-GF100, or typically GF3-GF30 or GF10-GF25. Sucrose, for example, may be added at a concentration of level of 20-1000 mM. When 800 mM sucrose is added once to initiate the reaction, for example, the IOS product has a GF range of GF10-GF25, with a peak at GF16-GF17. The method can be performed over a broad pH range, e.g., about pH 5-10, about pH 5.5-9.5, about pH 6-8, or about pH 7. The temperature can be held over about 40° C.-60° C., e.g., about 45° C.-55° C., or about 50° C.

As noted above, the production of IOS by an INUO simultaneously generates glucose from the sucrose substrate. The glucose produced during the INUO-catalyzed reaction can be further utilized simultaneously with, or subsequently to, contacting an INUO with the suitable fructose source. For example, the method of using an INUO may further comprise isomerizing the liberated glucose to produce fructose. This isomerizing may be a step in the production of high fructose syrup, for example. Alternatively, the glucose may be utilized as a substrate for microorganisms, e.g., yeast, in a process of co-fermentation. For example, a microorganism that expresses an INUO may be co-cultured with the fermenting microorganism. In this case, the pH and temperature regime used for the INUO-catalyzed reaction may be optimized for co-culturing the fermenting microorganism and the microorganism that expresses an INUO.

The suitable fructose source that is contacted with the INUO may be a food that contains sucrose, for example. Contacting the food with an INUO lowers the sucrose content of the food, while increasing the amount of FOS in the food. The FOS advantageously serves as a dietary fiber with low caloric value. Suitable fructose sources in this context include, but are not limited to, juices and yogurt.

The INUO may be provided in a composition comprising a purified INUO or recombinant INUO. The INUO may be provided in the form of a composition comprising a cell that expresses INUO, e.g., a host cell comprising a nucleic acid encoding recombinant INUO. In this case, the cell may be in a non-growth state. This allows the production of the fructans to proceed without the necessity of supplying nutrients and other materials for supporting growth of the cells. Production can be performed by contacting the sucrose or other fructose source, such as raffinose, with the cells and withdrawing polysaccharides from the medium. The cells expressing INUO may be immobilized on a carrier, such as solid particles, filters, and reactor walls. The cells may be capable of co-expressing at least one enzyme in addition to INUO, such as a glucansucrase enzyme. For example, enzymes that may be co-expressed with INUO, e.g., an isomerase, could utilize the glucose produced during the INUO-catalyzed reaction as a substrate.

The IOS product may be chemically modified after the production process, depending on the desired application of the IOS product. Some chemical modifications of inulin and various industrial applications of the modified oligosaccharides are summarized in Stevens, et al. (2001) "Chemical modification of inulin, a valuable renewable resource, and its industrial applications." BioMacromolecules 2: 1-16. For example, carbamoylated inulin can serve as a biodegradable surface-active agent given its capability of reducing interfacial tension. Additionally, the introduction of carboxylic acid/carboxylate functions into carbohydrates leads to compounds and materials which may be used as detergent components or food ingredients. Inulin can be carboxymethylated according to procedures known in the art, e.g., Verraest et al. (1995) *Carbohydrate Res.* 271: 101-112 and WO 95/15984. Carboxymethylated inulin can be used as an antiscalant, for example. Alternatively, oxidation of IOS can be performed by means well known in the art, including those disclosed in EP 427349, WO 95/12619, and WO 95/07303, for example. Esterification of inulin can produce surface active molecules that can be used as food-grade nonionic surfactants. Alkoxylation of inulin has been shown to be useful in preparing water-blown polyurethane forms. See e.g., Rogge et al. (2005) "Applicant of ethoxylated inulin in water-blown polyurethane foams." *BioMacromolecules* 6: 1992-1997. Oxidized fructans have improved water-solubility, altered viscosity, and a retarded fermentability, facilitating their use as metal-complexing agents, detergent additives, strengthening additives, bioactive carbohydrates, emulsifiers, and water binding agents. Oxidized fructans coupled to compounds such as proteins or fatty acids can be used as emulsifiers and stabilizers.

FOS produced by the breakdown of the IOS product may be used in a prebiotic composition, which can be administered to an individual. Prebiotic compositions comprising the FOS product may be administered to individuals with constipation, diarrhea, and/or high cholesterol levels, for example. The FOS can serve as a substrate for microflora in the large intestine, increasing the overall gastrointestinal tract health. FOS and IOS also may promote calcium absorption in both the animal and the human gut. The FOS also may be useful as a dietary fiber with low caloric value. Twenty (20) grams of the prebiotic composition may be administered to a human per day, for example.

A recombinant host cell capable of expressing recombinant INUO may be used in a composition capable of acting as a probiotic. The recombinant host cell can produce IOS in the gut following ingestion, thereby promoting the growth of strains like *Bifidobacterium* that can metabolize inulin. The composition may further comprise a food-grade, feed-grade, industrial-grade, or pharmacologically acceptable carrier, diluent, or excipient. In this context, "pharmaceutically acceptable" means that the component is safe for ingestion by animals and/or humans. The composition may be administered to an animal or human. The probiotic composition may be directly ingested in conjunction with food.

Further provided is a method of using an INUO, e.g., a recombinant INUO, to produce a tailored oligofructoside product (other than IOS), wherein the glucose cap of IOS is substituted, e.g., by another saccharide such as a galactose, manose, a fucose, or a xylose. See, e.g., Homann et al. (2012) "Chemo-enzymatic systhesis and in vitro cytokine profiling of tailor-made oligofructosides." *BMC Biotechnol.* 12: 90; Kralj et al. (2008) "Fructansucrase enzymes and sucrose analogues: A new approach for the synthesis of unique fructo-oligosaccharides." *Biocat. Biotransf* 26: 32-41. The method may comprise contacting an INUO with a suitable sucrose analogue wherein the glucose cap of sucrose is substituted by another saccharide, such as a galactose, a mannose, a fucose, a xylose, or an allose. Similar to producing IOS from sucrose, the final average polymerization degree of the tailored oligofructoside can be affected by controlling the sucrose analogue concentration of the culture media, the temperature when inulin synthase is brought into contact with the sucrose analogue, and/or the timing of sucrose analogue addition during the reaction. The method can be performed over a broad pH range, e.g., about pH 5-10, about pH 5.5-9.5, about pH 6-8, or about pH 7. The temperature can be held over about 40° C.-60° C., e.g., about 45° C.-55° C., or about 50° C.

The term "about" generally refers to ±15% of the referenced value. When defining a temperature, "about" refers to an average temperature during a process. The skilled artisan would expect the temperature of a process to vary somewhat about a set temperature, e.g., by ±1° C. from the set value. A temperature of "about 40° C." thus would encompass temperatures of 40±1° C. and also includes transient spikes in temperature that can occur during the process. For example, the temperature of a process may exceed 40° C. by several degrees over several minutes. These transient spikes are encompassed by "about 40° C."

Examples

Bacterial Strains, Plasmids, and Culturing Conditions

The entire genome (3.7 MB) of the *Bacillus agaradhaerens* strain WDG185 (Dupont Culture collection) was sequenced, using Ilumina Next Generation Sequencing (NGS) (San Diego, CA), and assembled (BaseClear, Leiden, The Netherlands). Its taxonomic position was identified by 16sRNA analysis (identity: 1436/1438=99% with *Bacillus agaradhaerens* strain DSM 8721) Contiguous sequence runs were annotated using BioXpr (Namur, Belgium). Using a Basic Local Alignment Search Tool (BLAST) search, two putative fructansucrase genes were identified in the *Bacillus agaradhaerens* WDG185 genome by their sequence homology with genes encoding SACB of *B. subtilis* (SEQ ID NO: 7) and INUJ of *L. johnsonii* NCC 533 (SEQ ID NO: 12).

*B. subtilis* SC6.1 (also called BG3594comK; ΔaprE, ΔnprE, degU$^{hy}$32, oppA, ΔspoIIE3501, amyE::xylRPxylAcomK-phleo) was used as a cell host for cloning. Its competency gene (comK) was placed under a xylose inducible promoter, which was used to induce competency for DNA binding and uptake. See Hahn et al. (1996) "Regulatory inputs for the synthesis of ComK, the competence transcription factor of *Bacillus subtilis*." *Mol. Microbiol.* 21: 763-775. The plasmid, pHPLT, was used for expression of the inuO gene in a *B. subtilis* SC6.1 host cell. See Van Solingen et al. (2001) *Extremophiles* 5: 333-341. Host cells containing recombinant plasmids were cultivated in Tryptone Soya Broth (Oxoid Ltd., UK) and Grant's II medium. See U.S. Pat. No. 8,507,244 B2. Heart Infusion agar plates (Difco Laboratories, MI) were used to select transformants. Plasmid integrity was maintained by the addition of 10 μg/mL neomycin.

Amino Acid Sequence Alignment of Inulosucrase from INUO and Phylogenetic Tree Construction The amino acid sequence of INUO and of previously characterized FTases, including both inulo- and levansucrases, were aligned with the ClustalW interface in MEGA version 4 (on the Internet at megasoftware.net) with gap-opening and extension penalties of 10 and 0.2, respectively. Amino acid sequences were acquired from the CAZy (carbohydrate active enzymes) database (on the Internet at cazy.org). The phylogenetic tree also was made using the MEGA program. A bootstrap test of phylogeny was performed by the neighbor-joining method using 500 replicates.

Molecular Techniques

General procedures for gene cloning, *E. coli* DNA transformations, DNA manipulations, and agarose gel electrophoresis were as described. See Green et al. (2013) MOLECU- LAR CLONING: A LABORATORY MANUAL, 4$^{th}$ ed., Cold Spring Harbor Laboratory Press, New York. Restriction endonuclease digestions and ligations with T4 DNA ligase were performed as recommended by the enzyme suppliers (New England BioLabs Inc., Ipswich, MA). Primers were obtained from Life Technologies, Frederick, MD Sequencing was performed using BaseClear (Leiden, NL). Plasmid DNA of *B. subtilis* was isolated using the NucleoSpin® Plasmid kit (Machery-Nagel GmbH & Co. KG, Dren, FRG).

Cloning of the inuO Gene

Total genomic DNA from *Bacillus agaradhaerens* was obtained by first growing the strain on Heart Infusion agar plates (Difco Laboratories, MI) at 37° C. for 24 h. Cell material was scraped from the plates and used to prepare genomic DNA with the ZF Fungal/Bacterial DNA miniprep kit from Zymo Research Corp. (Irvine, CA) (Cat No. D6005). DNA was amplified on a DNA thermal cycler Eppendorf Mastercycler® ep gradient S using Platinum Taq DNA Polymerase High Fidelity (Invitrogen™). The *B. agaradhaerens* inuO gene was amplified by polymerase chain reaction from the genomic DNA of *B. agaradhaerens* using primers:

```
BspK02313-FW
                                (SEQ ID NO: 1)
5'-CTCATTCTGCAGCTAGCGCAACCTC

AGACTGGGATGCTGAAGATGAT-3',
containing a PstI site (bold)
and a NdeI site (italics)
and BspK02313-RV
                                (SEQ ID NO: 2)
5'-CGCAGATATCGTTAACTCAACGATA

GGCACCGAATGGTCTGAT-3'
``` containing a HpaI site (bold). Using the PstI and HpaI restriction sites, the inuO amplicon was cloned into the expression vector pHPLT. The resulting vector (pHPLT-InuO) was transformed into *B. subtilis* SC6.1 for expression studies. Correct construction of the plasmid was confirmed by nucleotide sequence analysis (BaseClear, The Netherlands).

Deduced Amino Acid Sequence Analysis and Dendrogram of INUO

The ftf gene of *B. agaradhaerens* WDG185 was identified by the cloning and expression methods disclosed above. The nucleotide sequence of the ftf gene is disclosed in SEQ ID NO: 3. The ftf gene encodes a 453 amino acid protein with a putative signal sequence of 31 amino acids. The full length amino acid sequence of the encoded protein is shown in SEQ ID NO: 4. The putative cleavage site for the signal peptidase was determined using software provided on the Internet at cbs.dtu.dk/services/SignalP. The deduced molecular weight of the mature protein encoded by the ftf gene is 47.3 kDa. A core region of 416 amino acids (residues 32 to 447 of SEQ ID NO: 4) was identified by sequence homology (software on the Internet at pfam.janelia.org) as a member of glycoside hydrolase family 68 (GH68).

BLAST searches of INUO revealed highest similarity with a putative FTase from *Paenibacillus elgi*. The two proteins share 67% sequence identity over the entire protein sequence and 81% sequence identity within 443 amino acids. Residues 35-64 of the INUO of SEQ ID NO: 4 shared 50% sequence identity with a 30 amino acid N-terminal sequence from the partially characterized inulosucrase of *Bacillus* sp. 217C-11. See Wada et al. (2003).

INUO clustered most closely with levansucrases in the phylogenetic tree (FIG. 1) and not with the other known inulosucrase enzymes. The conserved motifs and amino acids reported to be involved in catalysis in GH68 enzymes were all present in the INUO sequence, as depicted in TABLE 2. See Van Hijum et al. (2006) *Microbiol. Mol. Biol. Rev.* 70: 157-176; Velázquez-Hernández et al. (2009) *J. Appl. Microbiol.* 106: 1763-1778.

Three amino acid residues important for catalytic activity of GH68 enzymes are also present in INUO. For example, the catalytic nuclepohile $D^{81}$ is present within a conserved (V/L)WD(T/S)(W/M) motif (SEQ ID NO: 5) located at residues 79-83 of INUO (SEQ ID NO: 4). Second, the transition state stabilizer residue $D^{242}$ is present in a conserved $RD^{242}P$ motif located at residues 241-243 of INUO. Third, the acid/base catalyst residue $E^{326}$ is present in a conserved D(E/Q)(I/T)ER motif (SEQ ID NO: 6) at residues 323-327 of INUO. See Velázquez-Hemández et al. (2009); Meng et al. (2003) *Nat. Struct. Biol.* 10: 935-941; Ozimek et al. (2004) *FEBS Lett.* 560: 131-133.

Amino acid residues surrounding the conserved motifs and catalytic amino acids showed differences with other GH68 enzymes, as shown in the sequence alignments depicted in TABLE 2. For example, the conserved sequence motif RDP, harboring the transition state stabilizer, is preceded by the sequence motif IAM in most inulosucrase enzymes, while in INUO the sequence motif SAF is present. Further differences are seen in the conserved D(E/Q)(I/T)ER motif (SEQ ID NO: 6). While the acid/base catalyst residue $E^{32}$ is present in INUO, the conserved aspartate (D) from the motif is instead a histidine (H) in INUO. The aspartate residue in the D(E/Q)(I/T)ER motif (SEQ ID NO: 6) coordinates with $Ca^{2+}$ in the calcium binding site of the *B. subtilis* SACB and *L. jonsonii* NCC533 INUJ enzymes. See Meng et al. (2003); Pijning et al. (2011) *J. Mol. Biol.* 412: 80-93. $D^{241}$, another residue constituting the calcium binding site in SACB, is instead an isoleucine ($I^{236}$) in INUO (see Table 2). This suggests that INUO does not bind $Ca^{2+}$, which would be consistent with the absence of an EDTA effect on INUO activity noted above. Further, the amino acid preceding the catalytic acid base catalyst residue $E^{32}$ is leucine (L), but is usually a conserved isoleucine or threonine in other GH68 enzymes. (See Table 2.)

The 31 amino acid signal sequence, and the various motifs and amino acid residues of INUO discussed above are bolded and highlighted in FIG. 2. The forward slash demarcates motifs III and IV.

InuO Gene Expression and Purification of INUO

Expression was initiated from a single colony of *B. subtilis* SC6.1 harboring pHPLT-InuO grown aerobically (250 rpm) at 37° C. for 6 h in TSB. The pre-culture (1 mL) was used to inoculate 200 mL Grant's II medium in a 2 L Bellco baffled shake flask, containing 3 drops of antifoam (Mazu DF 6000K, Mazer Chemicals, Gurnee, IL). After incubation for 66 h (at 220 rpm) at 37° C., the supernatant was collected by centrifugation (17000×g) and filtered through a 0.22 µm Durapore® PVDF membrane (EMD Millipore).

High expression levels of InuO were achieved using the *B. subtilis* SC6.1 above as host, yielding about 100 mg of highly purified protein from a 1 L culture. The predicted Mr of INUO was in agreement with the results obtained by SDS-PAGE analysis.

INUO enzyme present in the supernatant was purified to homogeneity by anion exchange chromatography using an AKTA Explorer System (GE Healthcare) equipped with a 1 mL ResourceQ column (GE Healthcare) and a linear gradient of 30 mL with 1 M NaCl in 20 mM Tris buffer, pH 7.5, at a flow rate of 1 mlUmin. Proteins present in the elution peak, as judged by SDS-PAGE, were desalted (Slide-A-Lyzer Dialysis Cassette 10 kDa MWCO, Pierce, Rockford, IL) using universal buffer, pH 7 (i.e., a mixture of $Na_2HPO_4$ and citric acid having a pH of 7). Protein concentrations were determined by the Bradford method using the Bio-Rad reagent and bovine serum albumin as a standard (Bio-Rad Laboratories, Hercules, CA).

pH and Temperature Optima

The pH optimum (25 mM universal buffer, pH 2-12) and temperature optimum (40-88° C.) were determined by measuring the amount of saccharides synthesized by 0.53 mg/mL purified INUO from 800 mM sucrose after 15 min (HPLC) or 24 h incubation (TLC) (data not shown). The amount of saccharides were determined qualitatively by thin layer chromatography (TLC) and/or quantitatively by high performance liquid chromatography (HPLC).

INUO showed a broad pH and temperature optimum from pH 5.5 to 9.5 (>60% activity) and 45° C. to 55° C. (>60% activity), respectively. Assays with various combinations of temperatures and buffers showed optimal activity for purified INUO at 50° C. and pH 7.0. INUO was not inhibited by addition of the $Ca^{2+}$ chelator, ethylenediaminetetraacetic acid (EDTA). The temperature and pH profiles/optima of INUO, as well as the effect of EDTA on enzyme activity, were most similar to those reported for the inulosucrase of *Bacillus* sp. 217C-11.

HPLC Assay for Sugar Concentration Determination

Sucrose, glucose, and fructose concentrations from enzymatic reactions of INUO with sucrose, were monitored using an Agilent 1200 (Agilent Technologies, Columbia, MD) HPLC equipped with 50 mm and 100 mm in-line connected RNM $Ca^{2+}$ carbohydrate columns (Phenomenex). The columns were operated at a temperature of 80° C. and a flow rate of 0.8 mL/min in an eluent of 10 mM sodium acetate, pH 5.5. Detection was done with a refractive index (RI) detector operating at a temperature of 35° C. The injection volume was 5 μL and appropriate calibration sets were used to determine exact sugar concentrations.

FOS Production and Characterization (i) FOS Production:

Recombinant INUO purified to 0.35 μg/mL was incubated with 800 mM sucrose at 50° C. in 50 mM universal buffer, pH 7.0, to produce FOS. Depletion of sucrose and formation of glucose and fructose were monitored using HPLC (see above). Produced FOS was analyzed by TLC (data not shown) and by HPLC. FIG. 3 depicts the results of IOS formation by recombinant INUO, measured by HPLC and high performance anion-exchange chromatographic (HPAEC).

FOS was precipitated from the incubation mixture using two volumes of 96% cold ethanol. After overnight incubation at 4° C., FOS was separated by centrifugation at 900×g for 60 min. The FOS was precipitated after they were dissolved in MilliQ water. This process was repeated two more times, and the FOS was finally freeze-dried.

A larger batch of FOS were produced by incubating 200 mL of INUO at 1.79 μg/mL in 800 mM sucrose, 75 mM of universal buffer, pH 7.0, in a total volume of 2 L. The mixture was incubated at 50° C. with gentle shaking (30 rpm). Depletion of sucrose was monitored by HPLC, and product formation was measured over time by HPAEC.

(ii) Thin Layer Chromatography (TLC):

To characterize FOS products, 1 μL of 2× diluted incubation samples or 1 μL of purified, freeze-dried FOS samples (1 mg/20 μL) were applied to TLC (Silica gel 60 $F_{254}$; Merck, Germany) overnight using 1-butanol:ethanol:water (5:5:3) as the mobile phase. The plates were air-dried, sprayed with 45:45:10 $MeOH:H_2O:H_2SO_4$ developing solution, and developed at 110° C. for approximately 15 min.

Degradation of freeze-dried FOS product by exo-inulinase was carried out as follows: 10 μL sample and 2 μL. *Aspergillus niger* inulinase (Sigma, St. Louis, MO) (from a stock solution of 10 mg of enzyme at 22 U/mg dissolved in 1 mL of 0.1 M sodium acetate buffer, pH 4.5) were incubation for 15 minutes at room temperature and run on a TLC plate as described above.

(iii) High Performance Anion-Exchange Chromatographic (HPAEC) Analysis:

Enzyme incubation reactions of INUO with sucrose and purified fructo oligosaccharides (0.1 mg/ml), after appropriately diluted, were analyzed by high performance anion exchange chromatography coupled to pulsed amperometric detection (HPAEC-PAD—Dionex ICS-5000). Glucose, fructose, sucrose, kestose, nystose, fructosylnystose, and chicory inulin (Sigma, Megazyme) were used as standards. Sugars were separated using a CarbopacPA200 column (Thermo Scientific) with ultrapure water (eluent A), 1 M NaOH (eluent B), and 0.5 M NaAc (eluent C) as solvents at a flow rate of 0.50 mL/min, injection volume 5-10 μL, column temperature 30° C., and detector temperature 25° C. The following gradient of eluents A, B, and C was used:

eluent A (0 min, 89%); (55 min, 35%); (60.9 min, 25%); (61 min, 15%);

eluent B (0 min, 10%); (55 min, 10%); (60.9 min, 10%); (61 min, 20%); and eluent C (0 min, 1%); (55 min, 55%); (60.9 min, 65%); (61 min, 65%).

Detection was performed with an electrochemical detector (Thermo Scientific) with an Au working electrode and an Ag/AgCl reference electrode. Waveform: Gold Standard PAD (standard quad potential): +0.1 Volt (0-0.40 s); −2.0 Volt (0.41-0.42 s); 0.6 Volt (0.43 s); −0.1 Volt (0.44-0.50 s). Data were integrated using Chromeleon software (Thermo Scientific).

(iv) Nuclear Magnetic Resonance (NMR):

For NMR spectroscopy, approximately 1% w/v samples were dissolved in 99.9 atom percent $D_2O$ (Sigma-Aldrich) and stirred at 50° C. for 20 minutes prior to transferring to NMR tubes. Chicory inulin and levan from *Zymomonas mobilis* (Sigma) were used as controls. One-dimensional $^1$H-NMR spectra were recorded on a 600 MHz Avance III NMR spectrometer (Bruker) in a double resonance broad band probe at 300 K. Chemical shifts are expressed in ppm relative to the methyl group of external acetone ($\delta$=2.225). $^1$H NMR spectra were recorded with a spectral width of 10,000 Hz in 32 k complex data points. The HOD signal (i.e., from water in which one proton is exchanged for a deuterium) was suppressed by excitation sculpting. Prior to Fourier transformation, the time-domain data were apodized with an exponential function, corresponding to a 1 Hz line broadening.

Two-dimensional $^1$H-$^{13}$C sensitivity-enhanced, multiplicity edited heteronuclear single quantum coherence (HSQC) spectroscopy using standard parameters was carried out at a $^1$H frequency of 600.13 MHz and a $^{13}$C frequency of 150.9 MHz. Spectra were recorded with a spectral width of 7211 Hz for F2 and 25 kHz for F1. Spectra were acquired with 16 transients and 256 indirect increments using a d1 of 2 sec and 141 ms acquisition time.

(v) Methylation of FOS Samples:

FOS samples were permethylated using $CH_3I$ and solid NaOH in dimethylsulfoxide. See Pettolino et al. (2012) *Nat.*

*Protoc.* 7: 1590-1607. After hydrolysis with 2 M trifluoroacetic acid (2 h, 120° C.), the partially methylated monosaccharides were reduced with NaBD$_4$ (overnight, at room temperature). Neutralization with acetic acid and removal of boric acid by co-evaporation with methanol, followed by acetylation with acetic anhydride-trifluoroacetic acid (25:23 v/v, 20 min, 50° C.), yielded a mixture of partially methylated alditol acetates. These products were analyzed by gas-liquid chromatography (GLC) combined with electron-impact mass spectrometry (EI/MS). GLC EI/MS was performed on a GC 7890/MSD 5973 system (Agilent Technologies, Little Falls, DE) equipped with an RTx-2330 column (30 m×0.25 mm×0.2 µm film thickness) (Restek Corp., Bellefonte, PA), using a temperature gradient of 80° C. (2 min) to 170° C. (0 min) at 30° C./min followed by 4° C./min to 240° C. (20 min).

(vi) FOS Molecular Mass Determination:

(a) LiNO$_3$ eluent: Molecular masses of the FOS were determined by high performance size exclusion chromatography (HPSEC) coupled on-line with a multi angle laser light scattering (MALLS) and differential refractive index (RI) detection (Optilab rEX, Wyatt Technology Corp., Santa Barbara, CA) operating at 40° C. 1-2 mg of sample was dissolved in 50 mM LiNO$_3$ and filtered through a 0.45 µm filter (Mini Spike, BBraun Melsungen AG, Germany). 100 µL sample was injected on HPLC (Gynkotek HPLC pump P580A, Gemini BV Laboratory, NL) equipped with a PSS SUPREMA-LUX 1000 Å and PSS SUPREMA-LUX 3000 Å gel permeation chromatography (GPC) column operating at 40° C. As eluent, 50 mM LiNO$_3$ with 200 ppm NaN$_3$ was used at a flow rate of 0.6 mL/min. A DAWN-EOS laser photometer He—Ne ($\lambda$=690 nm) (Wyatt Technology, Santa Barbara, CA) equipped with a K5 flow cell and 18 detectors at angles ranging from 12.8° to 164.7° was used as MALLS detector.

(b) Aqueous eluent: Molecular masses of the FOS were determined by a multi-detector size exclusion chromatography method using PL-GPC220 integrated size-exclusion chromatography (SEC) system from Agilent Technologies equipped with differential refractometer and differential capillary viscometer, and additionally coupled with MALLS photometer DAWN-HELEOS-II (Wyatt Technology, Santa Barbara, CA). Samples were dissolved in Tris buffer (0.05 M hydroxymethyl aminomethane and 0.15 M sodium chloride, pH 7.6) at concentration 5 mg/mL and injected into the SEC system with 100 µL injection volume. The solution was filtered through a 0.45 µm hydrophilic polytetrafluoroethylene (PTFE) filter (Millipore® Millex® LCR) prior to injection. Two TKSgel GMPW-XL (pore size from 100 to 1000 Å) GPC columns, as well as a guard column, operating at 30° C. were used for separation. Tris buffer with 200 ppm NaN$_3$ was used as the eluent at a flow rate of 0.5 mL/min. The data were processed using ASTRA v. 6.2 software (Wyatt Technology Corp., Santa Barbara, CA) without column calibration.

Production and Characterization of the FOS Synthesized by INUO

The recombinant INUO synthesized about 100 g of FOS from 200 mL of *B. subtilis* culture after a few hours of incubation with sucrose at a starting concentration of 800 mM. See FIG. 3. Under the conditions tested, the INUO enzyme had very low hydrolytic activity, and most of the fructose was incorporated in FOS. TLC analysis of isolated product showed that the purified recombinant INUO synthesized a range of FOS in addition to larger FOS>10 not separating under the TLC conditions used.

The INUO enzyme synthesizes only IOS with a GF range of GF10-GF25 and a peak at GF16-GF17. HPAEC analysis of incubation reaction of INUO with sucrose compared to chicory inulin (FIG. 4) showed that the majority of the FOS peaks were eluting at a similar position. Chicory inulin showed intermediate peaks next to the GFn peaks and also a broader distribution than INUO. The isolated FOS produced by INUO were degraded when exo-inulinase was added as analyzed by TLC (FIG. 5) and HPAEC (data not shown). These observations indicate that the synthesized FOS material was of the inulin type (i.e., β-(2→1) linked fructose units).

Figure 6:
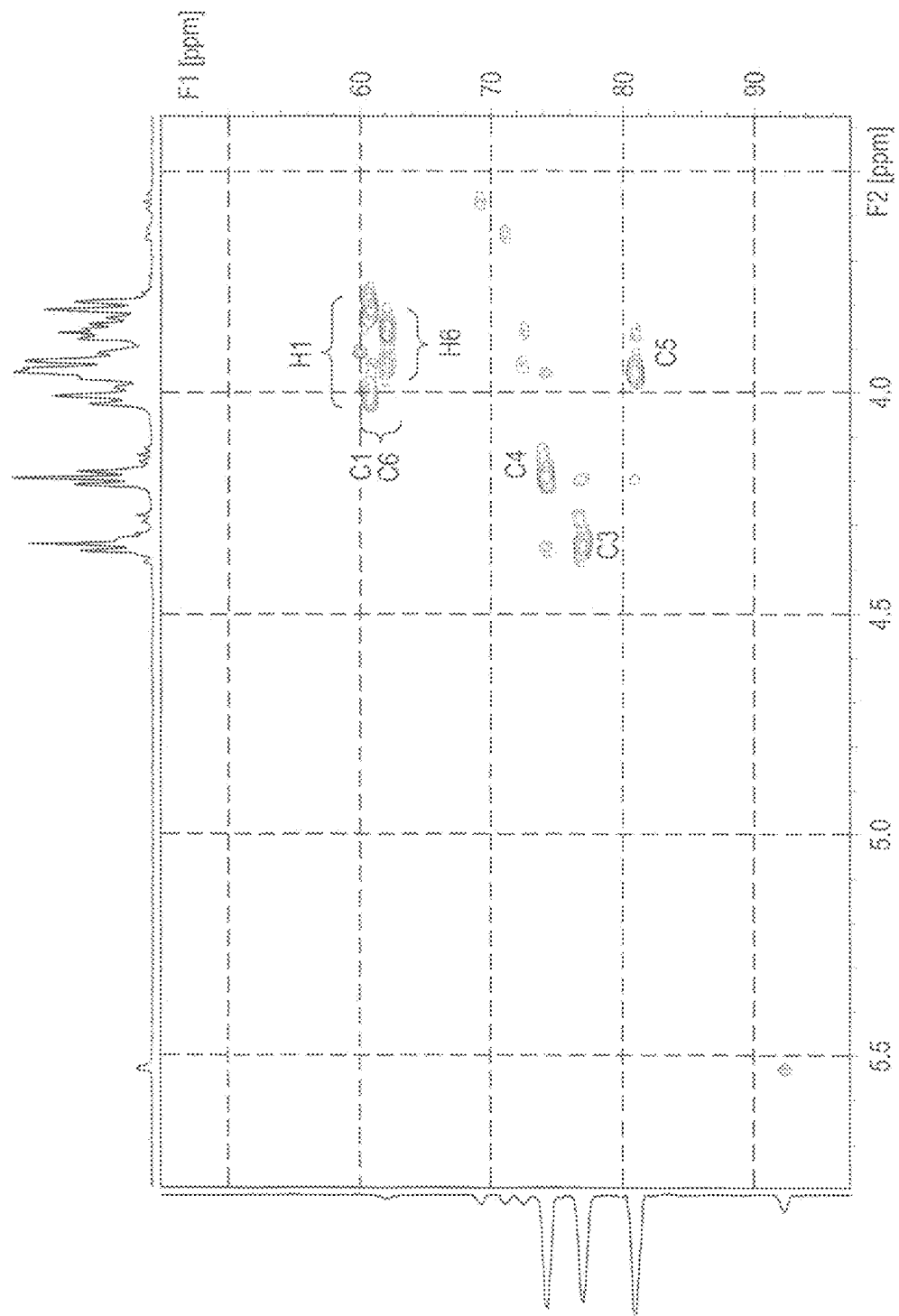
FIG. 6 depicts 600 MHz 2D $^1$H-$^{13}$C sensitivity enhanced multiplicity edited heteronuclear single quantum coherence (HSQC) spectroscopy of the ethanol precipitated FOS made by purified recombinant INUO. Chemical shifts are given in parts per million. The $^1$H signal is given relative to external acetone ($^1$H, δ=2.225).

Comparison of the 2D NMR $^1$H-$^{13}$C HSQC spectrum of inulin from chicory, levan from *Z. mobilis*, and the FOS synthesized by INUO showed that the spectrum of the FOS synthesized by INUO corresponds with β-(2→1) linked fructose units, typical for the structure found in inulin (FIG. 6). Furthermore, GC-MS analysis confirmed the presence of >95% β-(2→1) linked fructose units.

Figure 4:
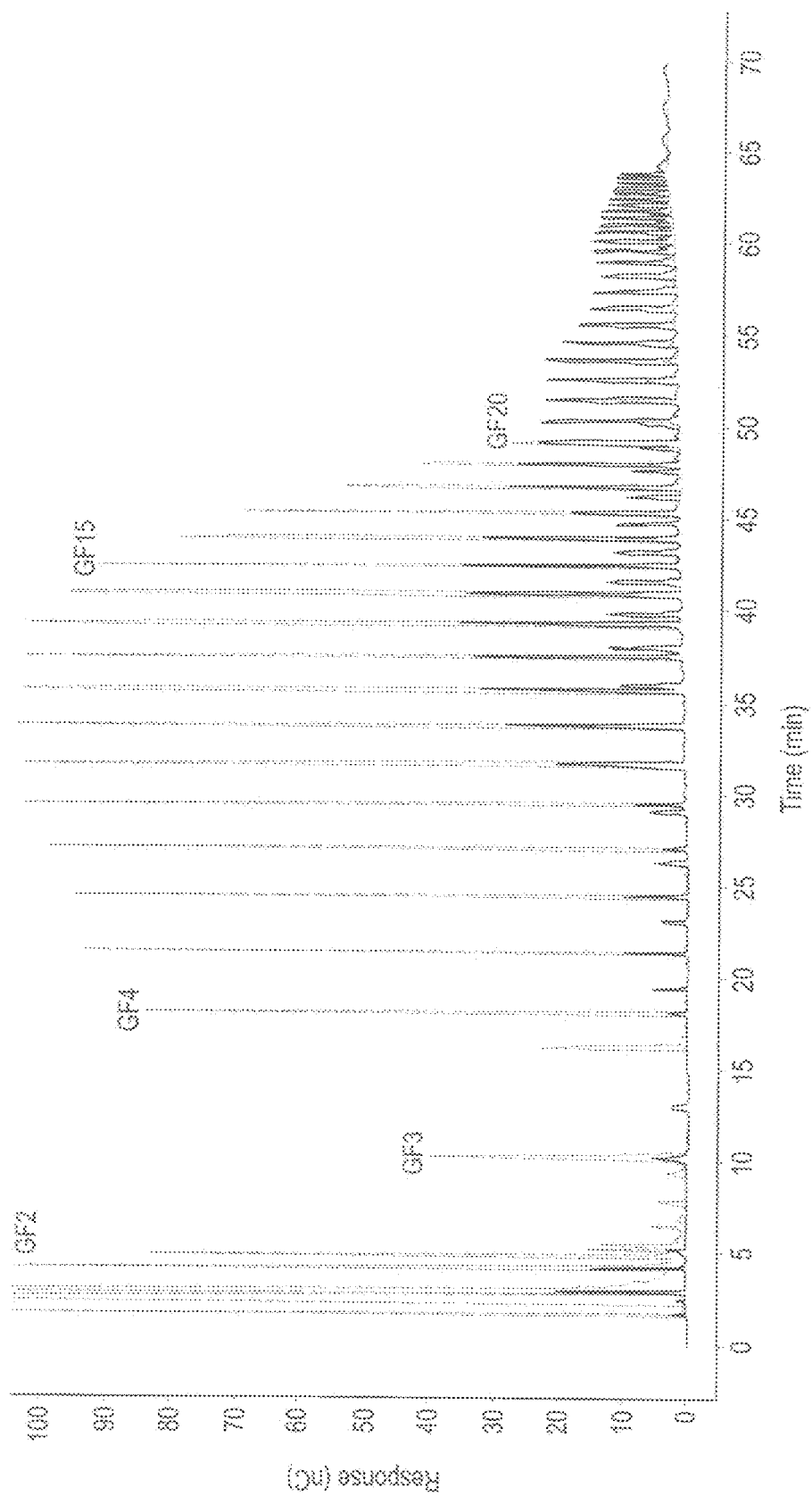
FIG. 4 depicts HPAEC analysis of INUO reaction products (dotted line) formed upon incubation of 0.35 µg/mL purified INUO enzyme with 800 mM sucrose and chicory inulin (solid line) (GF2=1-kestose; GF3=1-nystose; and GF4=$1^F$-fructofuranosylnystose).
Figure 5:
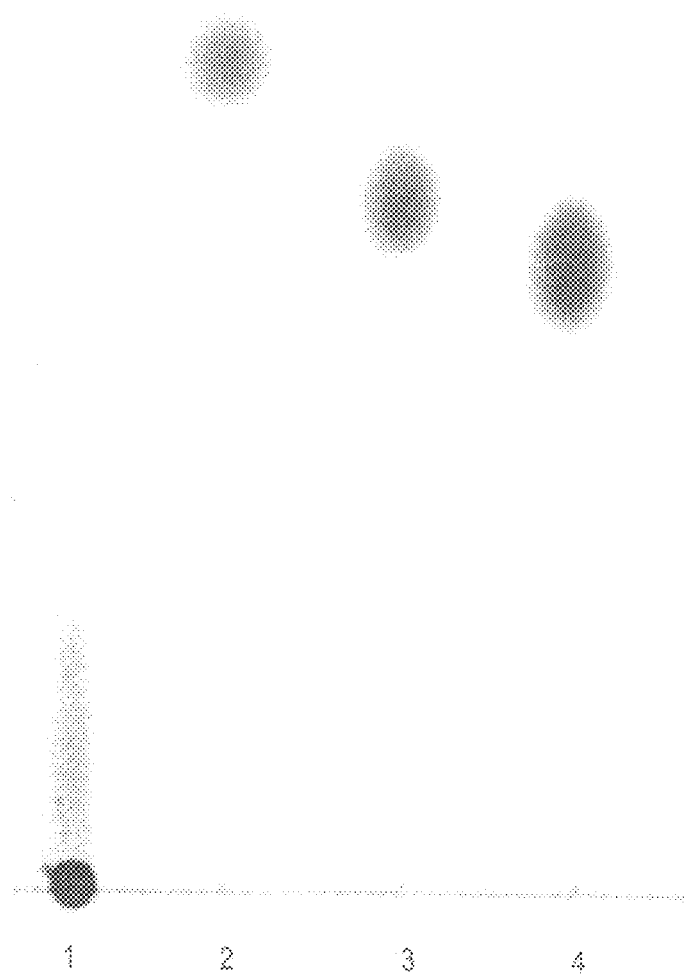
FIG. 5 depicts TLC analysis of (1) precipitated and freeze-dried reaction product of purified INUO, (2) reaction product of INUO degraded by inulinase, (3) 1-kestose (GF2) and (4) 1-nystose (GF3).
Figure 7:
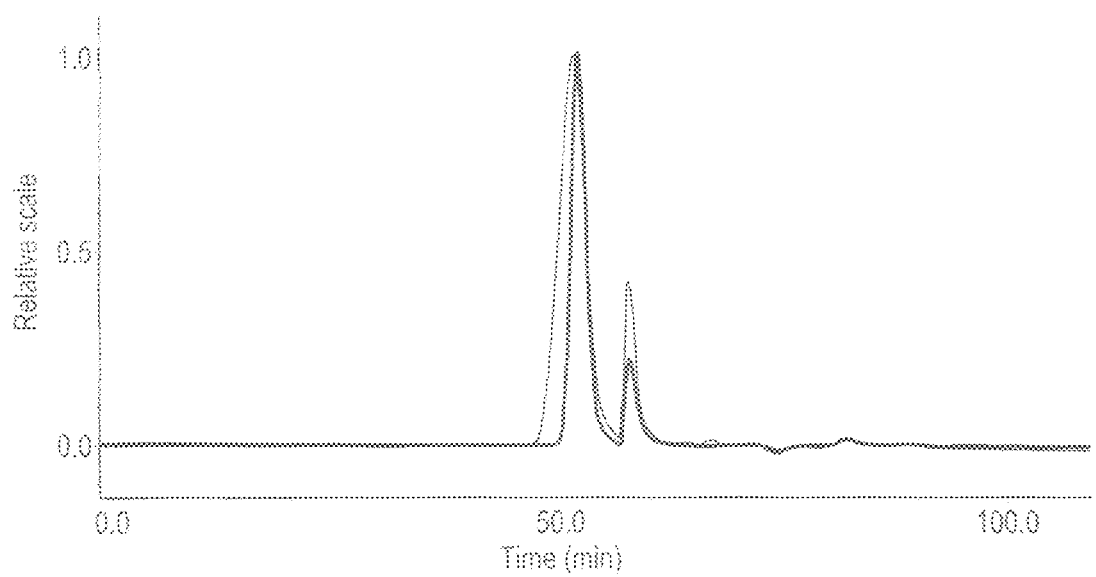
FIG. 7 depicts LiNO$_3$ high performance size exclusion chromatography (HPSEC)-multi angle laser light scattering (MALLS)-refractive index (RI) spectra of inulin synthesized by INUO (black line) and sigma chicory inulin (grey line).

The size of the FOS material synthesized by INUO as determined by LiNO$_3$ HPSEC was about 3 kDa. This size was similar to chicory inulin, which showed a broader distribution (FIG. 7) corroborating the results obtained by HPAEC (FIG. 4).

The following masses were determined using aqueous HPSEC for FOS produced by INUO and for chicory inulin: Mn 3.2/3.9 kDa; Mw 3.3/4.6; PDI Mw/Mn 1.002/1.194 and Mp 3.3/4.0, respectively. The polydispersity of the INUO product was remarkably small and even narrower than that of chicory inulin.

```
SEQUENCE LISTING:
Primer sequence
                                          SEQ ID NO: 1
5'-ctcattctgcagctagcgcaACCTCA

GACTGGGATGCTGAAGATGAT-3'

Primer sequence
                                          SEQ ID NO: 2
5'-CGCAGATATCGTTAACTCAACGATAG

GCACCGAATGGTCTGAT-3'

Nucleotide sequence of the B. agradhaerans
WDG185 ftf gene encoding InuO:
                                          SEQ ID NO: 3
ATGGGAATTAAAAAAACATATGGTGATTTTTTGAA

ATGGGGAGTATGCACGGCGATTTTAGGAAGCTCTC

TGATGGCCAGCACCGTTTTTGCCACCTCAGACTGG

GATGCTGAAGATGATTACACCGCGGTTTGGACACG

TCAGCAAGCTGAGAATGTGGCTTTGACGAAAGATA

CGACGGCGCCTCTTTTGGAGACGGATGAGGATTTT

GAACTCGTTGCTCCCGATAAATGGGTTTGGGACAC

GTGGCCACTTCAGAACAGGGACGGTTCACTTGCTC

AGGTGAATGGGTACACAATTGCATTTGCCTTGGTT

GCTCCACGAGATTTAGGTTGGGGGGAGCGTCATAC

TGAGGCTAGAATCGGCATGTTCTACTCCAAAGACG

GAAAAGACTGGACTTACGCAGGTATTCCATATGAC

TATGACAAAGCTTACGGTCACATGCAGTGGGCTGG
```

```
TTCCGCCATGTTGGACAAGGATGGAAAAGTACATT
TCTTTTATACTGCAACAGGACGTAAGGATAATTCT
GAATATTTTGATCAACCAGGATGGGAGCCAATGGC
TGAGCAACGCCTTGCTAAAACGACGTTTGACATCA
GCGCAGACAAAGACGGCGTTCATTTGACTAAAGAA
GATGAACATCAGATCATGCTTGAGGCAGACGGGA
ATATTACGAAACGCTTGGCCAATGGGAAGTAACG
GAAATATCATCAGTGCGTTTCGTGATCCGTTTTC
TTTCAGGACCCTAACACAGGGGAAGAATACATTAT
TTGGGAAGGACAGGCAGGCCCTAAAAGCAATGGTC
TGAAGCCGGAAAATATCGGTGATGAAGCATATCGT
AAAAACGCTAATGTTCCAGATAGAGCGGAACTTTA
CAACGGCAACATTGGGATAGCCAAAGTACTTGACG
AGGATGTCTCCGAACTAAAAATGTTGCCACCACTT
CTCGAATCAATTGGGGTCAATCATCAACTGGAACG
TCCGCATGTAGTGGTGGACGGTGACACGTACTACT
TGTTAACCATCAGCCATACCTTCACATACGCACCT
GGTTTGACTGGTCCAGAAGGTTTGTACGGCTTTGT
CAATGAAGGTGGGTTACGAGGTGATTACGAACCTC
TCAACGACGGTGGTCTAGTGATTGGTAATCCTGCT
GAAAGCCCGGGTCAGGCCTATTCTTGGTGGGTAGC
TCCAGACGGACAGGTTATCAGCTTCATCAATGAAC
CTCTTGATGAGAATGGAGAAGTCCAATTCGTGGGT
ACTTTCGCGCCGACACTACAACTGTCCTTTGACGG
TGATCAAACAAAAATTGAGAAGGAAATGGGTTATG
GAGAAATCAGACCATTCGGTGCCTATCGT

Amino acid sequence of
B. agradhaerans InuO
                                    SEQ ID NO: 4
MGIKKTYGDFLKWGVCTAILGSSLMASTVFATSDW
DAEDDYTAVWTRQQAENVALTKDTTAPLLETDEDF
ELVAPDKWVWDTWPLQNRDGSLAQVNGYTIAFALV
APRDLGWGERHTEARIGMFYSKDGKDWTYAGIPYD
YDKAYGHMQWAGSAMLDKDGKVHFFYTATGRKDNS
EYFDQPGWEPMAEQRLAKTTFDISADKDGVHLTKE
DEHQIMLEADGEYYETLGQWGSNGNIISAFRDPFF
FQDPNTGEEYIIWEGQAGPKSNGLKPENIGDEAYR
KNANVPDRAELYNGNIGIAKVLDEDVSELKMPPL
LESIGVNHQLERPHVVVDGDTYYLLTISHTFTYAP
GLTGPEGLYGFVNEGGLRGDYEPLNDGGLVIGNPA
ESPGQAYSWWVAPDGQVISFINEPLDENGEVQFVG
TFAPTLQLSFDGDQTKIEKEMGYGEIRPFGAYR Conserved catalytic motif of
GH68 enzymes
                                    SEQ ID NO: 5
(V/L)WD(T/S)(W/M)

Conserved catalytic motif of
GH68 enzymes
                                    SEQ ID NO: 6
D(E/Q)(I/T)ER Amino acid sequence of B. subtilis
SACB
                                    SEQ ID NO: 7
MNIKKFAKQATVLTFTTALLAGGATQAFAKETNQK
PYKETYGISHITRHDMLQIPEQQKNEKYQVPEFDS
STIKNISSAKGLDVWDSWPLQNADGTVANYHGYHI
VFALAGDPKNADDTSIYMFYQKVGETSIDSWKNAG
RVFKDSDKFDANDSILKDQTQEWSGSATFTSDGKI
RLFYTDFSGKHYGKQTLTTAQVNVSASDSSLNING
VEDYKSIFDGDGKTYQNVQQFIDEGNYSSGDNHTL
RDPHYVEDKGHKYLVFEANTGTEDGYQGEESLFNK
AYYGKSTSFFRQESQKLLQSDKKRTAELANGALGM
IELNDDYTLKKVMKPLIASNTVTDEIERANVFKMN
GKWYLFTDSRGSKMTIDGITSNDIYMLGYVSNSLT
GPYKPLNKTGLVLKMDLDPNDVTFTYSHFAVPQAK
GNNVVITSYMTNRGFYADKQSTFAPSFLLNIKGKK
TSVVKDSILEQGQLTVNK Amino acid sequence of B. megaterium
D5M319 SACB
                                    SEQ ID NO: 8
MKMKRVAKHTTAATLAAALLVGGGYQTFAKGNDSK
DFNNSYGISHITRDNMVKIPQQQNSDQFKVPAFDE
STIKNIASAKGKNASGNTIDLDVWDSWPLQNADGT
VATYHGYQIVFALAGDPKDSNDTSVYLFYKKAGDK
SIDSWKNAGRVFKDSDKFVPNDPHLKNQTQEWSGS
GTLTKDGKVRLFYTDYSGKQYGKQTLTTAQVNMSQ
PNDNTLKVDGVEDYKSIFDGDGKIYQTVQQFIDEG
GYDTGDNHTLRDPHYIEDNGHKYLVFEANTGTEDG
YQGEDSLYNRAYYGGNNPFFQSEKKKLLEGSNKEK
ASLANGALGIIELNDDYTLKKVMKPLITSNTVTDE
IERANIFKKDGKWYLFTDSRGSKMTIDGIGQDDVY
MLGYVSNTLTGKYKPLNDTGLVLHMDLDPNDKTFT
YSHFAVPQTKGDNVVITSYMTNRGFYEDNHSTFAP
SFLVNIDGSKTSVVKDRVLEQGQLTVDED Amino acid sequence of
Ln. mesenteroides
NRRL B-512 LEVS
                                    SEQ ID NO: 9
MRKKLYKAGKLWVAGAAVRLQSWAPNIVSADTTNS
TTTADATTTSSATESSISSTESDDNKVDTSNTDAV
TVTTNSDDSNSNSAETSNSDAKVTSNNTAQKDEAI
```

KAETTNNQDTTSTTAVAETKTAVNTSESESGSNNE
QLAETATDNAKVNDASSQKQSTPSVEKLDDSVSKD
LNSKTTVVTKNADGTSTTNMTYANLKDVADNIASL
NPDTSVPYFNADAIKNLPAMTTADAQTGQIQDLDV
WDSWALQDAKTGAVANYHGYNIVFALAGYPKEDND
QHIYMLYTKYGDTALNNWKNAGPVFGFNAKWNEQQ
WSGSATVNDDDSIQLFYTKTDQPNTVQRLATANLS
MTYTDTEVYVAKVNDDHVLFAGDGEYYQTLQQWVD
AGYYTTGDNFTMRDPHVIEVNGERYLAFEANTGTN
NYQSDDAVNDDTYYGGTEEFNQQAKVDTLQNPDKL
KLSKKANGAIGLIKLTKDQNNPTVAQVYSPLLAAN
GITDEIERANIVPLNGKFYLFTDTRLSKSVVPTAD
FNINVGMMGYVSDSLFGPYTPLNGSGSVVTGTQLF
TSRTDTYSYYAVPVEGRSDLLLVTSYMSNRNEKAG
TGMNATFAPSFLIQISADGMSTKVLDTVLAQGTWT
YDGKSASVEELVGNKATSELTDMKIGWVDNKFYVD
NELANGYVYDYINTSYYLFKNGVRLSGVQTYANSY
YYFDPVTYKRVDNEIHQDNTGKKYYFGNDGRVKQG
QFAVNGVAYNFGNDKTYYERGFASGYLQDVTDNNQ
WYWFESGKKYTGFRYYMGTYYFFETGQRQESKWET
AWGMKYYVGTDGRAVQGVQIIDGQAYDFGTNGTFN
LKGTASGYLSPSLSTANGGYNWFENGKPYTGFRY
YEGTYYWFVNGVRQNAGWREAWGMKYYTDASGRAL
QGIQIIDGQAYDFGTNGTYNLKSAASGYLYSPSYS
KANGGYNWFENGKPYTGFRYYMGTYYWFVNGVRQN
AGWREAWGKKYYTDANGRALQGIQKIDGQQYNFGN
DGTYYLR

Amino acid sequence of L. gasseri
20243 INUGA
SEQ ID NO: 10
MLENKNHKKMSLSGKSLLMGTLSTAAIVLSASTVN
AATTNADNVNENKTVAVSTTTSANNKNNNQVNSSS
EKSVDTKAEKATTVTSAATKEVKADAV
NTSPVNNVKAATTSTTTTKETVDGTEKTPVNSSAD
VKKNDAVKQDEKAATSFKTNTEEKANETSTKTASN
DNKAELKGQIKDIVKESDVDTSKLTNDQINELNKI
NFSKEAKSGTQLTYSDFKKIAKTLIEQDARYAIPF
FNASKIKNMPAAKTMDAQTGKVEDLEIWDSWPVQD
AKTGYVSNWNGYQLVVGMMGVPNTNDNHIYLLYNK
YGDNNFNNWKNAGPIFGLGTPVIQQWSGSATLNKD
GSIQLYYTKVDTSDNNTNHQKIASATVYLNLEKDQ
DKISIAHVDNDHIVFEGDGYHYQTYNQWKKTNKGA
DNIAMRDAHVIDDKDGNRYLVFEASTGTENYQGAD
QIYQWLNYGGTNKDNLGDFFQILSNSDIKDRAKWS
NAAIGIIKLNNDTKNPGVEKVYTPFISSPMVSDEI
ERPDVVRLGNKYYLFAATRLNRGSNDDAWMAANKA
VGDNVAMIGYVSDNLTHGYVPLNESGVVLTASVPA
NWRTATYSYYAVPVEGRDDQLLITSYITNRGEVAG
KGMHATWAPSFLLQINPDNTTTVLAKMTN Amino acid sequence of L. gasseri
20604 INUGB
SEQ ID NO: 11
MLENKNHKKMSLSGKSLLMGTLSTAAIVLSASTVN
AATTNADNVTKNQTVAVSATTTNNETNNQVSSSSE
KTADSKTEKDTNLTSAATKEVKADAAKTTSPVNNV
KTVADTTTTTKETTDNTEKSPVNFSADVKKNDAVK
QDEKAATAVKANTEVKANETSTKSASKDNKAELKG
QIKDIVKESGVDTSKLTDDQINELNKISFSKEAKS
GTQLTYSDFKKIAKTLIEQDARYAVPFFNASKIKN
MPAAKTLDAQTGKVEDLEIWDSWPVQDAKTGYVSN
WNGYQLVIGMMGVPNTNDNHIYLLYNKYGDNNFNN
WKNAGPIFGLGTPVIQQWSGSATLNKDGSIQLYYT
KVDTSDNNTNHQKIASATVYLNLEKNQDKISIAHV
DNDHIVFEGDGYHYQTYNQWKKTNKGADNIAMRDA
HVIDDKDGNRYLVFEASTGTENYQGADQIYQWLNY
GGTNKDNLGDFLQILSNSDIKDRAKWSNAAIGIIK
LNNDTKNPGVEKVYTPLISAPMVSDEIERPDVVRL
GNKYYLFAATRLNRGSNDDAWMAANKAVGDNVAMI
GYVSDNLTHGYVPLNESGVVLTASVPANWRTATYS
YYAVPVEGRDDQLLITSYITNRGEVAGKGMHATWA
PSFLLQINPDNTTTVLAKMTNQGDWIWDDSSENAD
MMGVLEKDAPNSAALPGEWGKPVDWDLIGGYNLKP
HQPVTPIPNVPTTPEKPENPTTPNTPDTPHTPTTP
NTPDTPRTPEVPTTPVKKTTQSELRS Amino acid sequence of L. jonsonii
NCC533INUJ
SEQ ID NO: 12
MLENKNHKKISLSGKSLLMGTLSTAAIVLSASTAN
AATINADNVNENQTVEVTASSVNNENNKQVTEKDS
ADKSTSDVAEDANTKKSNENTETTEKNTQTVVTNA
PVSDVKNTNTVTAETPVDKVVNNSDQKTTNAATTD
TKKDDVKQVEKKDSVDKTNAEENKDSSVKPAENAT
KAELKGQVKDIVEESGVDTSKLTNDQINELNKINF
SKEAKSGTQLTYNDFKKIAKTLIEQDARYAIPFFN
ASKIKNMPAAKTLDAQSGKVEDLEIWDSWPVQDAK -continued

TGYVSNWNGYQLVIGMMGVPNVNDNHIYLLYNKYG

DNDFNHWKNAGPIFGLGTPVIQQWSGSATLNKDGS

IQLYYTKVDTSDNNTNHQKLASATVYLNLEKDQDK

ISIAHVDNDHIVFEGDGYHYQTYDQWKETNKGADN

IAMRDAHVIDDDNGNRYLVFEASTGTENYQGDDQI

YQWLNYGGTNKDNLGDFFQILSNSDIKDRAKWSNA

AIGIIKLNDDVKNPSVAKVYSPLISAPMVSDEIER

PDVVKLGNKYYLFAATRLNRGSNDDAWMATNKAVG

DNVAMIGYVSDNLTHGYVPLNESGVVLTASVPANW

RTATYSYYAVPVEGRDDQLLITSYITNRGEVAGKG

MHATWAPSFLLQINPDNTTTVLAKMTNQGDWIWDD

SSENPDMMGVLEKDAPNSAALPGEWGKPVDWDLIG

GYNLKPHQPVTPIPNVPTTPETPTTPDKPEVPTTP

EVPTTPETPTPEAPKNPVKKTSQSKLPKAGDKNSF

AAVVLGAVSSILGAVGLTGVSKRKRNN

Amino acid sequence of *L. reuter* TMW1.106 INU

SEQ ID NO: 13

MLERKEHKKMYKSGKNWAVVTLSTAALVFGATTVN

ASADTNTENNDSSTVHVTTGDNDIAVKSAILGSGQ

VSAASDATIKNSANANSASSAANTQNSNSQVASSA

ATTSSTSSAASSNNTDSKAAQENANTAKNDDTQKA

APANESSEAKNEPAVNVNDSSAAKNDDQQSSKKNT

TAKLNKDAENVVKKAGIDPNSLTDDQIKALNKMNX

XKAAKXGTQMTYNDFQKXADTLIKQDGRYTVPFFK

ASEIKNMPAATTKDAQTNTIEPLDVWDSWPVQDVR

TGQVANWNGYQLVIAMMGIPNQNDNHIYLLYNKYG

DNELSHWKNAGPIFGYNSTAVSQEWSGSAVLNSDN

SIQLFYTRVDTSDNNTNHQKIASATLYLTDNNGNV

SLAQVANDHIVFEGDGYYYQTYDQWKATNKGADNI

AMRDAHVIEDDNGDRYLVFEASTGLENYQGENQIY

NWLNYGGDDAFNIKSLFRILSNDDIKSRATWANAA

IGILKLNKDEKNPKVAELYSPLISAPMVSDEIERP

NVVKLGNKYYLFAATRLNRGSNDDTWMNANYAVGD

NVAMVGYVADSLTGSYKPLNDSGVVLTASVPANWR

TATYSYYAVPVAGKDDQVLVTSYMTNRNGVAGKGM

DSTWAPSFLLQINPDNTTTVLAKMTNQGDWIWDDS

SENLDMIGDLDSAALPGERDKPVDWDLIGYGLKPH

DPATPNDPETPTTPETPETPNTPKTPKTPENPGTP

QTPNTPNTPEIPLTPETPKQPETQTNNRLPQTGNN

ANKAMIGLGMGTLLSMFGLAGINKRRFN

-continued

Amino acid sequence of *L. reuter* 121 INU

SEQ ID NO: 14

MLERKEHKKMYKSGKNWAVVTLSTAALVFGATTVN

ASADTNIENNDSSTVQVTTGDNDIAVKSVTLGSGQ

VSAASDTTIRTSANANSASSAANTQNSNSQVASSA

AITSSTSSAASSNNTDSKAAQENTNTAKNDDTQKA

APANESSEAKNEPAVNVNDSSAAKNDDQQSSKKNT

TAKLNKDAENVVKKAGIDPNSLTDDQIKALNKMNF

SKAAKSGTQMTYNDFQKIADTLIKQDGRYTVPFFK

ASEIKNMPAATTKDAQTNTIEPLDVWDSWPVQDVR

TGQVANWNGYQLVIAMMGIPNQNDNHIYLLYNKYG

DNELSHWKNVGPIFGYNSTAVSQEWSGSAVLNSDN

SIQLFYTRVDTSDNNTNHQKIASATLYLTDNNGNV

SLAQVANDHIVFEGDGYYYQTYDQWKATNKGADNI

AMRDAHVIEDDNGDRYLVFEASTGLENYQGEDQIY

NWLNYGGDDAFNIKSLFRILSNDDIKSRATWANAA

IGILKLNKDEKNPKVAELYSPLISAPMVSDEIERP

NVVKLGNKYYLFAATRLNRGSNDDAWMNANYAVGD

NVAMVGYVADSLTGSYKPLNDSGVVLTASVPANWR

TATYSYYAVPVAGKDDQVLVTSYMTNRNGVAGKGM

DSTWAPSFLLQINPDNTTTVLAKMTNQGDWIWDDS

SENLDMIGDLDSAALPGERDKPVDWDLIGYGLKPH

DPATPNDPETPTTPETPETPNTPKTPKTPENPGTP

QTPNTPNTPEIPLTPETPKQPETQTNNRLPQTGNN

ANKAMIGLGMGTLLSMFGLAEINKRRFN

Amino acid sequence of *L. reuter* 121 LEV

SEQ ID NO: 15

MEYKEHKKMYKVGKNWAVATLVSASILMGGVVTAH

ADQVESNNYNGVAEVNTERQANGQIGVDGKIISAN

SNTTSGSTNQESSATNNTENAVVNESKNTNNTENA

VVNENKNTNNTENAVVNENKNTNNTENDNSQLKLT

NNEQPSAATQANLKKLNPQAAKAVQNAKIDAGSLT

DDQINELNKINFSKSAEKGAKLTFKDLEGIGNAIV

KQDPQYAIPYFNAKEIKNMPATYTVDAQTGKMAHL

DVWDSWPVQDPVTGYVSNYKGYQLVIAMMGIPNSP

TGDNHIYLLYNKYGDNDFSHWRNAGSIFGTKETNV

FQEWSGSAIVNDDGTIQLFFTSNDTSDYKLNDQRL

ATATLNLNVDDNGVSIKSVDNYQVLFEGDGFHYQT

YEQFANGKDRENDDYCLRDPHVVQLENGDRYLVFE

ANTGTEDYQSDDQIYNWANYGGDDAFNIKSFFKLL

NNKKDRELAGLANGALGILKLTNNQSKPKVEEVYS

```
                         -continued
PLVSTLMASDEVERPNVVKLGDKYYLFSVTRVSRG

SDRELTAKDNTIVGDNVAMIGYVSDSLMGKYKPLN

NSGVVLTASVPANWRTATYSYYAVPVAGHPDQVLI

TSYMSNKDFASGEGNYATWAPSFLVQINPDDTTTV

LARATNQGDWVWDDSSRNDNMLGVLKEGAANSAAL

PGEWGKPVDWSLINRSSGLGLKPHQPVQPKIDQPD

QQPSGQNTKNVTPGNGDKPAGKATPDNTNIDPSAQ

PSGQNTNIDPSAQPSGQNTKNVTPGNEKQGKNTDA

KQLPQTGNKSGLAGLYAGSLLALFGLAAIEKRHA

Amino acid sequence of S. mutans
GS-5 INU
                                SEQ ID NO: 16
METKVRKKMYKKGKFWVVATITTAMLTGIGLSSVQ

ADEANSTQVSSELAERSQVQENTTASS

SAAENQAKTEVQETPSTNPAAATVENTDQTTKVIT

DNAAVESKASKTKDQAATVTKTAASTPEVGQTNEK

DKAKATKEADITTPKNTIDEYGLTEQARKIATEAG

INLSSLTQKQVEALNKVKLTSDAQTGHQMTYQEFD

KIAQTLIAQDERYAIPYFNAKAIKNMKAATTRDAQ

TGQIADLDVWDSWPVQDAKTGEVINWNGYQLVVAM

MGIPNTNDNHIYLLYNKYGDNNFDHWKNAGSIFGY

NETPLTQEWSGSATVNEDGSLQLFYTKVDTSDKNS

NNQRLATATVNLGFDDQDVRILSVENDKVLTPEGV

MAYHYQSYQQWRSTFTGADNIAMRDPHVIEDENGD

RYLVFEASTGTENYQGEDQIYNFTNYGGSSAYNVK

SLFRELDDQDMYNRASWANAAIGILKLKGDKKTPE

VDQFYTPLLSSTMVSDELERPNVVKLGDKYYLFTA

SRLNHGSNNDAWNKANEVVGDNVVMLGYVSDQLTN

GYKPLNNSGVVLTASVPADWRTATYSYYAVPVAGS

SDTLLMTAYMTNRNEVAGKGKNSTWAPSFLIQVLP

DGTTKVLAEMTQQGDWIWDEPSRTTDTVGTLDTAY

LPGENDGYIDWNVIGGYGLKPHTPGQYQPTVPSTP

IHTDDIISFEVSEDGHLVIKPVKVNNDSAGRIDQS

RNSGGSLNVAENVSAGGNISVKPSQKSINNTKETK

KAHHVSTEKKQKKGNSFFAALLALFSAFCVSIGFK

Amino acid sequence of
Ln. mesenteroides
CW28 ISLA
                                SEQ ID NO: 17
MKQQESMARKKLYKAGKIWVAAATVSAVIGVSAIT

NVSADVNQPLLAQENFSGNKTEPVPDKSNKNESVK

DSKVATSDELAKDSKVATSDELAKDSKVATSDELA

KDSKVATSDELVKDSKVATSDELAKDSKVATSDEL

AKDSKVATSDELAKDSKVATSDELAKDSKVATSDE
```

```
                         -continued
LAKDSKAPTNDVSVRAEKKSSLIDSPELNVKMSEM

TSVPNLISDENSKNLVNSNELINGLSKRSLEIAHQ

AGIDVSRLNDIQKAALNKIKLVNEDGNKYVLDNTG

SDYTKNTIIDKNNPDDTTKTTHITFANLDDAIKLA

QKPDPKTTIPVFNASQINNLPASIFKDAQTNK

VEKMDVWDSWALQDSKTGEVYNYHGKQVVFALMGA

PLVQGDTHIYMLYNNYNNAKLDGWVNAGPVFGYNA

KPESQEWSGSAVVNSDDSIQLFYTRVADDWKQALA

TVNIKITNSENSLGIQSLQNDHILFEGDGYFYSRK

DQLKPQADMFTLRDPKLIELDDDGERYLTFEANTGI

YDEASDQQTVNLNNYGGGLTYDVARMLGVVNNSNR

ALYSSTANGAIGLLKLKGDYFNPILDRLYKPLITA

VGVTDEIERANIVPFNGKYYLFTDSRFNRSAADNS

PMSMAPDGAMMMGEVSDSLFGDYKPLNGNGIVLVT

NNSFTSRTNTYSWYTVPVKGRPDLMLVTSYMTNRG

LASGTDQYSTFAPSFLLKIDGDQTHVLNTVTEQGD

WVWGDDDHSIVELLALNTEDAYLTNNQKNINYSPD

WSNIDGYGYPIVTNIKDVDLTFYISGILSPDSLFK

NAPGRHQGARIIGSTSQYNTEKVSAIKEYTDDLNT

IWYLVNLAGNNFWIKGSSLVTVPMTDSTERNAYIV

KDSDMYLDAPQGETNAKYYQSSNSYNDAYVIVGGE

YKDAHGITWNLIKLNDKILWINKNSLAISFSRDLN

AKAFVNATSRNDGLFLNAPYRQVGSELVGFTKKYN

GQIVAIDKQFFDDKGIIWSQVIIDGQKFWVDNRGL

NQVQTQDVNKKLYVNSASQSDGLFLNAPYRGINAK

LVAMAKTYNGRYVNVLKQGKDAYNVNWSLIELDGQ

SLWIDSQALNTNFTHDMNQKVFVNTTSNLDGLFLN

APYRQPGYKLAGLAKNYNNQTVTVSQQYFDDQGTG

WSEVVLGGQTVWVDNHALAQMQVSDTSQQLYVNSN

GRNDGLFLNAPYRGQGSQLIGMTADYNGQHVQVTK

QGQDAYGAQWRLITLNNQQVWVDSRALSTTIMQAM

NDDMYVNSNQRTDGLWLNAPYTMSGAKWAGDTRLA

NGRYVHISKAYSNEVGNTYYLTNLNGQSTWIDKRA

FTATFDQVVALNATIVARQRPDGMFKTAPIWEAGA

QFVDYVTNYNQQTVPVTKQHSDAQGNQWYLATVNG

TQYWIDQRSFSPVVTKVVDYQAKIVPRTTRDGVFS

GAPYGEVNAKLVNMATAYQNQVVHATGEYTNASGI

TWSQFALSGQEDKLWIDKRALQA
```

Amino acid sequence of Z. mobilis
ATCC 10988 LEVU

SEQ ID NO: 18

MLNKAGIAEPSLWTRADAMKVHTDDPTATMPTIDY

DFPVMTDKYWVWDTWPLRDINGQVVSFQGWSVIFA

LVADRTKYGWHNRNDGARIGYFYSRGGSNWIFGGH

LLKDGANPRSWEWSGCTIMAPGTANSVEVFFTSVN

DTPSESVPAQCKGYIYADDKSVWFDGFDKVTDLFQ

ADGLYYADYAENNFWDFRDPHVFITPKIGKTYALF

EGNVAMERGTVAVGEEEIGPVPPKTETPDGARYCA

AAIGIAQALNEARTEWKLLPPLVTAFGVNDQTERP

HVVFQNGLTYLFTISHHSTYADGLSGPDGVYGFVS

ENGIFGPYEPLNGSGLVLGNPSSQPYQAYSHYVMT

NGLVTSFIDTIPSSDPNVYRYGGTLAPTIKLELVG

HRSFVTEVKGYGYIPPQIEWLAEDESSNSAAALSL

LNK

Amino acid sequence of
G. diazotrophicus
SRT4 LDSA

SEQ ID NO: 19

MAHVRRKVATLNMALAGSLLMVLGAQSALAQGNFS

RQEAARMAHRPGVMPRGGPLFPGRSLAGVPGFPLP

SIHTQQAYDPQSDFTARWTRADALQIKAHSDATVA

AGQNSLPAQLTMPNIPADFPVINPDVWVWDTWTLI

DKHADQFSYNGWEVIFCLTADPNAGYGFDDRHVHA

RIGFFYRRAGIPASRRPVNGGWTYGGHLFPDGASA

QVYAGQTYTNQAEWSGSSRLMQIHGNTVSVFYTDV

AFNRDANANNITPPQAIITQTLGRIHADFNHVWFT

GFTAHTPLLQPDGVLYQNGAQNEFFNFRDPFTFED

PKHPGVNYMVFEGNTAGQRGVANCTEADLGFRPND

PNAETLQEVLDSGAYYQKANIGLAIATDSTLSKWK

FLSPLISANCVNDQTERPQVYLHNGKYYIFTISHR

TTFAAGVDGPDGVYGFVGDGIRSDFQPMNYGSGLT

MGNPTDLNTAAGTDFDPSPDQNPRAFQSYSHYVMP

GGLVESFIDTVENRRGGTLAPTVRVRIAQNASAVD

LRYGNGGLGGYGDIPANRADVNIAGFIQDLFGQPT

SGLAAQASTNNAQVLAQVRQFLNQ

---

What is claimed is:

1. A method of producing an inulosaccharide product, comprising:
   providing an inulosucrase by expressing a recombinant nucleic acid encoding the inulosucrase from a host cell, wherein the recombinant nucleic acid is heterologous to the host cell, and
   contacting the inulosucrase with a fructose source to produce the inulosaccharide product,
   wherein the inulosucrase (i) comprises an amino acid sequence that is at least 90% identical to amino acids 32-453 of SEQ ID NO: 4, and (ii) catalyzes polymerization of inulin oligosaccharides containing β-(2→1) linkages.

2. The method of claim 1, wherein the fructose source is a food that contains sucrose.

3. The method of claim 1, wherein the inulosaccharide product has a GF range of GF3-GF100, GF3-GF30, or GF10-GF25.

4. The method of claim 2, wherein the inulosaccharide product has a GF range of GF3-GF100.

5. The method of claim 2, wherein the inulosaccharide product has a GF range of GF3-GF30.

6. The method of claim 1, wherein the fructose source is sucrose, stachyose, raffinose, inulin, or a fructooligosaccharide.

7. The method of claim 1, wherein the inulosucrase comprises an amino acid sequence that is at least 95% identical to amino acids 32-453 of SEQ ID NO:4.

8. The method of claim 1, wherein the inulosucrase comprises an amino acid sequence that is at least 98% identical to amino acids 32-453 of SEQ ID NO:4.

9. The method of claim 1, wherein the inulosucrase comprises amino acids 32-453 of SEQ ID NO:4.

10. The method of claim 2, wherein the inulosucrase comprises an amino acid sequence that is at least 95% identical to amino acids 32-453 of SEQ ID NO:4.

11. The method of claim 2, wherein the inulosucrase comprises an amino acid sequence that is at least 98% identical to amino acids 32-453 of SEQ ID NO:4.

12. The method of claim 2, wherein the inulosucrase comprises amino acids 32-453 of SEQ ID NO:4.

13. The method of claim 1, wherein the fructose source is a juice.

14. The method of claim 1, wherein the fructose source is a yogurt.

15. The method of claim 1, wherein the host cell is a bacterial cell.

16. The method of claim 1, wherein the host cell is a fungal cell.

17. The method of claim 1, wherein the host cell is a *Bacillus* species cell, wherein the *Bacillus* species is not *Bacillus agaradhaerens*.

18. The method of claim 1, wherein said contacting is performed under a temperature of 40° C. to 60° C. and a pH of 5 to 10.

19. A method of producing a tailored oligofructoside product, comprising:
   providing an inulosucrase by expressing a recombinant nucleic acid encoding the inulosucrase from a host cell, wherein the recombinant nucleic acid is heterologous to the host cell, and contacting the inulosucrase with a sucrose analogue having the glucose cap of sucrose substituted by another saccharide to produce the tailored oligofructoside product, wherein the inulosucrase (i) comprises an amino acid sequence that is at least 90% identical to amino acids 32-453 of SEQ ID NO: 4, and (ii) catalyzes polymerization of inulin oligosaccharides containing β-(2→1) linkages, wherein the sucrose analogue has the glucose cap of sucrose substituted by a galactose, a mannose, a fucose, or a xylose.

20. The method of claim 19, wherein said contacting is performed under a temperature of 40° C. to 60° C. and a pH of 5 to 10.

* * * * *